(12) United States Patent
Fraga-Dubreuil et al.

(10) Patent No.: US 9,050,591 B2
(45) Date of Patent: *Jun. 9, 2015

(54) NICKEL FORM FOR PREPARATION OF CATALYTIC NICKEL-LIGAND COMPLEXES

(75) Inventors: Joan Fraga-Dubreuil, Middlesbrough (GB); Vinay Medhekar, Beaumont, TX (US); Thomas A. Micka, West Grove, PA (US); Keith Whiston, Darlington (GB)

(73) Assignee: INVISTA North America S.a.r.l., Wilmington, DE (US)

( * ) Notice: Subject to any disclaimer, the term of this patent is extended or adjusted under 35 U.S.C. 154(b) by 156 days.

This patent is subject to a terminal disclaimer.

(21) Appl. No.: 13/490,177

(22) Filed: Jun. 6, 2012

(65) Prior Publication Data

US 2013/0144082 A1 Jun. 6, 2013

Related U.S. Application Data

(60) Provisional application No. 61/495,796, filed on Jun. 10, 2011, provisional application No. 61/496,142, filed on Jun. 13, 2011, provisional application No. 61/503,917, filed on Jul. 1, 2011, provisional application No. 61/507,159, filed on Jul. 13, 2011, provisional application No. 61/552,473, filed on Oct. 28, 2011.

(51) Int. Cl.

| | |
|---|---|
| *B01J 31/24* | (2006.01) |
| *B01J 31/18* | (2006.01) |
| *C07C 253/10* | (2006.01) |
| *C22B 23/02* | (2006.01) |
| *B01J 35/00* | (2006.01) |
| *B01J 23/755* | (2006.01) |
| *B01J 35/10* | (2006.01) |

(52) U.S. Cl.
CPC .......... *B01J 31/2409* (2013.01); *B01J 31/1845* (2013.01); *B01J 31/185* (2013.01); *B01J 35/006* (2013.01); *B01J 2231/322* (2013.01); *B01J 2531/007* (2013.01); *B01J 2531/847* (2013.01); *C07C 253/10* (2013.01); *C22B 23/021* (2013.01); *B01J 23/755* (2013.01); *B01J 35/002* (2013.01); *B01J 35/1009* (2013.01)

(58) Field of Classification Search
USPC .............. 428/402; 502/162; 556/13; 558/338
See application file for complete search history.

(56) References Cited

U.S. PATENT DOCUMENTS

| | | | |
|---|---|---|---|
| 3,496,215 A | 2/1970 | Drinkard et al. | |
| 3,496,217 A | 2/1970 | Drinkard, Jr. | |
| 3,631,191 A | 12/1971 | Kane et al. | |
| 3,655,723 A | 4/1972 | Drinkard, Jr. | |
| 3,672,873 A | 6/1972 | Huggins et al. | |
| 3,766,237 A | 10/1973 | Chia | |
| 3,816,098 A | 6/1974 | Mackiw et al. | |
| 3,846,461 A | 11/1974 | Shook, Jr. | |
| 3,847,959 A | 11/1974 | Shock, Jr. et al. | |
| 3,903,120 A | 9/1975 | Shook, Jr. et al. | |
| 3,914,124 A | 10/1975 | O'Neill et al. | |
| 4,045,541 A | 8/1977 | Mercer | |
| 4,118,342 A | 10/1978 | Debus et al. | |
| 4,416,825 A | 11/1983 | Ostermaier | |
| 4,749,801 A | 6/1988 | Beatty et al. | |
| 4,946,068 A | 8/1990 | Erickson et al. | |
| 5,512,696 A | 4/1996 | Kreutzer et al. | |
| 5,688,986 A | 11/1997 | Tam et al. | |
| 5,723,641 A | 3/1998 | Tam et al. | |
| 5,787,353 A | 7/1998 | Kibbe et al. | |
| 5,981,722 A | 11/1999 | Chen et al. | |
| 6,069,267 A | 5/2000 | Tam et al. | |
| 6,171,996 B1 | 1/2001 | Garner et al. | |
| 6,494,931 B1 | 12/2002 | Mukuno et al. | |
| 6,906,218 B2 | 6/2005 | Allgeier et al. | |
| 7,056,565 B1 | 6/2006 | Cai et al. | |
| 7,345,006 B2 | 3/2008 | Bartsch et al. | |
| 7,470,805 B2 | 12/2008 | Rosier et al. | |

(Continued)

FOREIGN PATENT DOCUMENTS

| | | |
|---|---|---|
| CN | 101478044 A | 7/2009 |
| CN | 101733106 A | 6/2010 |

(Continued)

OTHER PUBLICATIONS

"U.S. Appl. No. 10/993,622, Non-Final Office Action mailed Jul. 8, 2009", 7 pgs.
"U.S. Appl. No. 12/968,341, Final Office Action mailed Nov. 6, 2013", 12 pgs.
"U.S. Appl. No. 12/968,341, Non Final Office Action mailed Mar. 20, 2013", 12 pgs.
"U.S. Appl. No. 12/968,341, Response filed Jan. 13, 2014 to Final Office Action mailed Nov. 6, 2013", 15 pgs.
"U.S. Appl. No. 12/968,373 , Response filed Feb. 11, 2013 to Final Office Action mailed Dec. 17, 2012", 11 pgs.
"U.S. Appl. No. 12/968,373, Final Office Action mailed Dec. 17, 2012", 12 pgs.
"U.S. Appl. No. 12/968,373, Non Final Office Action mailed Oct. 21, 2013", 12 pgs.

(Continued)

*Primary Examiner* — Porfirio Nazario Gonzalez
(74) *Attorney, Agent, or Firm* — Robert B. Furr, Jr.; Nicholas P. Lanzatella

(57) ABSTRACT

A novel nickel particulate form is provided that efficiently forms a zero-valent nickel complex with a phosphorus-containing ligands in an organic liquid to form a hydrocyanation catalyst. Particles in the nickel particulate form comprise nickel crystallites. For example, the nickel particulate form can have a BET Specific Surface Area of at least about 1 $m^2/gm$; an average crystallite size less than about 20-25 nm, the nickel particulate form can have at least 10% of the crystallites in the nickel form can have a diameter (C10) of less than about 10 nm, and/or there are on average at least about $10^{15}$ surface crystallites per gram nickel. A ratio of BET SSA to C50 for the nickel particulate form can be at least about $0.1 \times 10^9$ m/gm and preferably at least about $0.4 \times 10^9$ m/gm. Methods of preparation and use are also provided.

42 Claims, 20 Drawing Sheets

(56) References Cited

U.S. PATENT DOCUMENTS

| | | | |
|---|---|---|---|
| 7,528,275 | B2 | 5/2009 | Bartsch et al. |
| 7,531,682 | B2 | 5/2009 | Galland et al. |
| 7,629,484 | B2 | 12/2009 | Ritter et al. |
| 7,854,973 | B2 | 12/2010 | Dey |
| 8,815,186 | B2 | 8/2014 | Ostermaier |
| 2003/0100802 | A1 | 5/2003 | Shapiro |
| 2004/0106815 | A1 | 6/2004 | Ritter |
| 2006/0107792 | A1 | 5/2006 | Collins et al. |
| 2008/0015381 | A1 | 1/2008 | Foo et al. |
| 2011/0196168 | A1 | 8/2011 | Ostermaier et al. |
| 2011/0311428 | A1 | 12/2011 | Ostermaier |
| 2013/0143730 | A1* | 6/2013 | Fraga-Dubreuil et al. .... 502/167 |
| 2013/0144079 | A1 | 6/2013 | Medhekar et al. |
| 2013/0317242 | A1 | 11/2013 | Ostermaier et al. |
| 2013/0345459 | A1 | 12/2013 | Ostermaier |

FOREIGN PATENT DOCUMENTS

| | | | |
|---|---|---|---|
| EP | 0114704 | A2 | 8/1984 |
| EP | 0673841 | A2 | 9/1995 |
| EP | 0985448 | A1 | 3/2000 |
| EP | 1724363 | A1 | 11/2006 |
| GB | 146407 | A | 11/1921 |
| GB | 255884 | A | 4/1927 |
| GB | 703826 | A | 2/1954 |
| GB | 2465467 | A | 5/2010 |
| JP | 2001-335326 | A | 12/2001 |
| WO | WO-2006/052677 | A1 | 5/2006 |
| WO | WO-2007/130206 | A1 | 11/2007 |
| WO | WO-2011/075494 | A1 | 6/2011 |
| WO | WO-2011/075496 | A1 | 6/2011 |
| WO | WO-2011/094411 | A1 | 8/2011 |
| WO | WO-2012/170297 | A2 | 12/2012 |
| WO | WO-2012/170300 | A2 | 12/2012 |
| WO | WO-2012/170537 | A2 | 12/2012 |

OTHER PUBLICATIONS

"U.S. Appl. No. 12/968,373, Notice of Allowance mailed Apr. 25, 2014", 7 pgs.

"U.S. Appl. No. 12/968,373, Response filed Dec. 5, 2013 to Non Final Office Action mailed Oct. 21, 2013", 15 pgs.

"U.S. Appl. No. 13/490,116, Final Office Action mailed Apr. 16, 2014", 6 pgs.

"U.S. Appl. No. 13/490,116, Non Final Office Action mailed Feb. 19, 2014", 7 pgs.

"U.S. Appl. No. 13/490,116, Notice of Allowance mailed Jun. 23, 2014", 5 pgs.

"U.S. Appl. No. 13/490,116, Response filed Apr. 9, 2014 to Final Office Action mailed Feb. 19, 2014", 11 pgs.

"U.S. Appl. No. 13/490,116, Response filed Jun. 12, 2014 to Final Office Action mailed Apr. 16, 2014", 10 pgs.

"U.S. Appl. No. 13/490,207, Advisory Action mailed Jul. 28, 2014", 3 pgs.

"U.S. Appl. No. 13/490,207, Final Office Action mailed May 19, 2014", 10 pgs.

"U.S. Appl. No. 13/490,207, Non Final Office Action mailed Oct. 22, 2013", 11 pgs.

"U.S. Appl. No. 13/490,207, Response filed Feb. 20, 2014 to Non Final Office Action mailed Oct. 22, 2013", 15 pgs.

"U.S. Appl. No. 13/490,207, Response filed Aug. 19, 2014 to Final Office Action mailed May 19, 2014 and Advisory Action mailed Jul. 28, 2014", 13 pgs.

"U.S. Appl. No. 13/490,207, Restriction Requirement mailed Jun. 14, 2013", 16 pgs.

"U.S. Appl. No. 13/821,174, Non Final Office Action mailed Jun. 27, 2014", 5 pgs.

"U.S. Appl. No. 13/821,174, Response filed Sep. 19, 2014 to Non Final Office Action mailed Jun. 27, 2014", 8 pgs.

"Chapter 27—Nickel, Palladium and Platinum", In: Chemistry of the Elements (1st Edition), Greenwood, N. N., et al., Pergamon Press, Oxford, (1984), 1328-1363.

"CN 101478044A, published Jul. 8, 2009—English Translation", 17 pgs.

"English Translation of JP 2001-335326A, published Dec. 4, 2001", 5 pgs.

"International Application Serial No. PCT/US2012/040466, International Preliminary Report on Patentability dated Nov. 14, 2013", 20 pgs.

"International Application Serial No. PCT/US2012/040466, International Search Report mailed Mar. 11, 2013", 11 pgs.

"International Application Serial No. PCT/US2012/040466, Written Opinion mailed Mar. 11, 2013", 21 pgs.

"International Application Serial No. PCT/US2012/041107, International Preliminary Report on Patentability dated Oct. 17, 2013", 28 pgs.

"International Application Serial No. PCT/US2012/041107, International Search Report mailed Mar. 15, 2013", 5 pgs.

"International Application Serial No. PCT/US2012/041107, Response filed Jun. 17, 2013 to Written Opinion mailed Mar. 15, 2013", 9 pgs.

"International Application Serial No. PCT/US2012/041107, Written Opinion mailed Mar. 15, 2013", 14 pgs.

"JP 03-249943A, published Nov. 7, 1991—English Translation", 4 pgs.

"JP 07-005494A, published Jan. 10, 1995—English Translation", 4 pgs.

"JP 2001-335326A, published Dec. 4, 2001—English Translation", 4 pgs.

"Machine translation of JP 2001-335326", [online]. [retrieved on Mar. 11, 2013] Retrieved from the Internet: <http:/ /dossier. ipdl. i npit.go.jp/text_trans. html >, (2013), 9 pgs.

"Sodium carbonate—SIDS Initial Assessment Report for SIAM 15", UNEP Publications, (Oct. 2002), 85 pgs.

Brunauer, S., et al., "Adsorption of Gases in Multimolecular Layers", *J. Am. Chem. Soc.*, 60, (1938), 309-319

Carlsson, T., et al., "Coprecipitation of Ni with CaCO3: An experimental study", *VIT Research Notes 1712*, Technical Research Centre of Finland, (1995), 28 pgs.

Carriel, Jonathan T., et al., "Composition of Basic Nickel Carbonates", *Journal of the American Chemical Society*, 76, (1954), 3839-3843.

Chen, I., et al., "Resistivity to sulfur poisoning of nickel-alumina catalysts", *Ind, Eng. Chem. Res.*, 27(8), (1988), 1391-1396.

Cloutier, L., et al., "The study of the precipitation of carbonates", Proceedings and *Transactions of the Royal Society of Canada*, 33(III), (1936), 149-164.

Costodes, V. C., et al., "Reactive crystallization of nickel hydroxycarbonate in fluidized-bed reactor: Fines production and column design", *Chemical Engineering Science*, 61(5), (2006), 1377-1385

Crosa, M., et al., "Determination of Mean Crystalite Dimensions from X-Ray Diffraction Peak Profiles: A Comparative Analysis of Synthetic Hematites", *Clays and Clay Materials*, 47(6), (1999), 742-747.

Davidson, J. Michael, et al., "Nucleation Kinetics in the Reactions of Nickel Basic Carbonates with Hydrogen Sulfide: The Carbonate Precipitation Reactions of Divalent Nickel", *Industrial & Engineering Chemistry Research*, 46(14), (2007), 4772-4777.

Evlash, Yu, et al., "Precipitation of basic nickel carbonate", *Zhurnal Prikladnoi Khimii* (Sankt-Peterburg, Russian Federation), 58(11), (1985), 2417-2421.

Formanek, Lothar, et al., "Iron, 3. Direct Reduction Processes", In: *Ullmann's Encyclopedia of Industrial Chemistry*, vol. 19, Wiley-VCH Verlag GmbH & Co., Weinheim, Germany, (2000), 711-726.

Francois-Rossetti, Jeannine, et al., "Structure and constitution of basic nickel carbonates", *Journal de Chimie Physique et de Physico-Chimie Biologique*, 51, (1954), 451-460.

Gagnon, Paul E., et al., "Contribution to the study of the precipitation of carbonates, borates, silicates and arsenates", *Canadian Journal of Research, Section B: Chemical Sciences*, 19, B, (1941), 179-204.

Guillard, Damien, et al., "Nickel Carbonate Precipitation in a fluidized-Bed Reactor", *Industrial & Engineering Chemistry Research*, 40(23), (2001), 5564-5569.

(56) References Cited

OTHER PUBLICATIONS

Guillard, Damien, et al., "Optimization of Nickel Hydroxycarbonate Precipitation Using a Laboratory Pellet Reactor", *Industrial & Engineering Chemistry Research*, 41(13), (2002), 3110-3114.

Guo, Xue-Yi, et al., "Preparation of basic nickel carbonate particles in solution system of Ni(II)—NH3—CO2-3—H2O", *Transactions of the Nonferrous Metals Society of China*, 14(5), (2004), 1006-1011.

Guo, Xueyi, et al., "Study on the thermodynamic equilibrium of the complex system of Ni(II)—$NH_3^{2-}H_2O$ and its application to the precipitation of basic nickel carbonate particles.", *EPD Congress 2004 as held at the 2004 TMS Annual Meeting*, (2004), 443-456.

Hoffmann, U., et al., "Preliminary results on the behavior of Ni(II) in the calcite-water system", *Mineralogical Magazine*, 62A(Pt. 2), (1998), 642-643.

Ito, Y., et al., "Characterization of a participle size distribution in a Ni—C granular thin film by grazing incidence small-angle x-ray scattering", *Journal of Physics: Conference Series*, vol. 83, (2007), 1-4.

Jaulmes, P., et al., "Solubility and precipitation of slightly soluble salts of weak or moderately strong acids", *Travaux de la Societe de Pharmacie de Montpellier*, 25(2), (1965), 98-100.

Kerfoot, Derek G. E., "Nickel", In: *Ullmann's Encyclopedia of Industrial Chemistry*, Wiley-VCH Verlag GmbH & Co., Weinheim,DE, (2000), 37-101.

Kucha, M. I., "Manufacture of basic nickel carbonate", Issled. i Razrab. Syr'ya dlya Prigot. Katalizatorov, M., From: Reference *Zh., Khim. 1992, Abstract No. 12L142*, (1991), 41-43.

Lascelles, K., "Nickel Compounds", In: *Ullman's Encyclopedia of Industrial Chemistry*, vol. 24, Wiley-VCH Verlag GmbH & Co., Weinheim, Germany, (2005), 117-131.

Lee, Chang-Hwan, et al., "A Study on Nickel Hydroxide Crystallization Characteristics", *Korean Journal of Chemical Engineering* (22(5), (2005), 712-716.

Lewis, A. E., "Fines Formation (and Prevention) in Seeded Precipitation Processes", *KONA*, No. 24, (2006), 119-125.

Li, J., et al., "Formation of Dispersive NiO Nano-particles via Hydrothermal Modification", (English Abstract), *Xiyou Jinshu Cailiao yu Gongcheng (Rare Metal Materials and Engineering*, 33(4), (Apr. 2004), 425-428.

Liu, Fang, et al., "An Improved Purification Method for Preparation of Basic Nickel Carbonate of High Purity via Chemical Precipitation", *Journal of Wuhan University of Technology—Materials Science Edition*, 23(3), (Jun. 2008), 331-333.

Makarov, V. N., et al., "Optimization of Natural Water Purification to Remove Nickel and Copper Ions with Carbonate Flour", *Russian Journal of Applied Chemistry (Translation of Zhurnal Prikladnoi Khimii)*, 74(12), (2001), 2045-2050.

Mallya, R. M., et al., "Studies on the Basic Carbonates of Nickel. Part I: Factors Influencing the Precipitation of Nickel Carbonates", *Journal of the Indian Institute of Science*, 43, (1961), 44-51.

Mallya, R. M., et al., "Studies on the Basic Carbonates of Nickel. Part II: Hydrated Basic Nickel Carbonates", *Journal of the Indian Institute of Science*, 43(2), (1961), 65-75.

Mallya, R. M., et al., "Studies on the Basic Carbonates of Nickel. Part III: Potentiometric Stud of Precipitation", *Journal of the Indian Institute of Science*, 43, (1961), 76-86.

Mallya, R. M., et al., "Studies on the Basic Carbonates of Nickel. Part IV: Preparation of Basic Nickel Carbonate and their Differential Thermal Analysis", *Journal of the Indian Institute of Science*, 43, (1961), 87-96.

Mallya, R. M., et al., "Studies on the Basic Carbonates of Nickel. Part V: Thermogravimetric Behavior of Basic Nickel Carbonates", *Journal of the Indian Institute of Science*, 43(3), (1961), 131-40.

Mallya, R. M., et al., "Studies on the Basic Carbonates of Nickel. Part VI: Thermal Decomposition of Basic Nickel Carbonates in Vacuum and the nature of the surfaces", *Journal of the Indian Institute of Science*, 43(3), (1961), 141-147.

Mallya, R. M., et al., "Studies on the Basic Carbonates of Nickel. Part VII: Formation and Configurations of Basic Nickel Carbonates", *Journal of the Indian Institute of Science*, 43(3), (1961), 148-157.

Minkova, N., et al., "Precipitation processes in obtaining basic nickel(II) carbonate and coprecipitation of other basic nickel salts. I. Preparation of basic nickel carbonate free of sulfate ions", *Izvestiya po Khimiya*, 13(2), (1980), 222-228.

Minkova, N., et al., "Precipitation processes in obtaining nickel(II) hydroxocarbonate and co-precipitation of other nickel hydroxo salts. II. Influence of the conditions for obtaining nickel(II) hydroxocarbonate on the amount of co-precipitated sulfate ions", *Izvestiya po Khimiya*, 16(4), (1983), 432-435.

Mittemeijer, E. J., et al., "The "state of the art" of the diffraction analysis of crystallite size and strain", *Zeitschrift für Kristallographie—Crystalline Materials*, 223(9), (2008), 552-560.

Nassler, J., "A new type of basic nickel(II) carbonate", *Collection of Czechoslovak Chemical Communications*, 29(1), (1964), 168-173.

Nitta, Y., et al., "Preparation Chemistry of Precipitated Ni—$SIO_2$ Catalysts for Enantioselective Hydrogenation", *Journal of Catalysis*, 96(2), (1985), 429-438.

Nordhei, C., et al., "Nanophase cobalt, nickel and zinc ferrites: synchrotron XAS study on the crystallite size dependence of metal distribution", *Phys. Chem. Chem. Phys.*, 10, (2008), 1053-1066.

Ozheredova, M. A., et al., "Nickel-containing rinsing waters. Effect of additives and the nature of the precipitant on the degree of treatment", *Khimichna Promislovist Ukraini* (Kiev, Ukraine), (3), (2005), 41-43.

Packter, A., et al., "Precipitation of basic nickel carbonate powders from aqueous solution. Crystallite numbers, composition, and final sizes", *Kristall und Technik*, 10(9), (1975), 985-994.

Pistorius, C. W., "High-Pressure Preparation and Structure of Crystalline Nickelous Carbonate", *Experientia*, 15, (1959), 328-329.

Queneauc, P., et al., "Part II—The Inco Pressure Carbonyl (IPC) process", *J. of Metals*, 21, (1969), 41-45

Rhamdhani, M. A., et al., "Basic Nickel Carbonate: Part I. Microstructure and Phase Changes during Oxidation and Reduction Processes", *Metallurgical and Materials Transactions B*, 39)2), (2008), 218-233.

Rhamdhani, M. A., et al., "Basic Nickel Carbonate: Part II. Microstructure Evolution during Industrial Nickel Production from Basic Nickel Carbonate", *Metallurgical & Materials Transactions B*, 39(2), (2008), 234-245.

Richardson, Y., et al., "In situ generation of Ni metal nanoparticles as catalyst for H2-rich syngas production from biomass gasification", *Applied Catalysis A: General*, 382(2), (2010), 220-230.

Scardi, P., "Chapter 13. Microstructural Properties: Lattice Defects and Domain Size Efffects", In: *Powder Diffraction Theory and Practice*, Dinnebier, R. E., et al., Editors, RSC, Cambridge, (2008), 376-413.

Sergeev, M., "The influence of temperature on the precipitation of nickel carbonate", *Masloboino-Zhirovoe Delo*, (No. 11), (1928), p. 15.

Taylor, N. J., et al., "Synthesis and Crystal Structure of the Novel Cyclometallophosphine Complex $Re_4Cl_2$ $(CO)_{15}$-{MePP(Me)PMe}", *Journal of the Chemical Society, Chemical Communications*, 8, (1985), 476-477.

Teixeira, A. C. S.C., et al., "Deactivation of steam reforming catalysts by sintering: experiments and simulation", *Chemical Engineering Science*, 54(15-16), (1999), 3609-3618.

Tolman, C. A., et al., "Homogeneous Nickel-Catalyzed Olefin Hydrocyanation", *Advances in Catalysis*, 33, (1985), 1-46

Ueno, Seiichi, et al., "Influence of the conditions of precipitation on the activity of nickel catalysts. II. Precipitation with sodium carbonate", *Kogyo Kagaku Zasshi*, 46, (1943), 45-47.

Ungar, T., et al., "Crystallite size distribution and dislocation structure determined by diffraction profile analysis: princiiples and practical application to cubic and hexagonal crystals", *Journal of Applied Crystallography*, 34(3), (2001), 298-310.

Van Weert, G., et al., "The production of nickel carbonate spheroids from dilute solutions in a pellet reactor.", *Conference: Extractive Metallurgy of Copper, Nickel and Cobalt. vol. I: Fundamental Aspects*, Denver, Colorado, USA, Feb. 21-25, 1993, (1993), 1133-1144.

(56) References Cited

OTHER PUBLICATIONS

Vasserman, I. M., et al., "Continuous method for the precipitation of basic nickel carbonate by an automated process", *Tsvetnye Metally* (Moscow, Russian Federation), 37(12) (1964), 25-31.

Vasserman, I. M., et al., "Separation of substances from solutions by chemical precipitation. III. Automatic control of the process of precipitation of basic nickel carbonate in the system Ni $(NO_3)_2$—$Na_2CO_3$—$H_2O$ by the pH of the solution", *Kh. Z. Branina. Zhur. Priklad. Khim.*, 32, (1959), 2619-2624.

Xiang, L., et al., "Experimental study on synthesis of NiO nanoparticles", *Scripta Materials*, 47, (2002), 219-224.

Zhou, Ping, et al., "Study of a Novel Process for Removal of Heavy Metals from Industrial Wastewater", (English Abstract), *Zhongguo Jishui Paishui*, 14(4), (1998), 17-20.

\* cited by examiner

NICKEL FORM FOR PREPARATION OF CATALYTIC NICKEL-LIGAND COMPLEXES

This application claims benefit of the filing date of U.S. Provisional Patent Application No. 61/495,784, filed Jun. 10, 2011; U.S. Provisional Patent Application No. 61/496,142, filed Jun. 13, 2011; U.S. Provisional Patent Application No. 61/503,917, filed Jul. 1, 2011; U.S. Provisional Patent Application No. 61/507,159, filed Jul. 13, 2011; and U.S. Provisional Patent Application No. 61/552,473, filed Oct. 28, 2011, the contents of which applications are all specifically incorporated herein by reference in their entireties.

BACKGROUND OF THE INVENTION

Some types of nickel metal catalyst systems are available in the art. For example, nickel-phosphorus ligand catalyst systems have been used for hydrocyanation of butadiene to form pentenenitrile (PN) and for hydrocyanation of pentenenitrile to form adiponitrile (ADN). Examples of catalyst compositions and processes for the hydrocyanation of monoethylenically unsaturated compounds using zero-valent nickel and bidentate phosphite ligands in the presence of Lewis acid promoters include those described, for example in U.S. Pat. Nos. 5,512,696; 5,723,641; and 6,171,996.

Some nickel preparations and/or nickel complexes are also described, for example, in GB14607A, GB255884A, GB703826A, EP101733106A, EP0114704, EP0985448A1 and in U.S. Pat. Nos. 4,416,825 3,903,120; 3,496,217; 3,631, 191; 3,816,098; 3,846,461; 3,847,959; 3,903,120; 4,118,342; 6,171,996; and 6,494,931.

Formation of hydrocyanation catalysts can involve formation of complexes between nickel atoms and phosphorus-containing ligands. However, commercially available sources of nickel often do not efficiently form these complexes. Moreover, different batches and lots of nickel from the same supplier often have different compositions and exhibit unpredictable activity for forming nickel-ligand complexes. For example, as illustrated herein, nickel starting materials from different batches and diverse commercial sources can exhibit up to 200% variability in their ability to form complexes with phosphorus-containing ligands. Different types of phosphorus-containing ligands also vary in their ability to form catalytic complexes with nickel. Such variability in complex formation by currently available nickel sources and ligands leads to low efficiency catalysts and manufacturing processes, as well as significant waste.

To solve the problems of inefficient nickel-ligand complex formation, manufacturers have previously employed activators such as phosphorus trichloride ($PCl_3$) to promote the formation of catalytically active nickel complexes with monodentate phosphorus-containing ligands. See, e.g., U.S. Pat. No. 5,688,986 to Tam, Kreutzer & McKinney. However, such activators can react with some phosphorus-containing ligands and inactivate the ligands. Thus, the useful lifetime of catalysts can be shortened by use of activators. Therefore, improved nickel metal preparations and methods of making catalytically active nickel-ligand complexes are needed.

SUMMARY OF THE INVENTION

The invention solves the problem of short-lived, poorly forming nickel-ligand catalyst complexes by providing methods of making the complexes without an activator that could destroy the ligand and by providing forms of nickel that readily complex with phosphorus-containing ligands. For example, particulate nickel forms with the physical properties described herein can readily form complexes with phosphorus-containing ligands without addition of activators that destroy the ligands. The invention also solves the problems of nickel metal particles with variable activity for forming nickel-ligand catalyst complexes by providing methods for identifying and making particulate nickel forms that are highly active for complex formation.

The inventive particulate nickel forms exhibit desirable physical properties such as a BET Specific Surface Area of at least about 1 $m^2/gm$, preferably at least about 2 $m^2/g$; more preferably at least about 4 $m^2/g$ and more preferably at least about 10 $m^2/g$. In addition, desirable nickel particulate forms can also include an average crystallite size of no greater than about 100 nm; preferably no greater than 70 nm, and more preferably no greater than 50 nm. In desirable nickel particulate forms at least 10% of the crystallites have a size (C10) that is less than about 20 nm. Desirable nickel particulate forms also have on average have at least about $10^{16}$ surface crystallites of size C10 or less per gram nickel. However, addition of a sulfur source can cure or offset the poor ligand complexation activity of nickel particles with inadequate physical properties. For example, compositions of particulate nickel metal with about 0.1 wt % to about 15 wt % sulfur efficiently complex with phosphorus-containing ligands. Thus, nickel particles with inadequate physical properties can be used as a source of particulate nickel for making nickel-ligand catalysts with excellent catalytic activity when a sulfur source is added either during manufacture of the particulate nickel or during formation of the nickel-ligand complex. A nickel particulate form with a high BET Specific Surface Area, low average crystallite size, low C10 value, 0.1-15 wt % sulfur content, or a combination thereof, optimally form complexes with phosphorus-containing ligands.

One aspect of the invention is a nickel particulate form comprising nickel crystallites, wherein the nickel particulate form has a BET Specific Surface Area of at least about 1 $m^2/gm$; at least 10% of the nickel crystallites have a size (C10) that is less than about 20 nm; the nickel crystallites have an average crystallite size of no greater than about 100 nm; and the nickel crystallite size distribution span is greater than about 1.0. Such a nickel particulate form can also have a BET Specific Surface Area/C50 ratio of not less than $0.07 \times 10^9$ m/gm. In addition, the nickel particulate form can, on average, have at least about $10^{15}$ surface crystallites per gram of nickel. At least 10% of the particles of such a nickel particulate form can have a size (D10) of no greater than about 6 gm. The nickel particulate form can also have a Laser Diffraction Specific Surface Area of at least about 0.4 $m^2/gm$, and/or a BET Specific Surface Area to D10 ratio of about $0.3 \times 10^6$ m/gm to about $10.0 \times 10^6$ m/gm. The nickel particulate form can also have, on average, at least about $10^{16}$ surface crystallites per gram nickel that are smaller than or equal to size C10. With respect to complex formation, an equilibrium of complex formation between Ligand (V) and nickel atoms from the nickel particulate form can be reached within about 2 hours when about 4 to 5 wt % of the nickel particulate form is mixed with 3-pentenenitrile containing approximately 5.25 wt % Ligand (V) and approximately 6300 ppm $ZnCl_2$; and wherein Ligand (V) has the following formula:

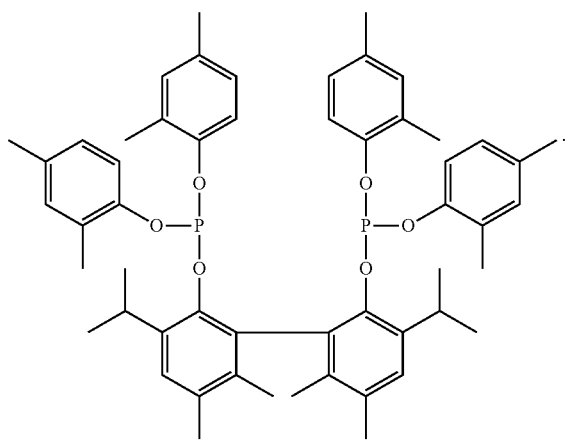

Any of the foregoing properties and features can be combined to describe the nickel particulate form.

The nickel particulate form provided herein can be described with several physical properties. For example, instead of a BET Specific Surface Area of at least about 1 m²/gm, the nickel particulate form can have a BET Specific Surface Area of at least about 2 m²/g, or of at least about 4 m²/g or of at least 10 m²/g. In another example, instead of a BET Specific Surface Area/C50 ratio of not less than 0.07× $10^9$ m/gm, the nickel particulate can have a BET SSA/C50 ratio is at least about 0.1×$10^9$ m/gm, or at least about 0.4×$10^9$ m/gm. For example, the nickel particulate can have a Laser Diffraction SSA/C50 ratio is at least about 4.3×$10^6$, or at least about 107. A ratio of BET Specific Surface Area to Laser Diffraction Specific Surface Area can be between 20 and 30. In another example, the nickel particulate form can have a ratio of BET Specific Surface Area to D10 that is from 3 to 5 m²/gm/μm, or is about 0.5×$10^6$ m/gm to about 5×$10^6$ m/g. Nickel particulate forms with any combination of the properties and features described herein are useful in nickel-ligand complexes.

The nickel particulate form can have a large number of small crystallites. For example, instead of average crystallite size of no greater than about 100 nm, the nickel particulate form can have an average crystallite size of no greater than about 70 nm, or no greater than about 50 nm, or no greater than about 30 nm. Instead of having nickel crystallites with a size (C10) that is less than about 20 nm, the nickel particulate form can have at least 10% of the crystallites with a size (C10) that is less than about 10 nm. Instead of having an average crystallite size of no greater than about 100 nm, the nickel particulate form can have an average crystallite size of no greater than about 20-25 nm. Instead of having a nickel crystallite size distribution span that is greater than about 1.0, the nickel particulate form can have a nickel crystallite size distribution span greater than 1.5. Instead of having at least about $10^{15}$ surface crystallites per gram of nickel, the nickel particulate form can have on average at least about 2×$10^{15}$ surface crystallites per gram nickel. Such a number of surface crystallites per gram nickel can be calculated for substantially cuboidal crystallites or for substantially spherical crystallites. Instead of having, on average, at least about $10^{16}$ surface crystallites per gram nickel that are smaller than or equal to size C10, the nickel particulate form can have on average there are at least about 5×$10^{16}$ surface crystallites of size C10 or less per gram nickel, or on average there are at least about $10^{17}$ surface crystallites of size C10 or less per gram nickel. Any of these physical properties can be combined to describe the nickel particulate form.

The nickel particulate form is substantially zero-valent nickel. Such a nickel particulate form can be generated by reduction of a nickel starting material. Examples of nickel starting materials can be selected from the group consisting of basic nickel carbonate, nickel carbonate, nickel bicarbonate, nickel oxalate, nickel formate, nickel squarate, nickel hydroxide, nickel oxide, nickel salts or a combination thereof. For example, the nickel particulate form can be reduced from Ni(II) to zero-valent nickel at 250-400° C. In general, the nickel particulate can be at least 95% to 99.9% free of another metal. For example, the nickel particulate form can be at least 95% to 99.9% free of aluminum, copper, tungsten, zinc and/or iron. The nickel particulate form can also be substantially free (e.g., at least 95% to 99.9% free) of alkali metals and/or alkaline earth metals. The nickel particulate form can also be at least 95% to 99.9% free of an anion, such as of carbonate, hydroxide and/or oxygen.

The nickel particulate form can include an amount of sulfur, For example, the nickel particulate form can include about 0.01 wt % to about 12 wt % sulfur, relative to the total weight of nickel in the mixture. Alternatively, the nickel particulate can include about 0.1 wt % to about 2 wt % sulfur, relative to the total weight of nickel in the mixture; or about 0.2 wt % to about 2 wt % sulfur, relative to the total weight of nickel in the mixture; or about 0.4 wt % to about 1 wt % sulfur, relative to the total weight of nickel in the mixture.

The nickel particulate form readily forms a complex with one or more phosphorus-containing ligands; such a complex can be a useful hydrocyanation catalyst. The complex can include one or more phosphorus-containing ligands and nickel atoms from the nickel particulate form with any of the properties and features described herein. For example, one or more of the phosphorus ligands in the complex can be a ligand of Formula (III):

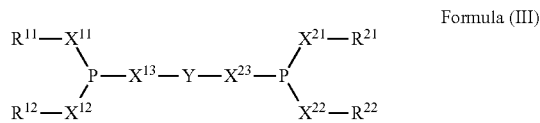

Formula (III)

wherein:

$X^{11}$, $X^{12}$, $X^{13}$, $X^{21}$, $X^{22}$ and $X^{23}$ independently represent oxygen or a single direct bond;

$R^{11}$ and $R^{12}$ independently represent identical or different, single or bridged organic radicals;

$R^{21}$ and $R^{22}$ independently represent identical or different, single or bridged organic radicals; and Y represents a bridging group.

Another useful phosphorus-containing ligand is the Ligand (V), which can be used in such a complex with nickel atoms:

Ligand (V)

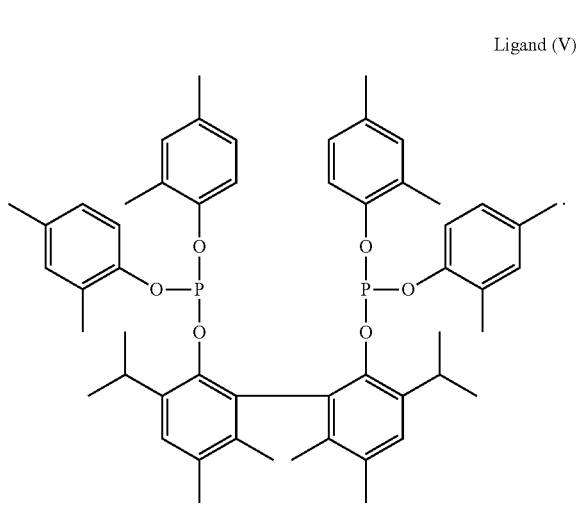

When the nickel atoms of the complex are from the nickel particulate form described herein an equilibrium of complex formation between Ligand (V) and nickel atoms from the nickel particulate form can be reached within about 2 hours (or even 1 hour, or even 30 minutes) when about 4 to 5 wt % of the nickel particulate form is mixed with 3-pentenenitrile containing approximately 5.25 wt % Ligand (V) and approximately 6300 ppm $ZnCl_2$. It may be advantageous to include sulfur in the nickel-phosphorus-containing ligand complex. For example, such complexes can have about 0.001 wt % to about 15 wt % sulfur, wherein the sulfur weight percentage is relative to the total weight of nickel in the mixture.

Such a complex between nickel atoms from the nickel particulate form described herein can have hydrocyanation catalytic activity. For example, the complex can have catalytic activity for hydrocyanation of a compound comprising at least one C=C bond.

The nickel particulate form can be in an organic liquid solution that includes one or more phosphorus-containing ligands, where the nickel particulate form has any of the properties or features described herein. The nickel particulate form can be suspended in the solution. Such a solution of claim can further include one or more pentenenitriles. For example, one or more pentenenitriles can be used as a solvent. The solution can also include a Lewis acid such as zinc chloride, ferrous chloride, or a combination thereof. The a complex can forms between one or more phosphorus-containing ligands and nickel atoms from the nickel particulate form within the solution. Such a solution can have hydrocyanation catalytic activity. For example, the solution can have catalytic activity for hydrocyanation of a compound that includes at least one C=C bond. Such a solution can also include about 0.001 wt % to about 15 wt % sulfur, wherein the sulfur weight percentage is relative to the total weight of nickel in the solution.

A complex between one or more bidentate phosphorus-containing ligands and nickel atoms from the nickel particulate form described herein can be made by a method that includes mixing an organic liquid solution that includes one or more bidentate phosphorus-containing ligands and the nickel particulate form with any of the properties or features described herein. Such a method can further include addition of a Lewis acid such as zinc chloride, ferrous chloride, or a combination thereof, within the organic liquid solution. The organic liquid solution can also include one or more nitriles. One example of a nitrile is a mononitrile. For example, the organic liquid solution can include one or more pentenenitriles. Such pentenenitriles can be used as a solvent. Such a method readily generates a complex formed between one or more bidentate phosphorus-containing ligands and nickel atoms from the nickel particulate form. The complexes formed by such a method can have catalytic activity for hydrocyanation of a compound comprising at least one C=C bond. It may be advantageous to include about 0.001 wt % to about 15 wt % sulfur in the organic liquid solution during such a method, wherein the sulfur weight percentage is relative to the total weight of nickel in the solution. The one or more of the phosphorus ligands can be a ligand of Formula (III) or Ligand (V), described herein.

The nickel particulate form described herein can be used in a method for hydrocyanating a compound having at least one C=C bond that involves contacting the compound with HC≡N in the presence of a catalyst comprising a zero-valent nickel complex with one or more phosphorus-containing ligands, wherein nickel atoms of the complex are from a nickel particulate form with any of the properties or features described herein. The one or more phosphorus-containing ligands can be a phosphite ligand, for example, a bidentate phosphite ligand such a ligand of Formula (III) or Ligand (V), described herein. The method can include an organic liquid solution that includes the complex and that can further include about 0.001 wt % to about 15 wt % sulfur, wherein the sulfur weight percentage is relative to the total weight of nickel in the solution.

Another aspect of the invention is a method of identifying whether a basic nickel carbonate test sample will yield a nickel particulate form with nickel atoms that complex with one or more phosphorus-containing ligands, that includes:
(a) calcining a basic nickel carbonate test sample; and
(b) observing whether the test sample gives off more or less carbon dioxide compared to a control basic nickel carbonate sample;
wherein the basic nickel carbonate test sample will yield an active nickel particulate form with nickel atoms that substantially complex with one or more phosphorus-containing ligands within about 2 hours, when the basic nickel carbonate test sample gives off less carbon dioxide than the control basic nickel carbonate; and
wherein the control basic nickel will yield a nickel particulate form with nickel atoms that substantially do not complex with one or more phosphorus-containing ligands within about 2 hours.

Such a method can be employed to avoid waste by allowing identification of a basic nickel carbonate test sample that gives off more carbon dioxide than the control basic nickel carbonate, and not using the basic nickel carbonate from which the basic nickel carbonate test sample was obtained to make a nickel particulate form for use in a hydrocyanation catalyst. Thus, poor sources of a basic nickel carbonate can be tested prior and waste can be avoided by not using such poor sources of a basic nickel carbonate to make large batches of nickel that may not form a useful catalyst complex with phosphorus-containing ligands. Instead, sources of basic nickel carbonate are identified that yield particulate nickel forms that readily complex with one or more phosphorus-containing ligands and useful hydrocyanation catalyst can be made.

Another aspect of the invention is a method of identifying whether a nickel test sample will yield a nickel particulate form with nickel atoms that complex with one or more phosphorus-containing ligands, comprising:

(a) reducing the nickel test sample with hydrogen; and
(b) observing whether the nickel test sample exhibits a single peak of hydrogen absorption between about 350° C. and 450° C. during reduction;
wherein the nickel test sample will yield an active nickel particulate form with nickel atoms that substantially complex with one or more phosphorus-containing ligands within about 2 hours, when the nickel test sample exhibits a single peak of hydrogen absorption between about 350° C. and 450° C. during reduction.

In such a method of claim the nickel test sample can be basic nickel carbonate, nickel oxide, nickel hydroxide, or a mixture thereof. Such a method can be used to avoid waste by identifying the nickel test sample(s) that exhibit two peaks of hydrogen absorption between about 300° C. and 450° C. during reduction, and not using a nickel source from which those nickel test sample(s) were obtained to generate a hydrocyanation catalyst. Instead, a source of a nickel test sample that exhibits one peaks of hydrogen absorption between about 300° C. and 450° C. during reduction can be used, because such a source will yield a nickel particulate form with nickel atoms that readily complex with one or more phosphorus-containing ligands to generate a useful hydrocyanation catalyst.

Another method for efficiently generating a complex between nickel atoms and one or more phosphorus-containing ligands a method can be employed that comprises:
(a) contacting:
  (i) a nickel starting material with a sulfur source, and generating nickel metal from the mixture of the nickel starting material and the sulfur source; or
  (ii) a nickel metal with a sulfur source; and
(b) contacting the nickel metal with one or more phosphorus-containing ligand(s) to thereby form a complex between nickel atoms from the nickel metal and one or more phosphorus-containing ligands.

The nickel metal in step (ii) can be simultaneously contacted with the sulfur source and one or more phosphorus-containing ligand(s). Thus, a hydrocyanation catalyst comprising a nickel-ligand complex can efficiently be formed in one step by simply mixing nickel metal (e.g., zero valent nickel), a sulfur source and one or more phosphorus-containing ligands.

Alternatively, a nickel starting material can be contacted with a sulfur source, and then processed to generate nickel metal. Examples of nickel starting materials that can be employed include basic nickel carbonate, nickel oxide, nickel salts or combinations thereof.

The sulfur source employed, for example, can be selected from the group consisting of elemental sulfur, polymeric sulfur, sulfur-containing salts, sulfur-containing ions and any combination thereof.

Another aspect of the invention is a catalyst preparation mixture comprising nickel metal, one or more phosphorus-containing ligands and about 0.0001 wt % to about 15 wt % sulfur, wherein the sulfur weight percentage is relative to the total weight of solids (mostly nickel metal) in the mixture.

Another aspect of the invention is a complex formed between nickel atoms and one or more phosphorus-containing ligands comprising about 0.00001 wt % to about 15 wt % sulfur, wherein the sulfur weight percentage is relative to the total weight of nickel in the complex.

It is surprising that sulfur treatment can improve the formation of nickel-ligand hydrocyanation catalysts because sulfur is reported to be a catalyst poison. See, e.g., Chen et al., IND. ENG. CHEM. RES. 27: 1391-96 (1988). Therefore, it is unexpectedly surprising that even sources of nickel metal that form nickel-ligand complexes poorly can be simply, effectively and efficiently converted into nickel metal preparations that form high levels of nickel-ligand complexes when the methods described herein are employed.

BRIEF DESCRIPTION OF THE FIGURES

FIG. 17A shows that BET SSA correlates with LD SSA for nickel preparations Ni1, Ni3, Ni6, Ni7, Ni8 and Ni9 (see Table 4). FIG. 17B shows a correlation between BET SSA and D10 particle sizes of samples Ni1, Ni3, Ni6, Ni7, Ni8 and Ni9 (Table 4). FIG. 17C graphically illustrates BET SSA values versus nickel activity for nickel samples Ni1-Ni6 and Ni9-Ni10 with the properties described in Table 4.

DETAILED DESCRIPTION OF THE INVENTION

Figure 1:
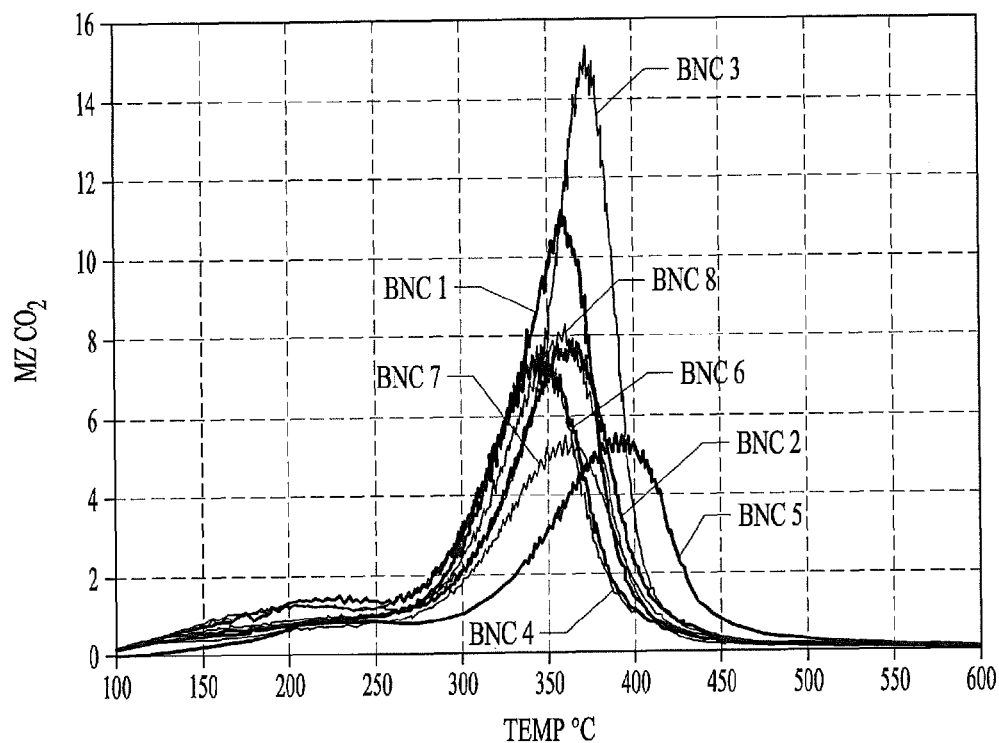
FIG. 1 shows carbon dioxide ($CO_2$) loss during calcination pre-treatment of the eight BNC samples #1-#8 listed in Table 2.

Nickel metal (e.g., zero valent nickel metal) particles are used to form complexes with one or more phosphorus-containing ligands, and the complex between nickel atoms and the phosphorus-containing ligands can be an effective hydrocyanation catalyst. These nickel-ligand complexes can be soluble in organic media, such as a hydrocyanation reaction milieu. As illustrated herein, treatment with a sulfur source improves the ability of a particulate nickel metal preparation to form complexes with one or more phosphorus-containing ligands.

The physical form as well as the content of sulfur in a preparation of particulate nickel metal affects its ability to form catalytic complexes with phosphorus-containing ligands. For example, nickel particulate forms with a BET Specific Surface Area of at least about 1 $m^2$/gm, and/or with a C10 value is less than about 20 nm after reduction at 300-400° C., and/or with an average crystallite size of no greater than about 100 nm exhibit good activity for forming a complex with phosphorus-containing ligands. However, sulfur treatment of nickel particulate forms having a lower BET surface area and/or a higher average crystallite size can dramatically improve the ability of those nickel particulate forms to complex with phosphorus-containing ligands. Combinations of desirable particulate nickel physical properties and sulfur concentrations provide optimal complex-formation activities.

Moreover, sulfur treatment of particulate nickel metal that poorly complexes with phosphorus-containing ligands can cure the defects in structurally inadequate nickel preparations to produce a nickel particulate form that readily complexes with phosphorus-containing ligands. To effect such treatment, sulfur sources can be added to a nickel starting material during manufacture of nickel metal particles, sulfur sources can be added directly to a mixture of particulate nickel metal and one or more phosphorus-containing ligands during nickel-ligand complex formation, or sulfur sources can be added directly to a hydrocyanation reaction mixture that contains a nickel-ligand catalyst.

Nickel particles treated with a sulfur source combine more effectively with one or more phosphorus-containing ligands and more efficiently generates an active hydrocyanation catalyst than does untreated nickel metal particles. The improvement in catalyst formation can be substantial. For example, after treatment of one commercially available source of nickel particles using the methods described herein the nickel exhibited a 14-15 fold improvement in complex formation with phosphorus containing ligands as measured, for example, by the solubility of the nickel-ligand complex in an organic medium. Prior to such treatment, that commercially available source of nickel was not useful for making nickel-ligand catalysts. Treatment with a sulfur source so dramatically improved complex formation by the nickel metal that a nickel source that otherwise may have been discarded could effectively be used to make excellent catalysts useful for manufacturing processes involving hydrocyanation.

The methods of generating active nickel hydrocyanation catalysts include contacting a nickel metal or a nickel starting material used to make nickel metal with a sulfur source. The nickel starting material can be contacted with the sulfur source during processing of the nickel starting material to generate nickel metal, or after nickel metal has been generated, or even during complex formation between the nickel metal and one or more phosphorus-containing ligand(s).

Desirable forms of nickel metal powder provided herein include particles of nickel metal composed of nickel crystallites having defined sizes, BET Specific Surface Areas and Laser Diffraction Specific Surface Areas, crystallite sizes, crystallite size distributions, surface crystallites per gram and combinations thereof. For example, desirable surface areas include those with BET Specific Surface Areas of at least about 1 $m^2$/gm, preferably at least about 2 $m^2$/g, more preferably at least 4 $m^2$/g, and further preferably at least 10 $m^2$/g. A desirable nickel particulate form can have at least one property selected from the group consisting of: a BET Specific Surface Area of at least about 1 $m^2$/gm; a BET Specific Surface Area/C50 ratio of not less than $0.07 \times 10^9$ m/gm; a C10 that is less than about 20 nm; an average crystallite size of no greater than about 30 nm; a crystallite size distribution span greater than about 1.0; on average at least about $10^{15}$ surface crystallites per gram of nickel; at least 10% of the particles of the form have a size (D10) of no greater than about 6 µm; a Laser Diffraction Specific Surface Area of at least about 0.4 m²/gm; a BET Specific Surface Area to D10 ratio of about $0.3 \times 10^6$ m/gm to about $10.0 \times 10^6$ m/gm; on average at least about $10^{16}$ surface crystallites per gram nickel that are smaller than or equal to size C10; and any combination thereof. Preferably the desirable nickel particulate form has at least two of these properties; more preferably, the desirable nickel particulate form has at least three of these properties; even more preferably, the desirable nickel particulate form has at least four of these properties.

Such desirable nickel particulate forms complex with Ligand (V) within about 2 hours when about 4 to 5 wt % of the nickel particulate form is mixed with 3-pentenenitrile containing Ligand (V) and $ZnCl_2$; wherein Ligand (V) has the following formula:

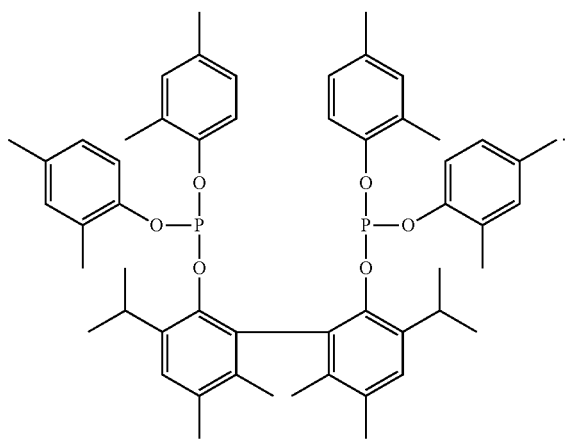

While such physical properties are desirable, treatment with a sulfur source can dramatically improve the ability of a particulate nickel form to complex with phosphorus-containing ligands. Thus, one or more desirable physical property can be lacking from a particulate nickel form if that particulate nickel form has been treated with a sulfur source during its preparation as a particulate metal or during complex formation of the particulate nickel metal form with one or more phosphorus-containing ligands.

Sulfur Sources

As described herein, nickel starting materials and nickel metals contacted with sulfur sources exhibit improved complex formation with phosphorus-containing ligands.

The sulfur source employed can include elemental sulfur, polymeric sulfur, sulfur-containing gases, sulfur-containing salts, sulfur-containing ions and combinations thereof. The sulfur source can be in liquid, solid, gaseous or a combination of such physical forms. The sulfur source can include, for example, sulfates, sulfites, sulfides, hyposulfites, thiosulfates, sulfur dioxide, sulfur monoxide, sulfur halides, and the like. Examples of sulfur sources that can be employed include hydrogen sulfide, nickel sulfate, nickel sulfite, nickel sulfide, nickel hyposulfite, nickel thiosulfate, sulfur trioxide, sulfur dioxide, sulfur monoxide, disulfur dichloride, sulfur dichloride, sulfur tetrachloride, sulfur chloride pentafluoride, disulfur decafluoride, sulfur hexafluoride, sulfur tetrafluoride, sulfur trifluoride and combinations thereof. Any of these and other sources of sulfur can be used to activate nickel for complex formation with phosphorus-containing ligands.

Elemental sulfur can be present in a number of forms, including solid elemental sulfur, gaseous sulfur, polymeric sulfur, mixtures of polymeric chains of sulfur, cyclic sulfur and combinations thereof. There are also a large number of allotropes of sulfur. The most common form found in nature is yellow orthorhombic α-sulfur, which contains puckered rings of eight sulfur atoms ($S_8$). In addition, other solid forms of sulfur contain sulfur rings of 6, 7, 9-15, 18 and 20 atoms. There are also sulfur gases, such as $S_2$, $S_3$, $S_4$, and $S_5$. Metallic-like sulfur forms can also be formed, for example, at high-pressures. Any and all of these forms of sulfur are sulfur sources for use in the methods described herein.

The sulfur source may be a sulfur-donor. Examples of sulfur donating compounds include thioethers, thioesters, disulfides and the like. For example, the disulfide can be selected from disulfides, thioacetic acid, thioacetate salts, polysulfides, bis-alkylamino disulfides, sulfenic sulfonic thioanhydrides, thiosulfonate salts, aminothiosulfonates, acylmethylmercapto azoles or azolium salts, thiazepines, thiepins, 1,4-dithiins, 1,2-, 1,3-, or 1,4-thiazines, 1,4,2-dithiazines, 1,3,4-, 1,2,6-, 1,3,5-thiadiazines, dihydro derivatives of dithiazines or thiadiazines, 1,2,3,4-thiatriazoles and combinations thereof. Vulcanizing agents such as those discussed by Porter, M. in Vulcanization of Rubber; Oae, S. Ed.; Organic Chemistry of Sulfur; Plenum: New York, 1977, Chapter 3, and by Hofmann, W. Vulcanization and Vulcanizing Agents; Palmerton: New York, 1967 may also be effective.

It may be preferable that the sources of sulfur not introduce organic compounds or organic moieties to the nickel preparations or the mixtures of nickel and phosphorus-containing ligands. For example, the sulfur source may not include carbon-containing or phosphate-containing compounds and moieties. Sources of sulfur may not include metal contaminants (other than nickel). For example, sources of sulfur may not include substantial amounts of alkali and alkaline earth ions or salts. In some instances such organic compounds or moieties can be removed during processing of a mixture of the sulfur source and a nickel starting material. For example, calcination and/or reduction processes used to generate nickel metal particles from nickel starting materials may remove some organic compounds or moieties.

Accordingly, a variety of sulfur sources can be employed to improve nickel activity. Sulfur sources with proven ability to transform nickel starting materials into nickel particulate forms with good nickel-ligand complex formation properties include liquid or solid nickel sulfate, elemental sulfur (e.g., $S_8$), and nickel sulfide (e.g., $Ni_3S_2$).

Such nickel sources can be added to a nickel starting material (e.g., basic nickel carbonate or nickel oxide) during manufacture of nickel metal particles, the sulfur source can be added directly to a mixture of particulate nickel metal and one or more phosphorus-containing ligands during nickel-ligand complex formation, or the sulfur source can be added directly to a hydrocyanation reaction mixture that contains a nickel-ligand catalyst.

Nickel Starting Materials

Nickel metal (e.g., zero valent nickel metal) can be directly treated with a sulfur source before, during or after complex formation with phosphorus-containing ligands. However, a nickel starting material can also be contacted with a sulfur source, where the nickel starting material is processed to generate nickel metal. For example, the nickel starting material can include higher valent nickel in salt form. Thus, the sulfur source can be added to a nickel starting material prior to reduction of the nickel starting material to make nickel metal particles.

Many sources of nickel are available and can act as starting materials to prepare nickel metal. For example, the nickel starting material can be basic nickel carbonate, nickel carbonate, nickel bicarbonate, nickel oxalate, nickel formate, nickel squarate, nickel hydroxide, nickel oxide, nickel salts, or a combination thereof.

Different types of nickel starting materials may require different processes to generate nickel metal. Processes for generating nickel metal are available in the art and examples of such processes are described herein. Surprisingly, treatment of nickel starting materials with a sulfur source can occur at essentially any stage of the nickel metal preparation process. Typically, a process for generating nickel metal includes reduction of a higher valent form of nickel into zero valent nickel metal. Addition of a sulfur source prior to reduction of a nickel starting material is a good way to form nickel metal particles that effectively complex with phosphorus-containing ligands.

Nickel oxide is also a convenient nickel starting material. The nickel oxide is preferably in particulate form. To generate particulate nickel metal for making nickel-ligand complexes, the nickel oxide is reduced from valent state+2 to zero valent nickel metal particles. Such reduction can be performed as described herein or by other available procedures.

As illustrated herein, even after reduction, many commercially available sources of nickel oxide do not form useful catalysts after reduction and combination with phosphorus-containing ligands. However, when such nickel oxide is treated with a sulfur source before, during or after reduction, the nickel formed can readily complex with phosphorus-containing ligands to a greater extent than does the nickel generated from nickel oxide prior to treatment with the sulfur source.

Basic nickel carbonate is another useful nickel starting material. Basic nickel carbonate is commercially available or it can be made as described herein. When basic nickel carbonate is employed as a starting material it is reduced to generate nickel metal. Optionally, the basic nickel carbonate can be calcined prior to reduction, thereby driving off carbon dioxide and providing a nickel oxide composition. Such a calcination step has been used to increase reactivity of the nickel sample with respect to formation of nickel-ligand complexes soluble in organonitrile solvents. However, when treated with a sulfur source as described herein, it may not be necessary to calcine the basic nickel carbonate to achieve satisfactory levels of nickel-ligand complex formation. However, if calcination is performed, the basic nickel carbonate can be contacted with a sulfur source during calcination to produce nickel oxide, during reduction to generate nickel metal or during complex formation of the nickel metal product with phosphorus-containing ligands.

As illustrated herein, even after calcination and reduction, many commercial sources of basic nickel carbonate do not readily form complexes with phosphorus-containing ligands. However, when such commercial sources of basic nickel carbonate are treated with a sulfur source before, during or after calcination and/or reduction, even these commercial sources of basic nickel carbonate can be transformed into nickel metal preparations that readily complex with phosphorus containing ligands.

Nickel formate can also be employed as a starting material useful for preparing nickel metal particles. As illustrated herein, nickel formate can be thermally treated to generate nickel metal particles useful for complex formation with phosphorus-containing ligands, especially when sulfur is present (e.g., more than about 500 ppm sulfur, preferably about 0.2 wt % to about 15 wt % sulfur). Thus, nickel formate can simply be thermally treated in a non-oxygen containing gas such as nitrogen, and it may not be necessary to subject nickel formate to a reduction step.

When nickel formate is thermally treated to generate nickel metal particles, the nickel formate can be heated to 350° C. to 450° C. in a non-oxygen atmosphere for about 1 to 4 hours. As illustrated herein, nickel formate can conveniently be thermally treated in a fluidized bed reactor where it is suspended in a nitrogen atmosphere and heated to about 400° C. for about 2 hours.

While reduction of nickel formate may not be necessary, such reduction can be performed using procedures described herein or available in the art. If calcination is desired, nickel formate can also be calcined using methods described herein. Thus, the nickel formate thermally treated in a non-oxygen atmosphere, the nickel formate can be reduced without calcination pre-treatment or it can be subjected to calcination pre-treatment followed by reduction to zero valent nickel metal particles. The sulfur source can be combined with nickel formate at any step (thermal treatment, calcination, reduction or complex formation) to generate a nickel-phosphorus ligand complex with catalytic activity.

Another nickel starting material useful for preparing nickel metal particles that can readily complex with phosphorus-containing ligands is a nickel salt. One example of a useful nickel salt for making nickel metal particles is nickel sulfate. When nickel sulfate is employed as a starting material for making nickel metal there may be no need for further sulfur treatment because the sulfate is an excellent source of sulfur. Therefore, nickel sulfate can be a useful starting material for generating nickel metal.

Nickel sulfate can be in solid (e.g., particulate) form or be in solution. When nickel sulfate is in solution, the solvent can be removed to generate a nickel(II)-containing powder. In general, the nickel sulfate is subjected to calcination to generate nickel oxide with sulfate ions, prior to reduction. Calcination of nickel sulfate reduces the probability that large amounts of $Ni_3S_2$ will be formed during reduction, which may not complex well with phosphorus-containing ligands. The nickel (e.g., $Ni^{+2}$ and nickel oxide) in the solid and powdered materials formed by calcination of nickel sulfate are reduced to generate nickel metal (zero valent nickel) using the methods described herein or other available procedures.

Nickel metal can also be treated with a sulfur source. As illustrated herein, commercially available sources of nickel exhibit variable, unpredictable and typically poor activity for making nickel-ligand complexes as hydrocyanation catalysts. However, an active particulate nickel metal that readily reacts with phosphorus-containing ligands can readily be produced by adding the sulfur source to nickel metal particles. For example, a sulfur source can be added to a mixture of nickel particles and phosphorus-containing ligands in a convenient solvent (e.g., an organonitrile solvent) to generate nickel-ligand complexes that are effective hydrocyanation catalysts. The sulfur source can also be added to a hydrocyanation reaction mixture that contains a nickel-phosphorus ligand catalyst.

In general, untreated nickel metal from commercial sources exhibits poor complex formation with phosphorus containing ligands. While reduction of commercially available nickel metal may provide a slight improvement, addition of a sulfur source during nickel reduction, or simply during formation of the hydrocyanation catalyst, reliably transforms poor nickel metal sources into a form of nickel metal that efficiently combines with phosphorus-containing ligands to generate useful hydrocyanation catalysts.

When nickel metal is selected for treatment with a sulfur source, the nickel metal can be a particulate (powdered), zero valent nickel metal. If the nickel metal is partially oxidized it can be reduced by procedures available in the art, for example, by thermal hydrogen treatment as described herein.

Treatment with Sulfur Sources

Nickel metal particles and nickel starting materials can be treated with varying amounts of a sulfur source at different stages of producing zero valent nickel metal, forming a nickel-ligand complex and maintaining an effective nickel-ligand catalyst during hydrocyanation reactions. For example, sulfur sources can be added to nickel starting materials before, during or after calcination. Sulfur sources can be added to nickel starting materials before, during or after reduction. A sulfur source can also be included during nickel-ligand complex formation and during hydrocyanation reactions that employ nickel-ligand catalysts.

The nickel starting materials or the nickel metal can be in solution, in suspension or in particulate form during treatment with a sulfur source. For example, the nickel can be in particulate form within a liquid medium or within a gas stream. Thus, the nickel starting materials or nickel metal can be in suspension. The solubility of nickel metal is generally quite low in many liquid solvents. However nickel metal can be suspended in a liquid or by a gas. Alternatively, the nickel starting materials or nickel metal in solid particulate form can simply be mixed with the sulfur source.

The sulfur source can be combined and/or mixed with the nickel starting materials or nickel metal for varying times. For example, the nickel starting materials or nickel metal and a sulfur source can be mixed together for about 1 minute to about 72 hours, or about 1 minute to 24 hours, or about 1 minute to 12 hours, or about 1 minute to 4 hours, or about 1 minute to 2 hours, or about 1 minute to 1 hour. Little mixing may initially be needed when the sulfur source is added to a nickel starting material that is subjected to further processes involving mixing, such as calcination, reduction or even catalyst complex formation.

During treatment of nickel starting materials or nickel metal with a sulfur source, the mixture can be maintained at about 4° C. to about 450° C. Little or no additional heating or incubation may be needed to treat nickel metal or nickel starting materials with a sulfur source because various steps in the formation of nickel metal or the formation of a nickel-ligand catalyst complex provide sufficient heating and mixing for sulfur treatment of nickel. Thus, sulfur sources can be added to essentially any convenient step involved in the preparation of nickel metal or nickel-ligand complexes.

For example, a sulfur source can be added directly to a catalyst complex formation mixture that contains nickel metal particles and phosphorus-containing ligand(s) in an organic solvent (e.g., an organonitrile solvent) that is mixed and warmed to about 60° C.-80° C. A sulfur source can conveniently be added to any nickel starting material and the nickel starting material can be processed in the usual manner into particulate nickel metal, for example, by reduction (calcination is typically optional).

Nickel and nickel starting materials can effectively be treated with varying amounts of a sulfur source. For example, a molar ratio of sulfur to nickel can range from about 0.003 to about 1.8; preferably the molar ratio is about 0.004 to about 0.2; and more preferably such a sulfur to nickel molar ratio is about 0.01 to about 0.05.

Effective amounts of sulfur in combination with nickel and nickel starting materials can vary from about 0.1 wt % sulfur to about 50 wt % sulfur relative to the total weight of the composition, or preferably from about 0.2 wt % to about 4 wt % sulfur relative to the total weight of the composition, preferably from about 0.3% to about 2 wt % sulfur relative to the total weight of the composition.

For example, effective amounts of sulfur in a zero valent particulate nickel preparation can vary from about 0.1 wt % sulfur to about 50 wt % sulfur relative to the weight of nickel. The weight percentage of sulfur can vary from about 0.2 wt % sulfur to about 15 wt % sulfur, or about 0.2 wt % sulfur to about 10 wt % sulfur. Preferably, the amount of sulfur in a zero valent particulate nickel preparation can be about 0.5 wt % sulfur to about 5 wt % sulfur relative to the weight of nickel, or more preferably from about 0.6% to about 1% sulfur relative to the weight of nickel. As illustrated herein, an effective amount of sulfur in a particulate nickel metal preparation is about 0.8% sulfur relative to the weight of nickel.

Nickel starting materials such as basic nickel carbonate, nickel carbonate, nickel bicarbonate, nickel oxalate, nickel formate, nickel squarate or combinations thereof can be treated with about 0.1 wt % to about 25 wt % sulfur relative to the total weight of the composition, or about 0.2 wt % to about 10 wt % sulfur relative to the total weight of the composition, about 0.3 wt % to about 3 wt % sulfur relative to the total weight of the composition. Preferably, such nickel starting materials are treated with a source of sulfur ranging from about 0.3 wt % to about 1 wt % sulfur relative to the total weight of the composition, or about 0.3 wt % to about 0.5 wt % sulfur relative to the total weight of the composition. As is illustrated herein, an effective amount of sulfur in basic nickel carbonate is about 0.4 wt % sulfur relative to the total weight of the composition. Similar nickel starting materials can be treated with about 0.4 wt % sulfur relative to the total weight of the composition.

Nickel starting materials such as basic nickel carbonate (BNC), nickel carbonate, nickel bicarbonate, nickel formate, nickel oxalate or nickel squarate can be mixed with a sulfur source so that the sulfur content is at least 0.1% by weight on nickel basis, or at least 0.2% by weight on nickel basis, or at least 0.3% by weight on nickel basis, or at least 0.4% by weight on nickel basis, or at least 0.5% by weight on nickel basis, or at least 0.6% by weight on nickel basis, or at least 0.7% by weight on nickel basis, or at least 0.8% by weight on nickel basis, or at least 0.9% by weight on nickel basis, or at least 1.0% by weight on nickel basis, or at least 2% by weight on nickel basis, or at least 3.0% by weight on nickel basis.

Somewhat more sulfur may be used to treat nickel oxide than basic nickel carbonate. For example, nickel oxide can be treated with about 0.2 wt % to about 30 wt % sulfur relative to the total weight of the composition, or about 0.3 wt % to about 10 wt % sulfur relative to the total weight of the composition, about 0.4 wt % to about 5 wt % sulfur relative to the total weight of the composition. Preferably, nickel oxide is treated with about 0.4 wt % to about 1 wt % sulfur relative to the total weight of the composition, or about 0.5 wt % to about 0.7 wt % sulfur relative to the total weight of the composition. As is illustrated herein, an effective amount of sulfur in a mixture with nickel oxide is about 0.6% sulfur relative to the total weight of the composition. Similar nickel starting materials can be treated with about 0.6% sulfur relative to the total weight of the composition.

Nickel oxide with a sulfur source so that the sulfur content is at least 0.2% by weight on nickel basis, or at least 0.3% by weight on nickel basis, or at least 0.4% by weight on nickel basis, or at least 0.5% by weight on nickel basis, or at least 0.6% by weight on nickel basis, or at least 0.7% by weight on nickel basis, or at least 0.8% by weight on nickel basis, or at least 0.9% by weight on nickel basis, or at least 1.0% by weight on nickel basis, or at least 2% by weight on nickel basis, or at least 3.0% by weight on nickel basis.

When sulfur containing salts are used a source of sulfur, the sulfur containing salts can be contacted with the nickel starting materials or nickel metal as a solid or as an aqueous solution. Where the salt is used as an aqueous solution, the concentration of the solution may be from about 0.01M to about 2 M, or from about 0.05 M to about 1.5 M, or from about 0.1 M to about 1.5 M, or the concentration may be 1M. For example, NiSO$_4$ may be used as 1M aqueous solution. A weight ratio of about 1:2 to about 1:8 nickel starting material to 1M sulfur salt solution can be employed for effective treatment of the nickel starting material. For example, as illustrated herein, a 1:5 weight ratio of basic nickel carbonate to a 0.05 to 1M nickel sulfate solution can be employed to generate a particulate nickel metal preparation (after drying and reduction) that efficiently forms a complex with one or more phosphorus-containing ligands. Testing demonstrates that a 1:5 weight ratio of nickel starting material 1M nickel sulfate solution can be employed for several types of nickel starting materials such as basic nickel carbonate, nickel oxide and passivated (NiO coated) nickel.

Also as illustrated herein, about 0.4% to 2% elemental sulfur or nickel sulfide (on a wt % sulfur basis relative to the total composition) can be added to basic nickel carbonate or nickel oxide to form particulate nickel metal preparations (after reduction) that effectively combine with phosphorus-containing ligands to form nickel-ligand complexes.

The nickel starting materials containing the sulfur can be reduced to make particulate zero valent nickel metal for use in a catalyst. Calcination is typically optional, however, if nickel sulfate is used as a nickel starting material, it may be desirable to calcine the nickel sulfate before reduction.

When the nickel to be contacted with sulfur is zero valent particulate nickel metal, the sulfur source can be added directly to a catalyst preparation mixture that contains the particulate nickel metal and phosphorus-containing ligand(s) in a solvent. A Lewis acid (e.g., zinc chloride) is generally also present in the catalyst preparation mixture. Such a Lewis acid can facilitate complex formation. The amount of sulfur source employed compared to nickel can vary so that about 0.1 wt % sulfur to about 50 wt % sulfur, or about 0.2 wt % sulfur to about 25 wt % sulfur, or from about 0.5 wt % sulfur to about 15 wt % sulfur is employed relative to the amount of nickel. As illustrated herein addition of as little as 150 ppm elemental sulfur or nickel sulfate to a catalyst preparation mixture improved nickel-ligand complex formation by about 3- to 5-fold. Addition of about 11% to 12% S$_8$ (relative to the nickel content) to a catalyst preparation mixture improved nickel-ligand complex formation by about 4- to about 12-fold.

Thus, methods of effective treatment of nickel with sulfur sources are simple, flexible and easily implemented.

Preparing Nickel Starting Materials

Particulate nickel metal can be obtained from a higher valent nickel starting material such as a Ni(II) containing starting material. Examples of nickel starting materials include basic nickel carbonate, nickel carbonate, nickel bicarbonate, nickel oxalate, nickel fotinate, nickel squarate, nickel hydroxide, nickel oxide, nickel salts or a combination thereof. One frequently employed example of a higher valent nickel starting material is a nickel salt such as basic nickel carbonate, also referred to as BNC or BNC nickel. BNC can be used in the methods described below to produce an inventive Ni metal particulate form.

Basic nickel carbonate is available commercially. For example, basic nickel carbonate can be obtained by MetChem Corporation, an American distributor of this material. According to the vendor, the basic nickel carbonate provided is produced by precipitating the basic nickel carbonate from an aqueous solution comprising nickel, ammonia, ammonium carbonate, and water. According to the vendor, the basic nickel carbonate is produced from an ore comprising nickel and the basic nickel carbonate and may further comprise at least one element selected from the group consisting of aluminum, calcium, cobalt, copper, iron, magnesium, manganese, sodium, sulfur, and zinc. For example, analysis of MetChem basic nickel carbonate as received from the supplier indicates that it has composition shown in Table 1.

TABLE 1

Analytical Results for MetChem Basic Nickel Carbonate Powder Nickel 47% by weight

| Cobalt 65 ppm | Copper 20 ppm | Iron 55 ppm | Zinc 12 ppm |
| Magnesium 60 ppm | Calcium 60 ppm | Sodium 60 ppm | Sulfur 175 ppm |

Without sulfur treatment, basic nickel carbonate obtained from MetChem typically does not form nickel metals that complex with phosphorus containing ligands at a commercially acceptable rate (e.g., within a few minutes to a few hours). However, when MetChem basic nickel carbonate is treated with a sulfur source during nickel metal preparation or during complex formation, the nickel metal derived from MetChem basic nickel carbonate does form complexes with phosphorus containing ligands within a commercially acceptable time period (e.g., within about 15 minutes to about 3 hours).

It may be desirable to manufacture the basic nickel carbonate rather than obtaining it from a commercial source. For example, impurities may be avoided and the composition of the basic nickel carbonate can be controlled by manufacture of the basic nickel carbonate using selected reactants and manufacturing conditions.

BNC can be described with a chemical formula of

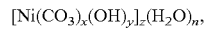
$$[Ni(CO_3)_x(OH)_y]_z(H_2O)_n,$$

wherein x=z−(y/2); y=2z−2x; z=1 to 100; and n=0 to 400. BNC can include nickel(II) ions, carbonate ions, hydroxide ions, and water molecules. BNC can be synthesized using available procedures.

The selected BNC nickel starting material can have low carbonate content. For example, a selected BNC nickel starting material can have a molar ratio of NiCO$_3$:Ni(OH)$_2$ less than approximately 1, with a mass ratio of Ni:C of at least about 10:1, or any combination thereof. Such BNC can produce Ni(0) with low levels of carbon impurities, including low levels of carbon impurities such as carbonate impurities.

Preparation of particulate nickel metal from BNC nickel that has a low carbonate content, such as a molar ratio of NiCO$_3$:Ni(OH)$_2$ less than approximately 1, a mass ratio of Ni:C of at least about 10:1, or any combination thereof, can more readily produce CO$_2$ during calcination and thus can result in more complete conversion to NiO, with fewer carbon impurities in the NiO. By producing NiO with a lower carbon content, including a lower carbonate content, less carbon impurities can be present in the Ni(0) product, the Ni(0) product can be more "active" as defined herein, or both.

BNC can be made by (i) contacting a precipitant solution and a nickel solution in a precipitation reactor to form a reaction mixture; and (ii) precipitating the nickel salt from the reaction mixture, wherein the nickel solution comprises nickel(II) ions and water, and the precipitant solution is selected from the group consisting of: (a) bicarbonate ions and water, (b) carbonate ions and water, and (c) mixtures thereof.

The mole ratio of bicarbonate ions to nickel(II) ions in the reaction mixture at the conclusion of the feeding can range from 0:1 to 2:1, including from about 0:1 to about 1.6:1, from about 0:1 to about 1.2:1, from about 1.0:0 to about 1.9:1, from about 1.2:1 to about 1.9:1, from about 0.8:1 to about 1.4:1, from about 1.0:1 to about 1.8:1, from about 1.0:1 to about 1.6:1, from about 1.0:1 to about 1.4:1, from about 0.8:1 to about 1.4:1, and from about 0.8:1 to about 1.2:1. The mole ratio of carbonate ions to nickel ions in the reaction mixture at the conclusion of the feeding can range from 0:1 to 1.6:1, including from about 0:1 to about 1.4:1, from about 1.0:0 to about 1.2:1, from about 0.8:1 to about 1.4:1, from about 1.0:1 to about 1.6:1, from about 1.0:1 to about 1.6:1, from about 1.0:1 to about 1.4:1, from about 0.8:1 to about 1.4:1, and from about 0.8:1 to about 1.2:1. Blends of bicarbonates and carbonates can also be used in the precipitant solution.

A precipitation reactor used for preparing precursor BNC samples can be any suitable containment vessel such as a tank, vessel or pipe. The precipitation of the BNC can be performed in a batch or continuous fashion. The reaction mixture can be agitated prior to and/or during the precipitation of the nickel composition. For example, agitation can be done by mechanical stirring, pumped circulation loop, flow-through static mixture, or ultrasound. The use of high sheer during precipitation can prevent particle agglomeration and can give smaller resulting BNC particles. Reactor designs, stirring designs, and the application of high amounts of power to stirring are examples of factors that can cause a high-sheer stirring of the reaction mixture during precipitation.

The BNC can be precipitated from the reaction mixture in the presence of added carbon dioxide. For example, the carbon dioxide can be added to the precipitation reactor, added to the nickel solution, added to the precipitant solution, added to the reaction mixture, and any combination thereof. While not to limit the invention by a recitation of theory, adding carbon dioxide may change the sulfur content of the BNC by indirectly influencing the neutralization stoichiometry. Also, the precipitant solution can be fed to the precipitation reactor over a period of time such as about 30 minutes to about 60 minutes, and such addition can be performed in a semi-continuous or continuous manner. The precipitant solution can also be added to the nickel solution in the precipitation reactor in a semi-continuous or continuous manner, for example, by using gradual addition.

The BNC can be precipitated within a temperature range of from about 0° C. to about 90° C., including from about 20° C. to about 90° C., from about 20° C. to about 70° C., from about 20° C. to about 50° C., from about 50° C. to about 90° C., from about 60° C. to about 80° C., and from about 65° C. to about 75° C. Increased temperature during precipitation may decrease the proportion of carbonate ions in the resulting BNC, which may be useful for generating useful hydrogenation catalysts.

The use of a higher pH during precipitation can decrease the proportion of carbonate ions in the resulting BNC precipitate. For example, a pH value of about 4, 5, 6, 7, 8, or about 9, or higher may be used. In one example, the pH increases from about 4.9 to about 5.8 during the precipitation.

The reaction mixture can also be digested after contacting the precipitant solution to the nickel solution by heating the reaction mixture from between about 50° C. and about 90° C. for a period of from about 0.25 hours to about 24 hours. Precipitation can occur before, during, or after digestion, or any combination thereof. Other suitable temperature ranges include from about 60° C. to about 80° C., and/or from about 65° C. to about 75° C. Other suitable digestion time periods can range from about 2 hours to about 24 hours, including from about 4 hours to about 20 hours, from about 6 hours to about 16 hours, and from about 8 hours to about 12 hours. Longer digestion times can cause larger BNC particles in the resulting precipitate.

The BNC preparation methods can also include, after the precipitation step, washing the precipitated BNC with water; and partially drying the precipitated BNC. For example, the precipitated BNC can be separated from the reaction mixture by filtration or decantation, the resulting precipitated BNC can be washed with water by filtration or decantation, and/or the resulting BNC can be dried by water evaporation between 60° C. and 100° C. Drying can be performed under ambient pressure or under vacuum, and in the presence of an inert gas such as nitrogen.

A nickel solution used in preparation of the BNC, comprising nickel(II) ions and water, may be prepared by dissolving a nickel(II) salt in water. The nickel salt can be any salt that is soluble in water, for example $NiCl_2$, $NiSO_4$, and $Ni(NO_3)_2$. Alternatively, a commercial BNC can be repurified, by first dissolving the crude BNC in an aqueous acid such as hydrochloric, sulfuric, or nitric acid, then using that solution for reprecipitation of purified BNC as described herein. Other water-insoluble Ni(II) sources can be converted to a soluble material in a similar manner and used as a source of BNC suitable for preparation of nickel active particulate forms of the invention.

The precipitant solution, comprising bicarbonate ions, can be prepared by dissolving a bicarbonate salt, for example, $NaHCO_3$ and $NH_4HCO_3$, in water. Alternatively, the precipitant solution can be prepared in-situ by dissolving $CO_2$ and an alkali metal hydroxide or ammonia in water by known methods. Likewise, the precipitant solution, comprising carbonate ions, can be prepared by dissolving a carbonate salt, for example $Na_2CO_3$. The precipitant solution can also be prepared in-situ by dissolving $CO_2$ and an alkali metal hydroxide in water by known methods. The anion of the nickel salt and cation of the bicarbonate or carbonate salt may be selected such that a salt produced from the precipitation, comprising both the cation and anion from the reaction mixture (for example NaCl), is soluble in the water of the reaction mixture. Such a selection provides a method for separating the anions and cations from the precipitated BNC.

As previously stated, the amount of bicarbonate or carbonate ions relative to the nickel(II) ions charged to make BNC, can affect the nickel reactivity of the resulting zero-valent nickel particles with the phosphorus-containing ligand, e.g., ligand (V). Because of the high costs of nickel, producers of BNC-type nickel compositions would be led to add excess amounts of the precipitant solution so as to recover as much of the nickel as economically feasible. However, it has surprisingly been found that the use of excess precipitant produces nickel metal of low reactivity for the phosphorous-ligand complex reaction. Highly reactive nickel is produced when reduced levels of precipitant are used, where presumably more of the nickel(II) ions are allowed to remain dissolved in the water of the resulting reaction mixture and may not be precipitated.

It has also been found that the precipitated nickel composition made using bicarbonate ions filters and surprisingly washes much faster than the precipitated nickel composition made using carbonate ions. In addition, the filtered precipitated nickel composition made using bicarbonate ions dries to a soft powder with little shrinkage. For these reasons, producing the nickel-containing solid using bicarbonate ions provides further desirable properties for downstream processing and handling of the dried precipitated nickel BNC composition.

Reduction of Nickel-Containing Materials

Generation of nickel metal can include direct reduction of certain nickel starting materials or reduction of nickel metal preparations. However, the extent of nickel reduction is typically not critical. Suitable nickel metal preparations include those that are fully reduced or partially reduced. The degree of reduction can readily be determined and selected by one of skill in the art using procedures described herein or available in the art.

A variety of nickel starting materials can be reduced such as BNC, nickel squarate, nickel oxalate, nickel sulfate, nickel oxide, nickel oxalate, and partially oxidized nickel metal, or nickel metal. In general, such nickel starting materials and/or nickel metals can be reduced with a reductant (e.g., hydrogen, methane, CO) at elevated temperatures.

The nickel starting materials can be calcined prior to reduction or they can be directly reduced with hydrogen or another reductant at elevated temperatures. Calcination can remove absorbed gases such a carbon dioxide, sulfur dioxide, and the like.

As described herein, a sulfur source can be mixed with the nickel metal or nickel starting materials during the reduction process.

Reduction can be performed in a convenient reduction or reactor vessel, such as a fluid bed reactor, an expanded fixed bed, a rotary kiln, a rotary pan or any such equipment known to the skilled person. To facilitate optimal exposure of nickel metal and/or nickel starting materials to the reductant, a fluidized bed reduction vessel can be employed.

For example, a fluidizing bed reactor can be employed to perform both calcination and reduction of the nickel starting materials and/or nickel metals to zero valent nickel metal powder. The nickel starting materials and/or nickel metal can be charged to a fluidizing bed reactor and the reactor can be closed. The reduction (and/or calcination) procedure can then be initiated. For the reduction process, the reactor can be flushed with an inert gas to remove oxygen from the reactor prior to introducing the reductant.

During reduction, steam can also be a component of the mixture of reductant. When steam is used such as during the reduction process, the nickel metal powder so generated can be free-flowing, which facilitates product removal from the reaction vessel and further processing of the nickel metal. Steam is not necessary under most conditions for producing a reactive nickel metal product but it does prevent agglomeration and clumping of the reduced nickel product.

For reduction to zero-valent nickel metal, the gas flowing through a bed of the nickel starting material or nickel metal contains a reductant, preferably in an inert carrier gas. The reductant can be any gaseous or particulate substance that can reduce nickel ions to nickel metal. Examples of reductants that can reduce nickel ions to nickel metal include, for example, hydrogen, methane, and carbon monoxide. A desirable reductant is hydrogen. For example, the fluidization gas can contain hydrogen in amounts sufficient to reduce at least a portion of the nickel in the fluidized nickel-containing material to nickel metal. Gas flow rate during the process can be determined by the type of equipment used for the reduction and is within the knowledge of the skilled person to choose.

The inert carrier gas is essentially free of oxygen. Examples of inert carrier gases that can be employed include nitrogen, argon and neon. Nitrogen is an inexpensive and convenient source of an inert carrier gas.

The gas or mixture of gases used for reduction can also contain steam, which can facilitate generation of a free-flowing nickel metal product. Steam is not necessary under most conditions for producing a reactive nickel metal product but it does prevent agglomeration and clumping of the reduced nickel product thereby facilitating product removal from the reduction vessel and further processing of the nickel metal. The percentage of steam in the reducing gas can be about 0.1% to 80% by volume, or about 0.1% to 70% by volume, or about 0.1% to 50% by volume, or from about 0.1% to 30% by volume. The fluidization gas can contain about 0.1% to 20% volume percent steam, or about 1% to about 20% volume percent steam. The presence of water vapor in the form of steam is effective in producing a free flowing nickel powder.

Conditions sufficient to reduce nickel starting materials and/or nickel metal to zero-valent nickel metal include an elevated temperature and both an amount of reducing agent (e.g., hydrogen gas) and a time sufficient to substantially reduce the nickel containing solids to form a third nickel-containing solid that comprises nickel metal.

The reducing step is advantageously performed at a temperature between 200° C. and 500° C., for example, between 200° C. and 450° C., or between 225° C. and 425° C., or between 250° C. and 400° C. Temperatures at the lower end of these ranges (e.g., 200° C. and lower) require longer reduction times. Reductions at high temperatures (e.g., 500° C. and higher) can give nickel metal powders with reduced complex formation with phosphorus containing ligands.

The time for reduction can vary somewhat with temperature, with reduction proceeding somewhat faster at higher temperatures. In general, reduction is performed for about 30 minutes to 8 hours, preferably for about 1 to 6 hours, more preferably for about 2 to 5 hours and most preferably for about 4 hours.

It is observed that for temperatures of about 300° C. and 475° C. or about 250° C. and 400° C. the reduction step is substantially complete in about four hours, provided that at least one equivalent of hydrogen is reacted with nickel oxide. It can be desirable to add an excess of hydrogen (e.g., more than one equivalent), to ensure complete reduction. The range of temperatures that can be employed is therefore affected by the time of reduction and the amount of hydrogen provided. An acceptable temperature range includes any numerical range of integers representing a temperature range falling between 200° C. and 500° C. However, preferred temperatures are about 250° C. to 400° C., or about 250° C. and 350° C. for about four hours.

When the hydrogen is used as the reducing agent, introduction of hydrogen to the fluidization reaction vessel can cause an immediate temperature increase in the bed of nickel-containing solids, for example, of about 10-50° C. depending on the concentration of hydrogen. Those of skill in the art are aware that such an increase can occur and can adjust the reduction conditions as desired.

In general, sufficient reducing agent (e.g., hydrogen) is passed through the reactor to convert the nickel containing solids to nickel metal powder. An effective steam concentration in the reducing gas can be from about 1% to about 80% by volume. For example, an effective hydrogen concentration can be from about 10% to about 95% by volume. A carrier gas can be present in concentrations of about 20% to about 85% by volume. An example of a gas composition effective for reduction comprises about 10-20% steam, about 10-20% hydrogen, and the remainder as nitrogen, by volume percent (volumetric measurement).

Reactor pressure during the reduction step is not critical. Thus, reduction can be performed at a pressure of about 0.1 atmospheres to 20 atmospheres, or about 0.5 atmospheres to 10 atmospheres, or about 0.5 atmospheres to 2 atmospheres. The reduction can conveniently be performed at about one atmosphere pressure.

At the end of the reduction step, the reactor is filled with nitrogen, or another inert gas effective to remove residual hydrogen. The inert gas is selected to be nonreactive with the nickel metal powder. Oxygen contact with the nickel metal at this stage can oxidize at least the surface of a nickel particle to nickel oxide, potentially lowering reactivity in the catalyst formation step.

Prior to reduction, the fluidizing bed reactor containing the nickel-containing solids (e.g., the nickel starting materials and/or a nickel metal) can be flushed with an inert gas that is essentially free of oxygen to remove molecular oxygen from the apparatus and from the nickel-containing solids. The reductant or reducing agent (e.g., hydrogen gas) can then be introduced into the fluidizing gas so that a mixture of reducing agent and the inert carrier gas is used to fluidize and substantially support the solid. The gas flow rate during reduction is not critical and may be adjusted to support the nickel metal or nickel starting materials and/or be determined by the type of equipment used for the reduction.

Upon completion of the reaction, the bed temperature can drop by about 10° C. The time period observed at the elevated bed temperature can correspond to the time required to add the stoichiometric amount of hydrogen which reduces the nickel starting materials and/or nickel metal to zero valent nickel metal. The zero valent nickel metal powder in the reactor can be cooled in an oxygen-free atmosphere and can exhibit ferromagnetism. The amount of nickel metal generated and its purity can be determined by a metal analysis using methods known to the skilled person. Similarly, the amount of nickel in any of the nickel-containing compositions used in the methods described herein can be determined by a metal analysis using methods known to the skilled person.

The suitability of a nickel metal powder preparation can be assessed by preparing zero-valent nickel-ligand complexes in a solvent or liquid substrate (e.g., 3-pentenenitrile (3PN)). After warming the mixture for a selected time period, the level of solubilized nickel-ligand complex in solution is measured, for example, by liquid chromatography. Unreacted nickel metal can be removed from the milieu by filtration or centrifugation and, if desired evaluated. Nickel complexes with a phosphorus-containing ligand and remains in solution in a solvent such a 3PN (which also a hydrocyanation substrate) as it forms a suitable zero-valent nickel-ligand complex.

Suitable nickel metal powder preparations can be reacted with monodentate or bidentate phosphorous containing ligands in a nitrile solvent to efficiently produce nickel complexes that can be used as homogeneous catalysts for the hydrocyanation of conjugated dienes to mononitriles, and the hydrocyanation of unsaturated nitriles to dinitriles.

Calcination

A reduction step can be carried out directly on nickel starting materials. Alternatively, a calcination step can be performed on nickel starting materials and then the reduction step can be carried out.

Prior to the reduction step, calcination step can be performed on nickel starting materials such as basic nickel carbonate, nickel carbonate, nickel bicarbonate, nickel oxalate, nickel formate, nickel squarate, nickel hydroxide, nickel oxide, nickel sulfate, nickel salts or combinations thereof. Calcination can remove volatile and gaseous substances from the nickel starting materials. For example, calcination converts BNC to nickel oxide, at least in part, by thermal decomposition of nickel carbonate (or nickel bicarbonate), with expulsion of carbon dioxide ($CO_2$) gas and water. Calcination can also remove sulfur dioxide and/or sulfur trioxide from nickel sulfate to generate nickel oxide.

Calcination can be performed in a convenient vessel, such as a fluid bed reactor, an expanded fixed bed, a rotary kiln, a rotary pan or any such equipment known to the skilled person. To facilitate uniform exposure of nickel starting materials to heat and optimally remove volatile and gaseous substances that may be absorbed onto nickel starting materials, a fluidized bed reduction vessel can be employed.

In general, calcination can be performed in any gaseous atmosphere not reactive with the nickel composition, for example, in a gas that does not form undesirable nickel compounds. Suitable convenient gases for the calcination step include air and nitrogen; others may include argon and helium. Steam (water vapor) can be present during the calcination step.

Generally, calcination can be carried out for a time and under thermal conditions sufficient to calcine the nickel starting material.

To perform calcination the nickel starting material can be placed in a closed reactor a flowing gas such as air, nitrogen, argon or mixtures thereof can be employed to support the nickel starting material(s). Air is an inexpensive and convenient gas suitable for the calcination step.

The temperature can be raised to a desired calcination temperature, for example, about 200° C. to 600° C. At the calcination temperature 300° C.-450° C., or higher, air with or without steam can be passed through the reactor for a period of about 1 to 2 hours, while volatile and gaseous substances are removed from the nickel starting material. For example, when BNC is used as a nickel starting material and the BNC is calcined, carbon dioxide can be removed and the BNC can be converted to nickel oxide. Similarly, calcination of nickel sulfate can release sulfur dioxide or sulfur trioxide to yield nickel oxide.

The calcination step can be performed at temperatures of about 200° C. to 600° C. Below 200° C., the calcination process may be slow or incomplete and thus unreacted nickel precursor may remain in the product. Above 600° C., an excessive collapse of the nickel oxide can occur, consequentially reducing the reactivity of the nickel powder product. The time for the calcination step can range from tens of seconds at 600° C. to multiple hours at 200° C. Suitable calcination temperatures can include, for example, temperatures of about 300° C. to about 475° C. At temperatures of about 300° C. to about 475° C. or about 325° C. and 450° C., calcination is substantially complete in a reasonable time period, such as about 1.25 to 2 hour.

After calcination, the nickel starting material (e.g., nickel oxide) can be reduced. For example, the reactor can be purged with a nitrogen atmosphere for a sufficient time to remove substantially all oxygen (e.g., 98% to 99.9% of oxygen) and the calcined nickel starting material can be reduced as described herein.

Particulate Nickel Preparations

Novel nickel metal preparations are described herein that are highly reactive with ligands to form of zero-valent nickel-phosphorus ligands complexes. Such complexes are used as catalysts, for example, as hydrocyanation catalysts. The nickel metal particulate forms of the invention are highly reactive with bidentate phosphite ligands in an organic liquid, such as an organonitrile liquid or an olefinic precursor for a hydrocyanation reaction. Upon contacting the nickel-ligand catalyst mixture with HCN, a hydrocyanation product of the olefin is produced in good yield.

A nickel particulate form of the invention embodies one or more of the characteristics described below and in the Figures. The invention provides a nickel particulate form for formation of a zero-valent nickel complex with a bidentate phosphorus-containing ligand, wherein the nickel particulate form has a large surface area as measured by the amount of gas molecules absorbed by the nickel particles (e.g., via BET Specific Surface Area measurements) and the nickel particulate form has a large number of small crystallites.

For example, the nickel particulate form can have a BET Specific Surface Area of at least about 1 m²/gm; more preferably, a BET Specific Surface Area of at least about 2 m²/gm; even more preferably, a BET Specific Surface Area of at least about 4 m²/gm; further more preferably, a BET Specific Surface Area of at least about 10 m²/gm.

Desirable nickel particulate forms can have a combination of physical characteristics. For example, preferred nickel particulate forms can have a combination of two or more of the following properties: a BET Specific Surface Area of at least about 1 m²/gm; nickel crystallites of average size of no greater than about 100 nm as determined by temperature programmed X-ray diffraction (TP-XRD); a C10 value that is less than about 20 nm after reduction at 300-400° C.; at least about $10^{16}$ surface crystallites of size C10 or less per gram nickel; at least about $2 \times 10^{15}$ surface crystallites per gram as calculated for cuboidal crystallites; a nickel crystallite size distribution span greater than 1.0.

In general, nickel particulate forms with two or more of these properties can effectively form complexes with phosphorus-containing ligands. More preferably, nickel particulate forms with three or more of these properties effectively form complexes with phosphorus-containing ligands.

The BET Specific Surface Area of a nickel particulate form can be a relevant physical property for nickel particulate forms. In general, nickel particulate forms with higher BET Specific Surface Areas exhibit improved complex formation with phosphorus-containing ligands. Thus, when combined with other desirable features, the nickel particulate form can have a BET Specific Surface Area of at least about 1 m²/gm. However, the nickel particulate form preferably has a BET Specific Surface Area greater than 2 m²/gm, more preferably the nickel particulate form can have a BET Specific Surface Area greater than 4 m²/gm, even more preferably the nickel particular form can have a BET Specific Surface Area of greater than about 10 m²/gm Desirable nickel particulate form can have a BET Specific Surface Area of 100 m²/gm or more. For example, the nickel particulate form can have a BET Specific Surface Area greater than 11 m²/gm, or greater than 12 m²/gm, or greater than 13 m²/gm, or greater than 14 m²/gm, or greater than 15 m²/gm, or greater than 16 m²/gm, or greater than 17 m²/gm, or greater than 18 m²/gm, or greater than 20 m²/gm. For example, the nickel particular form can have a BET Specific Surface Area of about 1 m²/gm to about 100 m²/gm, or any numerical value between 1-100 m²/gm, or between 10-50 m²/gm.

While not wishing to be bound by theory, nickel atoms from nickel particulate forms having a large surface, for example, as measured by the BET Specific Surface Area, may more readily be released from the particulate nickel and combine with phosphorus-containing ligands. Alternatively, the phosphorus-containing ligands may have greater access to the larger surface area of nickel particulate forms with higher BET Specific Surface Areas.

BET surface area, or gas absorption, measurement techniques can be used to measure the surface area and porosity of the particles present in a sample. Molecules of an adsorbate gas are physically adsorbed onto the particle surfaces, including the surfaces of any pores or crystallites, under controlled conditions within a vacuum chamber. For example, BET Specific Surface Area (BET SSA) can be measured by observing nitrogen adsorption using the Tristar 3000 Nitrogen Adsorption Instrument after degassing the samples under vacuum at 105° C. overnight. Multi-point BET measurements can be made using a partial pressure range of 0.05-0.3 P/Po. An adsorption isotherm can be obtained by measuring the pressure of the gas above the sample as a function of the volume of gas introduced into the chamber. The linear region of the adsorption isotherm can then be used to determine the volume of gas required to form a monolayer across the available particle surface area, using BET theory, as described by the following equation:

$$\frac{1}{v[(P/P_0)-1]} = \frac{c-1}{v_m}\left(\frac{P}{P_0}\right) + \frac{1}{v_m c}$$

where v is the volume of gas, P is the pressure, $P_0$ is the saturation pressure, $v_m$ is the volume of gas required to form a monolayer and c is the BET constant. Plotting relative pressure, $\phi(=P/P_0)$, and volume allows the volume of a monolayer to be determined from the gradient and intercept of the line.

The surface area of nickel particulate forms can also be measured by a Laser Diffraction Specific Surface Area technique. Nickel particulate forms can have a Laser Diffraction Specific Surface Area of at least about 0.4 m²/gm. Also, at least 10% of the nickel particles (D10) can have a diameter of no greater than about 4 μm.

Laser Diffraction Specific Surface Area (LD SSA) and particle size distribution (PSD) can be measured with a Mastersizer 2000 Particle Size Analyser (e.g., from Malvern Instruments Ltd using the Hydro 2000MU accessory and water as the dispersant). Light having a certain wavelength measured in micrometers is diffracted by the smaller size particles. The angle of diffraction will depend on the range of sizes present. The following equation can be used to report the Specific Surface Area (SSA):

$$SSA = \frac{6 \sum \frac{V_i}{d_i}}{\rho \sum V_i} = \frac{6}{\rho D[3,2]}$$

where Vi is the relative volume in class i with a mean class diameter of $d_i$, ρ is the density of the material, and D[3,2] is the surface area weighted mean diameter. This calculation can be carried out automatically within the laser diffraction system software. LD SSA provides a means of rapidly estimating the particle surface area. In carrying out this calculation, it is often assumed that the particles are substantially spherical, solid spheres.

The surface characteristics of the nickel particles composed of the crystallites can be such that a ratio of BET Specific Surface Area to Laser Diffraction Specific Surface Area is between 15 and 25.

Nickel particulate forms can have on average per gram at least about $10^{15}$ surface crystallites per gram nickel, preferably at least about $5 \times 10^{15}$ surface crystallites per gram nickel, more preferably at least about $10^{16}$ surface crystallites per gram nickel, even more preferably at least about $5 \times 10^{16}$ surface crystallites per gram nickel, and more preferably at least about $10^{17}$ surface crystallites per gram nickel. By a "surface crystallite" is meant a nickel crystallite on or within a nickel particle, where at least one side or edge of the crystallite is exposed to the surroundings. While not wishing to be bound by theory, the inventors herein believe that the suitability of nickel particulate forms having at least about $10^{15}$ to $10^{17}$ surface crystallites present is related to the presentation on the particle surface of numerous crystallite edges, which are believed to be more reactive than planar crystallite faces. The greater reactivity of the crystallite edges can be related to steric factors, electronic factors, or both in the interaction of the approaching ligand in solution to the surface of the solid nickel particulate form.

The desirable nickel particulate forms can have nickel crystallites of average size of no greater than about 70 nm (e.g., instead of 100 nm) as determined by temperature programmed X-ray diffraction (TP-XRD); or preferably the nickel crystallites have an average crystallite size of no greater than about 50 nm (instead of 100 nm or 70 nm); or more preferably the nickel crystallites have an average crystallite size of no greater than about 30 nm (instead of 100 nm, 70 nm or 50 nm). In general, nickel particulate forms with smaller nickel crystallites, particularly when combined with other desirable physical properties, are preferred.

The high degree of reactivity of the inventive nickel form is believed to arise, at least in part, from the properties of the nickel metal crystallites forming the particles. The inventive nickel particles can be composed of crystallites, regions of local crystalline order within the larger, disordered particle, wherein an average crystallite size (diameter) can be no greater than about 20-25 nm. More preferred nickel particulate forms can include nickel crystallite sizes with diameters in the range of 0.1 to 10 nm.

The nickel particulate forms can have combinations of even more desirable physical properties. For example, desirable nickel particulate forms can have on average have at least about $5 \times 10^{16}$ surface crystallites (e.g., instead of $10^{16}$ surface crystallites) of size C10 or less per gram nickel. More preferably, desirable nickel particulate forms can have on average have at least about $10^{17}$ surface crystallites (e.g., instead of $10^{16}$ or $5 \times 10^{16}$ surface crystallites) of size C10 or less per gram nickel.

In addition, the nickel crystallite size distribution span can be greater than 1.5. Crystallite size is typically measured as a diameter of the crystallite, for example, along the major dimension.

Other physical properties that the nickel particulate forms can have include those where at least 10% of the particles have a diameter (D10) of no greater than about 6 µm or preferably no greater than about 4 µm. The surface characteristics of the nickel particles composed of the crystallites can be such that the nickel particles have a ratio of BET Specific Surface Area to D10 of about $0.3 \times 10^6$ m/gm to about $10.0 \times 10^6$ m/gm, or about $0.5 \times 10^6$ m/gm to about $5 \times 10^6$ m/gm.

The nickel particulate form is zero-valent, i.e., metallic, nickel.

The nickel particulate form can be substantially dry, for example, a powder or particulate form. The nickel particulate form can be suspended, dissolved or partially dissolved in a solvent. The solvent is typically a non-aqueous solvent. The solvent can be an organic solvent. For example, the solvent for the nickel particulate form can be branched or unbranched C2-C20 hydrocarbon with one or more double bonds. The solvent for the nickel particulate form can be an organonitrile liquid such as a branched or unbranched C2-C20 alkyl or alkylene substituted by at least one nitrile (CN) group. Examples of solvent include pentenenitriles such as 2-pentenenitrile, 3-pentenenitrile, 4-pentenenitrile, 2-methyl-3-butenenitrile, and 2-methyl-2-butenenitrile.

The nickel particulate form can be substantially pure nickel in dry form or suspended or dissolved in a solvent. For example, the nickel particulate form can be isolated without, or be substantially free of, an associated ion (e.g., without an anion) or metal (e.g., without aluminum, copper, tungsten, zinc and/or iron). The nickel particular form can be free of impurities such as carbon-containing, silicon-containing and/or nitrogen-containing moieties and/or compounds. The nickel particulate form can be substantially free of impurities such as sodium, calcium, magnesium, potassium, and/or other alkali metals and/or alkaline earth metals. For example, the nickel particulate form can have less than 10% impurities, or less than 7% impurities, or less than 5% impurities, or less than 4% impurities, or less than 3% impurities, or less than 2% impurities, or less than 1% impurities, or less than 0.7% impurities, or less than 0.6% impurities, or less than 0.5% impurities, or less than 0.4% impurities, or less than 0.3% impurities, or less than 0.2% impurities, or less than 0.1% impurities, or less than 0.07% impurities, or less than 0.05% impurities, or less than 0.03% impurities, or less than 0.01% impurities. Other than their sulfur content, the nickel particulate form can be 95% to 99.9% pure, or 98% to 99.99% pure.

Such nickel particulate forms can be combined with a phosphorus-containing ligand, for example, any of those described herein.

Phosphorus-Containing Ligands

A "phosphorus-containing ligand" as the term is used herein refers to a ligand containing at least one phosphorus atom, that is suitable for formation of a complex with a transition metal such as nickel, wherein the complex can possess catalytic activity for an organic reaction such as a hydrocyanation reaction of an olefin, such as the hydrocyanation of butadiene to yield pentenenitrile, or the hydrocyanation of pentenenitrile to yield adiponitrile.

The hydrocyanation catalysts provided herein are composed of nickel and at least one phosphorus-containing (P-containing) ligand. The P-containing ligand can, for example, be a phosphite, a phosphonite, a phosphinite, a phosphine, and a mixed P-containing ligand or a combination of such members. The P-containing ligands may be monodentate or multidentate, for example, bidentate or tridentate.

The P-containing ligands can chemically bond to a metal, e.g., nickel, as complexes comprising a metal, and one or more P-containing ligands.

The term "monodentate" is known in the art and means only one phosphorus atom of the ligand (which can contain one or more phosphorus atoms per molecule) may be bonded to a single metal (e.g., nickel) atom. Two monodentate ligands can separately be bonded to the metal atom, or one monodentate ligand and one multidentate ligand can each be bonded to the metal atom.

The term "bidentate" is known in the art and means two phosphorus atoms of the ligand (which can contain two or more phosphorus atoms per molecule) may be bonded to a single metal (e.g., nickel) atom. A bidentate P-containing ligand can, for example, be selected from the group consisting of a bidentate phosphite, a bidentate phosphonite, a bidentate phosphinite, a bidentate phosphine or a mixed bidentate ligand.

A mixed bidentate ligand can, for example, be selected from the group consisting of a phosphite-phosphonite, a phosphite-phosphinite, a phosphite-phosphine, a phosphonite-phosphinite, a phosphonite-phosphine, and a phosphinite-phosphine.

The term "tridentate" means three phosphorus atoms of the ligand (which can contain three or more phosphorus atoms per molecule) may be bonded to a single metal (e.g., nickel) atom. The terms "bidentate" and "tridentate" may also be called chelate ligands.

The phosphorous-containing ligand may be a monodentate phosphite, monodentate phosphonite, monodentate phosphinite, monodentate phosphine, bidentate phosphite, bidentate phosphonite, bidentate phosphinite, or bidentate phosphine, and any combination of these members. Further, the phosphorous-containing ligand may be a monodentate phosphite to form the nickel complex of the monodentate phosphite then the nickel complex of the monodentate phosphite may be combined with a bidentate phosphorous-containing ligand. Likewise, the phosphorous-containing ligand may be a bidentate phosphite further comprising a monodentate phosphite. For example, suitable phosphorus-containing ligands include mixtures of one or more members selected from monodentate phosphite ligands, bidentate phosphite ligands and mixtures of monodentate and bidentate phosphite ligands.

Suitable phosphorus-containing ligands for the catalyst include those selected from the group consisting of compounds of Formula (III), Formula (IV), Formula (IVa) or combinations thereof. Formula (III) has the structure:

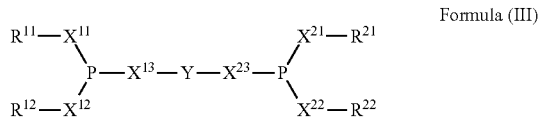

Formula (III)

wherein,
$X^{11}, X^{12}, X^{13}, X^{21}, X^{22}$ and $X^{23}$ independently represent oxygen or a single (direct) bond;
$R^{11}$ and $R^{12}$ independently represent identical or different, single or bridged organic radicals;
$R^{21}$ and $R^{22}$ independently represent identical or different, single or bridged organic radicals; and
Y represents a bridging group.

For example, $X^{11}, X^{12}, X^{13}, X^{21}, X^{22}$ and $X^{23}$ may each be oxygen. In such a case, the bridging group Y is bonded to phosphite groups. Alternatively, $X^{11}$ and $X^{12}$ may each be oxygen and $X^{13}$ a single bond, or $X^{11}$ and $X^{13}$ can each be oxygen and $X^{12}$ a single bond, so that the phosphorus atom surrounded by $X^{11}$, $X^{12}$ and $X^{13}$ is the central atom of a phosphonite. In such a case, $X^{21}$, $X^{22}$ and $X^{23}$ may each be oxygen, or $X^{21}$ and $X^{22}$ may each be oxygen and $X^{23}$ a single bond, or $X^{21}$ and $X^{23}$ may each be oxygen and $X^{22}$ a single bond, or $X^{23}$ may be oxygen and $X^{21}$ and $X^{22}$ each a single bond, or $X^{21}$ may be oxygen and $X^{22}$ and $X^{23}$ each a single bond, or $X^{21}$, $X^{22}$ and $X^{23}$ may each be a single bond, so that the phosphorus atom surrounded by $X^{21}$, $X^{22}$ and $X^{23}$ may be the central atom of a phosphite, phosphonite, phosphinite or phosphine, preferably a phosphonite. Preferably, $X^{13}$ may be oxygen and $X^{11}$ and $X^{12}$ each may be a single bond, or $X^{11}$ may be oxygen and $X^{12}$ and $X^{13}$ each may be a single bond, so that the phosphorus atom surrounded by $X^{11}$, $X^{12}$ and $X^{13}$ is the central atom of a phosphonite. In such a case, $X^{21}$, $X^{22}$ and $X^{23}$ may each be oxygen, or $X^{23}$ may be oxygen and $X^{21}$ and $X^{22}$ each a single bond, or $X^{21}$ may be oxygen and $X^{22}$ and $X^{23}$ each a single bond, or $X^{21}$, $X^{22}$ and $X^{23}$ may each be a single bond, so that the phosphorus atom surrounded by $X^{21}$, $X^{22}$ and $X^{23}$ may be the central atom of a phosphite, phosphonite, phosphinite or phosphine, preferably a phosphinite. In some cases, $X^{11}$, $X^{12}$ and $X^{13}$ may each be a single bond, so that the phosphorus atom surrounded by $X^{11}$, $X^{12}$ and $X^{13}$ is the central atom of a phosphine. In such a case, $X^{21}$, $X^{22}$ and $X^{23}$ may each be oxygen, or $X^{21}$, $X^{22}$ and $X^{23}$ may each be a single bond, so that the phosphorus atom surrounded by $X^{21}$, $X^{22}$ and $X^{23}$ may be the central atom of a phosphite or phosphine, preferably a phosphine. The bridging group Y is particularly an arylene group which is substituted, for example by $C_1$-$C_4$-alkyl, halogen, such as fluorine, chlorine, bromine, halogenated alkyl, such as trifluoromethyl, arylene, such as phenylene, or such an arylene is unsubstituted. The arylene can be a group having from 6 to 20 carbon atoms in the aromatic system, in particular pyrocatechol, bis(phenol) or bis(naphthol). The $R^{11}$ and $R^{12}$ radicals may each independently be identical or different organic radicals. Advantageous $R^{11}$ and $R^{12}$ radicals may be aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups. The $R^{21}$ and $R^{22}$ radicals may each independently be identical or different organic radicals. Advantageous $R^{21}$ and $R^{22}$ radicals may be aryl radicals, particularly those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups. The $R^{11}$ and $R^{12}$ radicals may each be separate or bridged. The $R^{21}$ and $R^{22}$ radicals may also each be separate or bridged. The $R^{11}$, $R^{12}$, $R^{21}$ and $R^{22}$ radicals may each be separate, two may be bridged and two separate, or all four may be bridged, in the manner described.

Formula (IV) has the structure, $$P(X^1R^1)(X^2R^2)(X^3R^3)$$ Formula (IV)

wherein,
$X^1$, $X^2$ and $X^3$ independently represent oxygen or a single direct bond; and
$R^1$, $R^2$ and $R^3$ are each independently identical or different organic radicals.

For example, $R^1$, $R^2$ and $R^3$ can each independently be alkyl radicals preferably having from 1 to 10 carbon atoms, such as methyl, ethyl, n-propyl, i-propyl, n-butyl, i-butyl, s-butyl, t-butyl, or aryl groups such as phenyl, o-tolyl, m-tolyl, p-tolyl, 1-naphthyl, 2-naphthyl, or hydrocarbyl, preferably having from 1 to 20 carbon atoms, such as 1,1'-biphenol, 1,1'-binaphthol. The $R^1$, $R^2$ and $R^3$ groups may be bonded together directly, i.e. not solely via the central phosphorus atom. Preference may be given to the $R^1$, $R^2$ and $R^3$ groups not being bonded together directly. $R^1$, $R^2$ and $R^3$ groups can also be radicals selected from the group consisting of phenyl, o-tolyl, m-tolyl and p-tolyl. In particular, a maximum of two of the $R^1$, $R^2$ and $R^3$ groups should be phenyl groups. A maximum of two of the $R^1$, $R^2$ and $R^3$ groups can be o-tolyl groups. Particular compounds that may be used are those of the formula (IVa) below:

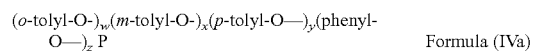

Formula (IVa)

where w, x, y, z are each a natural number and the following conditions apply: w+x+y+z=3 and z is less than or equal to 2.

Examples of compounds of formula (IVa) are (o-tolyl-O—)$_3$P, (p-tolyl-O—)(phenyl-O—)$_2$P, (m-tolyl-O—)(phenyl-O—)$_2$P, (o-tolyl-O—)(phenyl-O—)$_2$P, (p-tolyl-O—)$_2$(phenyl-O—)P, (m-tolyl-O—)$_2$(phenyl-O—)P, (o-tolyl-O—)$_2$ (phenyl-O—)P, (m-tolyl-O—)(p-tolyl-O—) (phenyl-O—)P, (o-tolyl-O—)(p-tolyl-O—)(phenyl-O—)P, (o-tolyl-O—)(m-tolyl-O—) (phenyl-O—)P, (p-tolyl-O—)$_3$P, (m-tolyl-O—)(p-tolyl-O—)$_2$P, (o-tolyl-O—)(p-tolyl-O—)$_2$P, (m-tolyl-O—)$_2$(p-tolyl-O—)P, (o-tolyl-O—)$_2$(p-tolyl-O—)P, (o-tolyl-O—)(m-tolyl-O—)(p-tolyl-O—)P, (m-tolyl-O—)$_3$P, (o-tolyl-O—)(m-tolyl-O—)$_2$P, (o-tolyl-O—)$_2$(m-tolyl-O—)P or mixtures of such compounds.

An example of a useful bidentate phosphite ligand is Ligand (V), shown below

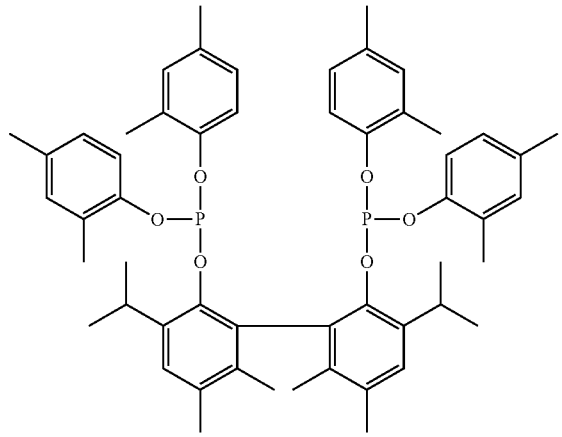

Ligand (V)

Further examples of bidentate phosphite ligands that are useful in the present process include those having the Formulae (VI) to (IX), shown below wherein for each formula, $R^{17}$ is selected from the group consisting of methyl, ethyl or isopropyl, and $R^{18}$ and $R^{19}$ are independently selected from H or methyl:

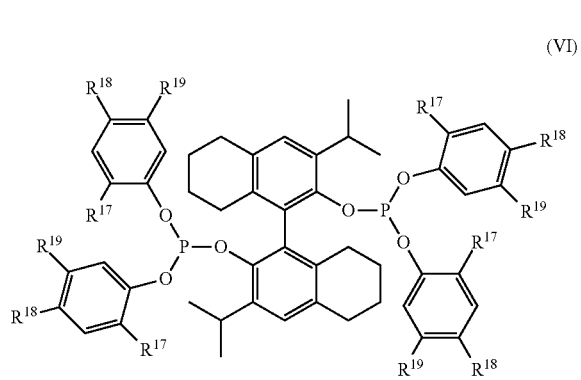

(VI)

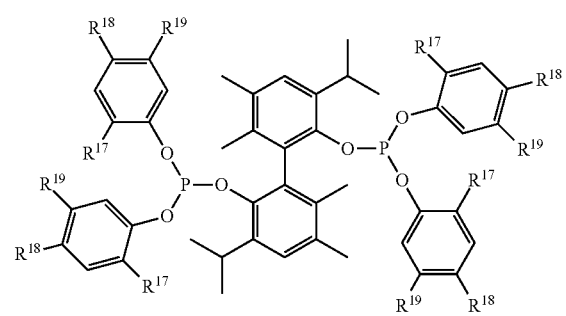

(VII)

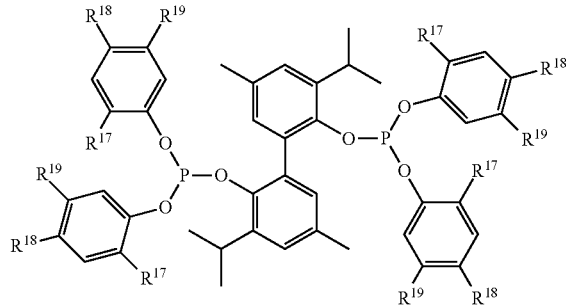

(VIII)

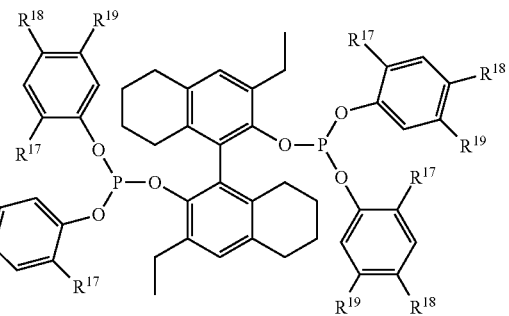

(IX)

Additional examples of bidentate phosphite ligands that are useful in the present process include a ligand selected from a member of the group represented by Formulae (X) and (XI), in which all like reference characters have the same meaning, except as further explicitly limited:

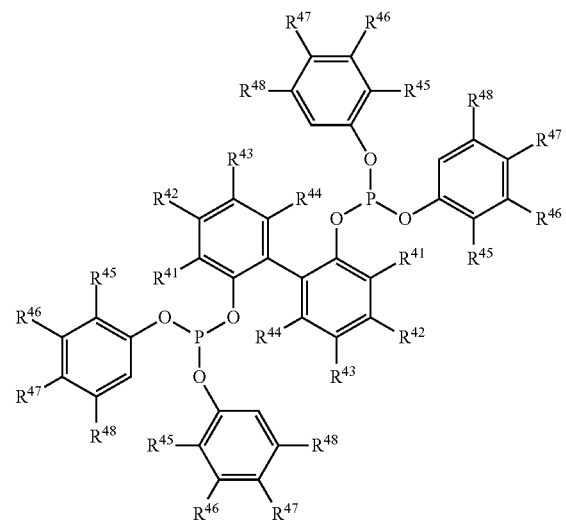

(X)

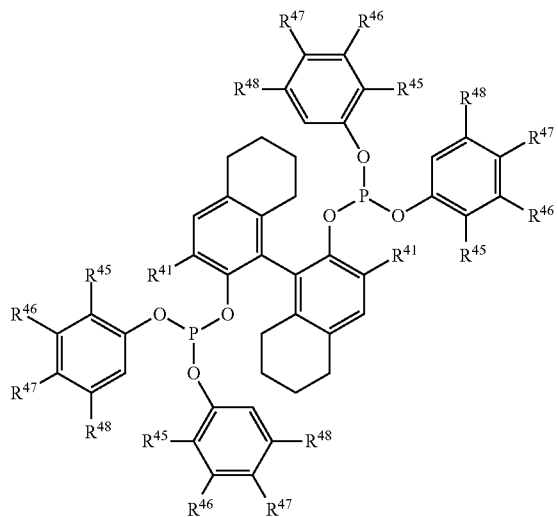

(XI)

wherein, $R^{41}$ and $R^{45}$ are independently selected from the group consisting of $C_1$ to $C_5$ hydrocarbyl, and each of $R^{42}$, $R^{43}$, $R^{44}$, $R^{46}$, $R^{47}$ and $R^{48}$ is independently selected from the group consisting of H and $C_1$ to $C_4$ hydrocarbyl. As used herein, "hydrocarbyl" particularly is alkyl or cycloalkyl.

For example, the bidentate phosphite ligand can be selected from a member of the group represented by Formula (X) and Formula (XI), wherein $R^{41}$ is methyl, ethyl, isopropyl or cyclopentyl;
$R^{42}$ is H or methyl;
$R^{43}$ is H or a $C_1$ to $C_4$ hydrocarbyl;
$R^{44}$ is H or methyl;
$R^{45}$ is methyl, ethyl or isopropyl; and
$R^{46}$, $R^{47}$ and $R^{48}$ are independently selected from the group consisting of H and $C_1$ to $C_4$ hydrocarbyl.

As additional examples, the bidentate phosphite ligand can be selected from a member of the group represented by Formula (X), wherein $R^{41}$, $R^{44}$, and $R^{45}$ are methyl;
$R^{42}$, $R^{46}$, $R^{47}$ and $R^{48}$ are H; and
$R^{43}$ is a $C_1$ to $C_4$ hydrocarbyl;
or
$R^{41}$ is isopropyl;
$R^{42}$ is H;
$R^{43}$ is a $C_1$ to $C_4$ hydrocarbyl;
$R^{44}$ is H or methyl;
$R^{45}$ is methyl or ethyl;
$R^{46}$ and $R^{48}$ are H or methyl; and
$R^{47}$ is H, methyl or tertiary-butyl;
or the bidentate phosphite ligand can be selected from a member of the group represented by Formula XI, wherein
$R^{41}$ is isopropyl or cyclopentyl;
$R^{45}$ is methyl or isopropyl; and
$R^{46}$, $R^{47}$, and $R^{48}$ are H.

As yet another example, the bidentate phosphite ligand can be represented by Formula (X), wherein $R^{41}$ is isopropyl; $R^{42}$, $R^{46}$, and $R^{48}$ are H; and $R^{43}$, $R^{44}$, $R^{45}$, and $R^{47}$ are methyl.

It will be recognized that Formulae (V) to (XI) are two-dimensional representations of three-dimensional molecules and that rotation about chemical bonds can occur in the molecules to give configurations differing from those shown. For example, rotation about the carbon-carbon bond between the 2- and 2'-positions of the biphenyl, octahydrobinaphthyl, and or binaphthyl bridging groups of Formulae (V) to (XI), respectively, can bring the two phosphorus atoms of each Formula in closer proximity to one another and can allow the phosphite ligand to bind to nickel in a bidentate fashion. The term "bidentate" is well known in the art and means both phosphorus atoms of the ligand are bonded to a single nickel atom. In addition, use of an optically active moiety such as sec-butyl for $R^{41}$ can result in optically active catalysts.

Bidentate Phosphorus-Containing Ligand Synthesis

Ligand (V) is an example of a bidentate phosphorus-containing ligand. Ligand (V) may be prepared by any suitable synthetic means known in the art. For example, 3,3'-diisopropyl-5,5',6,6'-tetramethyl-2,2'-biphenol can be prepared by the procedure disclosed in U.S. Published Patent Application No. 2003/0100802 in which 4-methylthymol can undergo oxidative coupling to the substituted biphenol in the presence of a copper chlorohydroxide-TMEDA complex (TMEDA is N,N,N',N'-tetramethylethylenediamine) and air. The phosphorochloridite of 2,4-xylenol, $[(CH_3)_2C_6H_3O]_2PCl$, can be prepared, for example, by the procedure disclosed in U.S. Published Patent Application No. 2004/0106815. To selectively form this phosphorochloridite, anhydrous triethylamine and 2,4-xylenol can be added separately and concurrently in a controlled manner to $PCl_3$ dissolved in an appropriate solvent under temperature-controlled conditions. The reaction of this phosphorochloridite with the 3,3'-diisopropyl-5,5',6,6'-tetramethyl-2,2'-biphenol to form the desired Ligand (V) can be performed, for example, according to the method disclosed in U.S. Pat. No. 6,069,267. The phosphorochloridite can be reacted with 3,3'-diisopropyl-5,5',6,6'-tetramethyl-2,2'-biphenol in the presence of an organic base to form Ligand (V), which can be isolated according to techniques available in the art, for example as also described in U.S. Pat. No. 6,069,267.

Additional bidendate ligands, ligand complexes, and methods of making the same, are disclosed in U.S. Pat. No. 6,171,996, herein incorporated by reference in its entirety.

Nickel-Phosphorus Ligand Complex Formation

Nickel-phosphorus ligand complexes can be effective hydrogenation catalysts. Such nickel-phosphorus ligand complexes can be formed by mixing nickel metal particles, and one or more phosphorus-containing ligands in an organonitrile solvent. A Lewis acid can also be included in the nickel metal-phosphorus ligand complex forming solution. As described herein sulfur sources can be added to the mixture of the nickel metal particles, and one or more phosphorus-containing ligands to improve complex formation between nickel atoms and the phosphorus-containing ligands.

The phosphorus-containing ligand(s) can be any of those described herein.

The nickel metal used for complex formation can be pretreated with a sulfur source as described herein or it can be treated with a sulfur source while in the nickel metal-phosphorus ligand complex forming solution.

The nickel metal used for complex formation with one or more phosphorus-containing ligand(s) can be a particulate (powdered) nickel metal. Particulate nickel metals can have a range of particle sizes. A "nickel particle" is a discrete particle, typically visible in a scanning electron micrograph. For example, at least 10% of the nickel particles can have a diameter (D10) of less than about 6 µm. The term "D10" refers to the largest particle diameter of the smallest 10% of the particles in a sample of particles. Useful particulate nickel starting materials can have surface crystallites. A "crystallite" is a region of local crystalline order within, or on, a nickel particle. A "surface crystallite" refers to a crystallite contained within a particle, but wherein a portion of the crystallite is exposed to the environment surrounding the particle, such as an organic liquid containing a ligand. Each nickel particle ideally has a large number of crystallites. For example, the nickel can have an average of at least about $10^{15}$ surface crystallites per gram of nickel. The nickel metal particles can also have a BET Specific Surface Area of at least about 1 $m^2/gm$ or the BET Specific Surface Area for the nickel metal particles can be at least about 10 $m^2/gm$. Such nickel metal particles can be treated with a sulfur source prior to complex formation with phosphorus-containing ligand(s), or during complex formation with phosphorus-containing ligand(s).

The organonitrile solvent can be selected from one or more members of the group consisting of 2-pentenenitrile, 3-pentenenitrile, 4-pentenenitrile, 2-methyl-3-butenenitrile, 2-methyl-2-butenenitrile, adiponitrile, 2-methylglutaronitrile, and ethylsuccinonitrile. For example, the organonitrile can be a pentenenitrile or a mixture of pentenenitriles.

The Lewis acid can be selected from the group consisting of inorganic or organometallic compounds in which the cation is selected from the group including scandium, titanium, vanadium, chromium, manganese, iron, cobalt, copper, zinc, boron, aluminum, yttrium, zirconium, niobium, molybdenum, cadmium, rhenium, lanthanum, europium, ytterbium, tantalum, samarium, tin and mixtures thereof. A Lewis acid can be selected from the group consisting of zinc chloride, ferrous chloride, or a combination of zinc chloride, ferrous chloride and mixtures thereof. For example, the Lewis acid can be zinc chloride.

The nickel metal, sulfur source, Lewis acid, phosphorus-containing ligands and/or organonitrile solvent can be substantially free of metals such as aluminum, copper, tungsten, mercury and/or iron. For example, the nickel particles, sulfur source, Lewis acid, phosphorus-containing ligands and/or organonitrile solvent can be substantially free of silicon-containing moieties and/or compounds. The nickel particles, sulfur source, Lewis acid, phosphorus-containing ligands and/or organonitrile solvent can also be substantially free of sodium, calcium, magnesium, potassium, and/or other alkali metals and/or alkaline earth metals.

The nickel and/or sulfur source mixed with the phosphorus-containing ligands can be substantially free of hydrocarbons, carbon dioxide, and other carbon containing compounds. For example, the nickel and/or sulfur source mixed with the phosphorus-containing ligands can be substantially free of silicon, sodium, potassium, calcium, magnesium, phosphorus, aluminum, copper, tungsten, mercury, and/or iron impurities. The nickel and/or sulfur source mixed with the phosphorus-containing ligands can have less than 10% impurities, or less than 7% impurities, or less than 5% impurities, or less than 4% impurities, or less than 3% impurities, or less than 2% impurities, or less than 1% impurities, or less than 0.7% impurities, or less than 0.6% impurities, or less than 0.5% impurities, or less than 0.4% impurities, or less than 0.3% impurities, or less than 0.2% impurities, or less than 0.1% impurities, or less than 0.07% impurities, or less than 0.05% impurities, or less than 0.03% impurities, or less than 0.01% impurities.

The nickel particles, Lewis acid and one or more phosphorus-containing ligands can be mixed with the organonitrile solvent at a temperature and for a time sufficient for complex formation between nickel atoms and the phosphorus-containing ligands. For example, the nickel particles, Lewis acid and one or more phosphorus-containing ligands can be mixed with the organonitrile solvent at a temperature between 0° C. and 150° C. for about 15 minutes to about 24 hours. For example, a temperature sufficient for complex formation can be about 4° C. to about 130° C., or about 10° C. to about 110° C., or about 15° C. to about 100° C., or about 20° C. to about 100° C., or about 40° C. to about 100° C., or about 60° C. to about 80° C.

A time sufficient for complex formation is a time for reaching equilibrium in the formation of nickel-phosphorus containing ligands. For example, a time for reaching equilibrium can be about 5 minutes to about 24 hours, or about 10 minutes to about 12 hours, or about 15 minutes to about 8 hours, or about 20 minutes to about 4 hours, or about 20 minutes to about 2 hours. A preferred time for reaching equilibrium can be about 20 minutes to about 40 minutes, or about 30 minutes.

The nickel-phosphorus ligand complexes can typically be formed under a non-oxygen atmosphere. For example, a nitrogen atmosphere can be employed.

Assay for Nickel-Phosphorus Ligand Complex Formation

To evaluate the suitability of nickel preparations for preparation of hydrocyanation catalysts, a nickel preparation is evaluated to ascertain whether nickel metal in the nickel preparation forms a complex with one or more phosphorus-containing ligands at a rate sufficient for use in a manufacturing process.

An assay can be used to evaluate the suitability of nickel preparations for preparation of hydrocyanation catalysts. Such an assay involves mixing a nickel test sample (e.g., 1-7 wt % nickel relative to the total weight of the reaction mixture) with one or more phosphorus-containing ligands and a Lewis acid in an organonitrile solvent. The phosphorus-containing ligand can be any of the phosphorus-containing ligands described herein. Preferably, the phosphorus-containing ligand can be a bidentate phosphite ligand such as Ligand (V). The Lewis acid can be zinc chloride. The organonitrile solvent can be pentenenitrile.

A sample of known mass of the nickel powder (e.g., 4 wt % nickel) can be contacted with about 0.5 to 2.5 moles Lewis acid (such as zinc chloride) per mole bidentate phosphite ligand (e.g., Ligand (V)) in a 3-pentenenitrile (3PN) solution. The mixture can be warmed for a period of hours, during which time the level of solubilized nickel in solution is measured by liquid chromatography (LC). The amount of ligand and/or zinc chloride in the assay mixture can be in stoichiometric excess relative to the amount of nickel powder added. However, it may be desirable to limit the amount of ligand and/or zinc chloride in the assay mixture relative to the amount of nickel powder added. Thus, the concentration of ligand and/or zinc chloride in the assay mixture can be limiting relative to the amount of nickel powder present.

Nickel becomes soluble in the organonitrile solvent (e.g., a hydrocyanation substrate such as 3PN) when it forms a complex with the phosphorus-containing ligand. Unreacted nickel metal can be removed from the mixture by filtration or centrifugation.

To avoid contact with air, a reactor bottle, equipped with a magnetic stir bar, can be charged with the reactants inside a Vacuum Atmospheres dry box operating with a dry nitrogen atmosphere. The reactants added to this bottle can include the nickel preparation to be tested, one or more phosphorus-containing ligands (e.g. Ligand (V)), where the solvent is 3-pentenenitrile. Zinc chloride can also be added to the assay mixture.

To standardize the test procedure, 4-5 wt % nickel is mixed at about 60° C. to 80° C. in a 3-pentenenitrile (3PN) solution containing about 0.5 to 2.5 moles zinc chloride per mole bidentate phosphorus-containing ligand. For example, 4 wt % nickel preparation can be mixed with approximately 5.25 wt % Ligand (V) and 6300 ppm $ZnCl_2$ in a solution of 3-pentenenitrile. The zinc to Ligand (V) molar ratio employed is then about 0.75.

The reactor bottle can be sealed, removed from the dry box, and moved to a laboratory fume hood where it can be placed on a magnetic stir plate. The reaction mixture within the reaction bottle can then be heated to 60° C.-80° C. (e.g., 60° C.). Sufficient agitation can be used to suspend the nickel-containing solid in this reaction mixture.

Filtered liquid samples from the reaction mixture can be removed from the reactor bottle at intervals of from 5 minutes to one hour. A final sample can be taken after 24 hours. The amount of soluble nickel in the samples is measured using liquid chromatography (LC). This limit of detection for this assay is about 20-50 ppm soluble nickel in the form of soluble nickel complexes of Ligand (V).

The activity of a nickel preparation is therefore measured by its propensity to form soluble zero-valent nickel metal phosphorus ligand complexes. The activity of a nickel preparation can be compared to a control nickel preparation in this assay for formation of soluble zero-valent nickel metal phosphorus ligand complexes. For example, the control nickel preparation can be a nickel preparation that is determined to have inadequate activity. An active nickel preparation is therefore a nickel form that has more activity than the inactive negative control nickel preparation. The control nickel preparation can be a nickel preparation that is determined to have good activity. An active nickel preparation is therefore a nickel form that has about the same or more activity than the active positive control nickel preparation.

One example of a control nickel preparation is a nickel powder obtained from MetChem BNC using a one-step hydrogenation process (i.e., not including calcination pretreatment), where the hydrogenation is performed at 400° C. Such a nickel preparation made from MetChem BNC is described in Table 1 and has nickel activity that is typically below that which enables the efficient preparation of the zero-valent nickel complexes suitable for use in a manufacturing process involving a hydrocyanation catalyst.

An empirical rate equation for Ni dissolution in catalyst-preparation assay is employed to provide a numerical value indicative of nickel 'activity' (ability to become a soluble catalyst complex with Ligand (V)) in the following reaction:

$$Ni+Ligand(V)(A)+ZnCl_2(B)+3PN \leftrightarrow Catalyst(C)$$

The following equation describes the rate of Nickel-Ligand (V) catalyst formation:

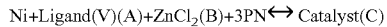

$$r = a*k'*w_{Ni}*C_A^{a'}*C_B^{b}*[1-C_C/(K_{eq}*C_A*C_B)]*2*(C_A/C_{A0})/[1+(C_A/C_{A0})]$$

where:
a=activity of nickel
$w_{Ni}$=weight loading of nickel (weight of nickel/weight of solution)
k'=Arrhenius rate constant:

[(mmoles Ni/liter)^0.5/hr]=$1.539 \times 10^{10} exp[-6832.1/T(K)]$ $C_A$=concentration of Ligand (V) (mmol/L)
$C_{A0}$=Initial concentration of Ligand (V) (mmol/L)
$C_B$=concentration of $ZnCl_2$ (mmol/L)
a'=order of reaction with respect to D80=0
b=order of reaction with respect to $ZnCl_2$=0.5
$K_{eq}$=equilibrium constant for the chemical reaction

[liters/mmol]=$exp[11555/T(K)-35.231]$

T=temperature in degree Kelvin.

It is assumed that the 3-pentenenitrile is in far excess so its order of reaction with respect to the rate of 3-pentenenitrile dissolution is considered zero. The order of reaction with nickel loading is considered to be 1.

The rate constant k' is defined for a standard MetChem BNC reduced at 400° C. under pure hydrogen to nickel. However, to account for other sources of nickel that can have different in properties, a factor is applied that is termed the activity of nickel dissolution. The 'activity' number was chosen to be 1 for the specific condition of MetChem BNC reduced at 400° C. to nickel, dissolved at 80° C. in the catalyst-preparation solution with $ZnCl_2$/Ligand (V) molar ratio of 0.8 and 4 wt % nickel loading where dissolution is at a rate of 980 ppm Ni/hr. In principle, a higher activity is essentially a higher rate constant specific to a given nickel. In order to move away from separately determining rate constant for each type of nickel, the activity term is defined to get around this issue.

Using such an equation, a nickel preparation is active if it has an activity of at least 2.0, preferably at least 3.0 and more preferably at least 4.0.

Nickel preparations are also active if they efficiently form zero-valent nickel phosphorus ligand complexes at a rate suitable for use in a manufacturing process involving a hydrocyanation catalyst. A suitable rate is a time for achieving equilibrium in the formation of a nickel metal phosphorus ligand complex of no more than 8 hours, no more than 6 hours, no more than 5 hours, no more than 4 hours, no more than 3 hours, no more than 2 hours, no more than 1 hour, or no more than 30 minutes. Nickel preparations that form complexes with phosphorus-containing ligands very slowly (e.g., by requiring several days or a week for formation) are not active nickel preparations useful for generating hydrocyanation catalysts.

Containers for Catalyst Storage and Shipment

Containers such as barrels, drums, of various sizes and shapes may be used for the storage and transport of the nickel, phosphorus-containing ligand and/or catalyst. In particular, containers which allow ingress and egress of contents with minimal exposure to the atmosphere and other sources of oxygen may be used. Polymeric materials are particularly used for any contact with the nickel and/or ligand catalyst. Collapsible drums suitable for the nickel and/or catalyst ligand storage and transport are described in WO 2011/094411 published Aug. 4, 2011 and assigned to Pack-Gen of Auburn, Me. USA.

Materials used for such containers and coming into contact with the nickel and/or catalyst ligand include polymers such as polyethylene terephthalate (PET), polyethylene napthalate (PEN), polypropylene and polyethylene as well as metal containers that are resistant to leaching by the ligand catalyst.

Containers having an oxygen-scavenging core layer are described in U.S. Pat. No. 7,056,565 issued to Chevron and various structural and chemical compositional aspects of the container may be used for storage and transport of ligand compounds.

Containers for oxygen-sensitive products are described in U.S. Pat. No. 7,854,973 issued to Sonoco wherein an oxidation catalyst is provided in a first outer layer to consume oxygen which diffuses into the interior. Various structural and chemical compositional aspects of U.S. Pat. No. 7,854,973 may be used as containers, provided that the mechanism for scavenging the oxygen does not oxidize the nickel and/or ligand. Wall layers are provided which may be an ethylene-vinyl alcohol copolymer, polyamide homo or copolymer, polyacrylonitrile copolymer, polyvinyl chloride (PVC) or other polymer with low oxygen permeability.

Catalyst container structures described in U.S. Pat. No. 4,946,068 issued to Amoco and WO 2006/052677 issued to Exxon-Mobil for catalyst storage, transfer and dispensing may be used for storage and transport of the nickel and/or ligands.

Thermoplastic containers for the storage and transportation of dangerous liquid fillings are described in EP 0 673 841 issued to Mauser-Werke of Bruhl, Germany.

Inert atmospheric packaging (IAP) or modified atmosphere packaging (MAP) is generally useful for storage and transport of the ligands and/or nickel metal preparations described herein. Thus, charging of the ligand/solvent mixture for storage or shipment into an appropriate container is accompanied by, followed by or both, rendering the headspace above the liquid surface as an inert or very low reactivity atmosphere.

DEFINITIONS

As used in the specification and the appended claims, the singular forms "a," "an" and "the" include plural referents unless the context clearly dictates otherwise.

In this document, the term "or" is used to refer to a nonexclusive or, such that "A or B" includes "A but not B," "B but not A," and "A and B," unless otherwise indicated.

The term "about" can allow for a degree of variability in a value or range, for example, within 10%, within 5%, or within 1% of a stated value or of a stated limit of a range. When a range or a list of sequential values is given, unless otherwise specified any value within the range or any value between the given sequential values is also disclosed.

BET surface area (BET SSA), or gas absorption, is a measure of the surface area and porosity of nickel metal particles. BET theory relates to the adsorption of gas molecules on a solid surface and provides methods for measurement of the specific surface area of a material. See, e.g., Brunauer et al., J. Am. Chem. Soc. 60: 309 (1938). Molecules of an adsorbate gas are physically adsorbed onto the particle surfaces, including the surfaces of any pores or crystallites, under controlled conditions within a vacuum chamber. For example, BET Specific Surface Area (BET SSA) can be measured by observing nitrogen adsorption using the Tristar 3000 Nitrogen Adsorption Instrument after degassing the samples under vacuum at 105° C. overnight. Multi-point BET measurements can be made using a partial pressure range of 0.05-0.3 P/Po. An adsorption isotherm is obtained by measuring the pressure of the gas above the sample as a function of the volume of gas introduced into the chamber. The linear region of the adsorption isotherm can then be used to determine the volume of gas required to form a monolayer across the available particle surface area, using BET theory, as described by the following equation:

$$\frac{1}{v[(P/P_0)-1]} = \frac{c-1}{v_m}\left(\frac{P}{P_0}\right) + \frac{1}{v_m c}$$

where $v$ is the volume of gas, $P$ is the pressure, $P_0$ is the saturation pressure, $v_m$ is the volume of gas required to form a monolayer and $c$ is the BET constant. Plotting relative pressure, $\phi(=P/P_0)$, and volume allows the volume of a monolayer to be determined from the gradient and intercept of the line.

The ratio BET SSA/C50 provides a value that is independent of the crystallite's geometry. The values obtained for a set of samples, can be correlated with "nickel activity" as defined here, and a reasonable linear correlation between activity and BET SSA/C50 has been found, as discussed herein.

A "crystallite" is a region within a particle of local crystalline order. Each active nickel particle comprises a large number of crystallites.

The term "crystallite size" as used herein refers to an average diameter for a possibly irregularly-shaped crystallite. Crystallite size can be measured as a diameter of the crystallite, for example, along the crystallite's major dimension, or as the cube root of the volume of the crystallite. The crystallite size can be determined by x-ray diffraction (XRD) analysis using procedures and equipment available in the art. An "average crystallite size" or "mean crystallite size" refers to an average (mean) value for a population of crystallite sizes as defined above. An average crystallite size can also be defined as the cube root of the average volume of a sample comprising multiple crystallites, and assumes that all crystallites have the same size and shape. For a distribution of sizes, the mean size can be defined as the mean value of the cube roots of the individual crystallite volumes or the cube root of the mean value of the volumes of the individual crystallites.

The term "C10" is a measure of crystallite sizes in the nickel particulate form, and refers to the largest diameter (e.g., in nanometers) that the smallest 10% of crystallites have in the nickel particulate form. The term "C50" is also a measure of crystallite sizes in the nickel particulate form, and refers to a diameter (size) wherein 50% of the Ni crystallites in a bulk sample have a size less than the stated value. The C50 value is also referred to herein as the mean crystallite size (MCS). The term "C90" is also a measure of crystallite sizes in the nickel particulate form, and refers to a diameter (size) wherein 90% of the nickel crystallites in a bulk sample have a size less than the stated value. Cx is the size of the crystallite for which x% of the sample has a smaller size. Crystallite size can be measured using X-ray diffraction (XRD).

The term "crystallite size distribution span" as used herein refers to a statistical value denoting a spread in crystallite size defined as (C90-C10)/C50.

A "surface crystallite" as the term is used herein refers to a crystallite contained within a particle, but wherein a portion of the crystallite is exposed to the environment surrounding the particle, such as an organic liquid containing a ligand. To calculate BET SSA/crystallite size ratios, the equations BET SSA/$4\pi(C50/2)^2$ for spherical crystallites and BET SSA/$C50^2$ for cuboidal crystallites (cross section of cubes) can be used.

A surface crystallite "edge" as the term is used herein refers to those surface portions of a crystallite that are not planar surfaces.

Though the shape of crystallites is usually irregular, the shapes can often be described as being spherical, cuboidal, tetrahedral, octahedral, or parallelepipeds such as needles or plates, prisms or cylinders. Most applications of Scherrer analysis assume spherical crystallite shapes. If the average crystallite shape is known from another analysis, a proper value can be selected for the Scherrer constant K. Anistropic peak shapes can be identified by anistropic peak broadening if the dimensions of a crystallite are 2x*2y*200z, then (h00) and (0k0) peaks will be more broadened then (001) peaks. Also, see the discussion at this website: clays.org/journal/archive/volume%2047/47-6-742.pdf, published as M. Crosa, et al. (1999), "Determination of Mean Crystallite Dimensions from X-Ray Diffraction Peak Profiles: A Comparative Analysis of Synthetic Hematites", *Clays and Clay Materials*, 47(6), 742-747, and references contained therein, which reference and cited references are incorporated herein by reference in their entireties. The average number of crystallites per unit mass is expressed as the number of crystallites per gram of the nickel form, and any assumptions made about crystallite shape in carrying out the calculations are stated.

The term "D10" is a measure of particle sizes in a nickel particulate form, and refers to the largest diameter (e.g., in microns) that the smallest 10% of nickel particles have in the nickel particulate form.

A "Ni particle" is a discrete particle or agglomerated particle, typically visible in a scanning electron micrograph.

The term "particle size" as used herein refers to an average diameter of a possibly irregularly-shaped particle. Such a particle size can be determined by measurement with a Mastersizer 2000 Particle Size Analyser from Malvern Instruments Ltd using the Hydro 2000MU accessory and water as the dispersant, as is well known in the art. An "average particle size" or "mean particle size" refers to an average (mean) value for a population of particle sizes as defined above. For sizes below 100-200 microns the average particle size can be measured using a laser diffraction technique.

Standard abbreviations for chemical groups such as are well known in the art can be used herein, and are within ordinary knowledge; e.g., Me=methyl, Et=ethyl, i-Pr=isopropyl, Bu=butyl, t-Bu=tert-butyl, Ph=phenyl, Bn=benzyl, Ac=acetyl, Bz=benzoyl, and the like.

Provisos can apply to any of the disclosed categories or groups, wherein any one or more of the other above disclosed categories, groups or species can be excluded from such categories or groups.

The term "room temperature" as used herein refers to ambient temperature, which can be, for example, between about 16° C. and about 27° C.

"Substantially spherical" refers to particles or crystallites that are substantially symmetrical around a center point. For example, while the distance (radius) from a center point to the surface of a substantially spherical particle or crystallite can vary, such variation is not so great or so predictable that the shape of the substantially spherical particle or crystallite would more accurately be defined as another geometric shape (e.g., as a cube instead of as a sphere). In some embodiments, the substantially spherical particle or crystallite can have a radius that varies by about up to about 25%, or up to about 20%, or up to about 15%, or up to about 10%, or up to about 5%. In some embodiments, the substantially spherical particle or crystallite can be partially spherical. For example, the substantially spherical particle or crystallite can be hemispherical, or be a quarter of a sphere. The substantially spherical crystallite can be fused to a particle or another crystallite such that the substantially spherical crystallite is a partial, substantially spherical projection from the particle or other crystallite. A partially substantially spherical crystallite that is fused to a particle or another crystallite can therefore be about 25% to about 95% of a sphere, or any percentage of a sphere between 25% and 95%.

The Scherrer method (using full width at half maximum, FWHM, method) gives the ratio of the root-mean-fourth-power to the root-mean-square value of the thickness. The Stokes and Wilson method (using integral breadth) determines the volume average of the thickness of the crystallites measured perpendicular to the reflecting plane. The variance methods give the ratio of the total volume of the crystallites to the total area of their projection on a plane parallel to the reflecting planes.

All values shown as % or ppm (parts per million) are intended to be by weight, unless otherwise specifically stated (e.g., as volume %). In other words, a numerical percentage or a numerical parts per million is that numerical percentage or parts per million by weight of the total composition (unless otherwise specified).

As used herein, "substantially" refers to a majority of, or mostly, as in at least about 80%, 90%, 95%, 96%, 97%, 98%, 99%, 99.5%, 99.9%, 99.99%, 99.999%, or at least about 99.9999%.

The following Examples illustrate aspects of the invention.

Example 1

Assays for Nickel-Ligand Complex Formation and Ni & S Content

This Example describes assays employed to evaluate the activity of nickel metal samples for forming a complex with phosphorus-containing ligands, as well as assays to determine the content of nickel and sulfur in various basic nickel carbonate, nickel oxide, nickel metal etc. samples.

To evaluate the suitability of nickel preparations for generating hydrocyanation catalysts, the nickel is mixed with a phosphorus-containing ligand (e.g., Ligand (V)) in a 3-pentenenitrile (3PN) solution and warmed for a period of hours and the level of solubilized nickel in solution is measured by liquid chromatography (LC) over time in the assay described below. In general, the goal is to identify nickel preparations that form complexes with phosphorus-containing ligands at a rate suitable for use in a manufacturing process involving a hydrocyanation catalyst. For example, a suitable nickel preparation forms sufficient nickel-ligand complex and/or reaches an equilibrium in nickel metal phosphorus ligand complex formation assay in no more than about 2 hours, no more than 1 hour, or no more than 30 minutes. Preferably, equilibrium is reached in no more than 30 minutes.

Nickel-Ligand Complex Formation Assay Procedure

For assays of nickel metal complex formation with phosphorus-containing ligands, the nickel metal is handled in a dry, nitrogen atmosphere. The assay for complex formation is performed as follows: a reactor bottle is charged with 80 gram of a 5% by weight Ligand V solution in 3-pentenenitrile (3PN) solvent, 3.2 gram of the nickel metal (Ni(0)), and 0.5 gram of anhydrous $ZnCl_2$. The reactor bottle is sealed, removed from the dry box, and moved to a laboratory fume hood where it is placed on a magnetic stir plate. The reaction mixture within the reaction bottle is then heated to 60° C. In some tests the assay mixture is heated to 80° C. The reaction mixture is mixed to maintain the nickel-containing solid in suspension. Filtered liquid samples are withdrawn as a function of time and analyzed for soluble nickel concentration by liquid chromatography.

In some tests, nickel prepared from MetChem BNC (described in Table 1) is used as a control, where the activity of the MetChem nickel is deemed to be 1.0 and nickel metal samples that form soluble complexes with Ligand V at a greater rate exhibit improved nickel activity. Nickel samples are also deemed to be minimally active if soluble nickel (in a complex with Ligand V) forms at a minimal rate of at least 317 ppm/hr at 60° C. or at a rate of at least 980 ppm/hr at 80° C.

An empirical rate equation for Ni dissolution in catalyst-preparation assay is employed to provide a numerical value indicative of nickel 'activity' (ability to become a soluble catalyst complex with Ligand (V)) in the following reaction:

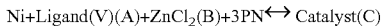

The following equation describes the rate of Nickel-Ligand (V) catalyst formation:

$$r = a \cdot k' \cdot w_{Ni} \cdot C_A^{a'} \cdot C_B^{b} \cdot [1 - C_c/(K_{eq} \cdot C_A \cdot C_B)] \cdot 2 \cdot (C_A/C_{A0})/[1+(C_A/C_{A0})]$$

where:
- a = activity of nickel
- $w_{Ni}$ = weight loading of nickel (weight of nickel/weight of solution)
- k' = Arrhenius rate constant:

$$[(\text{mmoles Ni/liter})^{0.5}/\text{hr}] = 1.539 \times 10^{10} \exp[-6832.1/T(K)]$$

- $C_A$ = concentration of Ligand (V) (mmol/L)
- $C_{A0}$ = Initial concentration of Ligand (V) (mmol/L)
- $C_B$ = concentration of $ZnCl_2$ (mmol/L)
- a' = order of reaction with respect to Ligand (V) = 0
- b = order of reaction with respect to $ZnCl_2$ = 0.5
- $K_{eq}$ = equilibrium constant for the chemical reaction $$[\text{liters/mmol}] = \exp[11555/T(K) - 35.231]$$

T = temperature in degree Kelvin.

It is assumed that the 3-pentenenitrile is in far excess so its order of reaction with respect to the rate of 3-pentenenitrile dissolution is considered zero. The order of reaction with nickel loading is considered to be 1.

The rate constant k' is defined for a standard MetChem BNC reduced at 400° C. under pure hydrogen to nickel. However, to account for other sources of nickel that can have different in properties, a factor is applied that is termed the activity of nickel dissolution. The 'activity' number was chosen to be 1 for the specific condition of MetChem BNC reduced at 400° C. to nickel, dissolved at 80° C. in the catalyst-preparation solution with $ZnCl_2$/Ligand (V) molar ratio of 0.8 and 4 wt % nickel loading where dissolution is at a rate of 980 ppm Ni/hr. In principle, a higher activity is essentially a higher rate constant specific to a given nickel. In order to move away from separately determining rate constant for each type of nickel, the activity term is defined to get around this issue.

Note that if recrystallized Ligand (V) is employed in the assay, the measured nickel activity is higher than if an extracted (e.g., recycled) Ligand (V) preparation is employed. The difference in activity is about 2-fold.

Sulfur Content Assay Procedures

Sulfur content in basic nickel carbonate, nickel oxide, nickel metal and other nickel sources was measured by combustion with infrared (IR) spectroscopy analysis, microcoulometry, or inductively coupled plasma (ICP) mass spectrometry.

For combustion IR detection, 0.2-0.5 g BNC/NiO/Ni etc. samples are weighed into boats, the boats are introduced into a furnace, the samples are heated (1350° C.) in a steam of oxygen. The combustion gases are scrubbed to remove moisture and swept into the infrared detection cell. The amount of sulfur detected is converted to total sulfur in the sample using the stored calibration curve and the known sample weight. The samples are analyzed in duplicate with the mean value reported. The limit of detection is around 20 ppm. Instrument uncertainty is 5% relative or better.

Microcoulometry is a more sensitive technique than combustion IR detection. Microcoulometry also uses combustion with the formation and measurement of $SO_2$. Sample weight for microcoulometry is normally around 20-50 mg. Samples are introduced into a furnace at 1100° C. Combustion gases are scrubbed to remove moisture and to cool the gases before the gases are introduced into an equilibrated coulometric titration cell. Sulfur is detected by reaction of the $SO_2$ formed with $I^3$ to form $I^-$ and $SO_4$, and calculated from the charge needed to rebalance the cell. The limits of detection for microcoulometry can be less than 1 ppm although levels only as low as 1 ppm are quoted and the instrument uncertainty is 5% or less.

Nickel Content Assay Procedures

The nickel content of samples described in Examples 2-4 was determined by inductively coupled plasma optical emission spectrometry (ICP-OES), while the nickel content of the samples described in Examples 5 and 6 was determined by thermogravimetric analysis (TGA).

Samples (20-50 mg) are evaluated for nickel content in a Perkin Elmer TGA4000 thermogravimetric analyzer by heating the sample from 30 to 995° C. at a rate of 50° C./min in a nitrogen atmosphere with a flow rate of 40 mL/min. The water content is characterized by the first thermal event (first weight loss) and the nickel content by the final total weight loss observed at 995° C. where all the material has been fully decomposed to NiO.

Unless specified, the analytical data provided below for the various nickel metal preparations (e.g., regarding sulfur content, BET, XRD data etc.) is for a reduced passivated nickel preparation that has a thin NiO coating. Such passivation occurs as the nickel becomes exposed to oxygen during performance of the analytical techniques employed. It is assumed that such passivation (i.e. the amount of NiO on the surface) has a negligible impact on the analytical results.

Carbonate Content

Carbonate content is determined using the method described by Donald L. Pile et al. in Journal of Chemical Education, LA-UR-97-1384, "A Precise Method for Determining the $CO_2$ Content of Carbonate Materials." The technique uses a simple apparatus designed to measure the volume change originating from $CO_2$ gas formed by a reaction of the BNC sample and a solution of hydrochloric acid.

Example 2

Nickel Activity Varies with BNC Sample Type

Eight basic nickel carbonate (BNC) samples are evaluated for suitability in preparing Ni metals. All samples tested are commercial products with the exception of BNC #5, which is prepared according the BNC precipitation procedure described above. As described below different particulate nickel metal preparations made from different BNC sources exhibit variability in complex formation with phosphorus-containing ligands.

Table 1 (above) and Table 2 provide analytical data concerning trace impurities in the BNC samples. All percentage and parts per million (ppm) values are weight:weight (w/w), unless otherwise stated.

TABLE 2

Samples of Basic Nickel Carbonate Evaluated for Preparation of Inventive Ni Form

| BNC No. | C % | H % | N % | S ppm | Cl ppm | Nickel % | $CO_3^{2-}$ % | Ni:C Wt Ratio | Ni:C Mole Ratio |
|---|---|---|---|---|---|---|---|---|---|
| 1 | 3.9 | 3.3 | 0.09 | 212 | 13 | 42.08 | 19.5 | 10.79 | 2.21 |
| 2 | 4.6 | 2 | 0.08 | 1902 | 3 | 50.71 | 23 | 11.02 | 2.26 |
| 3 | 6.4 | 2.2 | 0.02 | 5 | 9 | 45.33 | 32 | 7.08 | 1.45 |
| 4 | 4.8 | 2.4 | <0.02 | 7 | <1 | 46.19 | 24 | 9.62 | 1.97 |
| 5 | 4.5 | 2.1 | <0.02 | 21000 | 7 | 51.57 | 22.5 | 11.46 | 2.35 |
| 6 | 5.6 | 2.4 | <0.02 | 10 | 2 | 45.53 | 28 | 8.13 | 1.66 |

TABLE 2-continued

Samples of Basic Nickel Carbonate Evaluated for Preparation of Inventive Ni Form

| BNC No. | C % | H % | N % | S ppm | Cl ppm | Nickel % | $CO_3^{2-}$ % | Ni:C Wt Ratio | Ni:C Mole Ratio |
|---|---|---|---|---|---|---|---|---|---|
| 7 | 3.3 | 3.3 | <0.02 | 9800 | 3 | 45.15 | 16.5 | 13.68 | 2.80 |
| 8 | 4.5 | 2.7 | <0.02 | 4600 | 3 | 46.44 | 22.5 | 10.32 | 2.11 |

Exemplary Procedure for Production of Ni Powders

For conversion of the above-listed BNC samples to Ni powders and evaluation of those Ni powders for activity in the reaction with the test phosphite ligand, ligand (V), in the organic liquid 3PN, the following procedures can be used.

Calcination pretreatment can be employed, such as with air flow, optionally including steam, prior to the step of reduction. Fifteen grams of the dried solid BNC sample are placed inside a reaction tube that can be heated within an electrical furnace located in a lab fume hood. Calcination can be carried out in the 300-400° C. temperature range. FIG. 1 shows $CO_2$ loss during calcination pre-treatment of the eight BNC samples numbers 1-8, whose properties are shown in Table 2.

Calcination pretreatment is not essential because the BNC can be simultaneously calcined while the nickel in the BNC is reduced. For example, a sample of BNC, listed as BNC #1 in Table 2 above that is supplied by MetChem (an American distributor of BNC), is reduced without calcination. Fifty grams of BNC #1 material is reduced in hydrogen at a flow rate of 0.5 liter $H_2$/min at 400° C. for four hours. The reduction is done in a temperature controlled tube furnace. The reduction tube is taken into a dry box and the contents transferred to a bottle. The resulting powder is magnetic, indicating that nickel metal is produced by the reduction.

BNC samples #2-8 in Table 2, above, are processed in a similar manner, except that a calcination pretreatment is also employed, to provide the Ni-containing powders for evaluation for zero-valent nickel phosphorus ligand preparation as described in Example 1.

Product Properties

It has been found that some BNC samples are more suitable for preparation of nickel particulate compositions of the invention than are other samples. Data presented herein and in the Figures illustrate the properties of BNC samples during and after processing to show when a particular sample will be a nickel active inventive particulate form of zero-valent nickel metal.

As noted above, BNC samples 2-8 are subjected to calcination, but BNC sample 1 is not. However, all eight samples are reduced via hydrogenation. The characteristics of nickel preparations generated from the eight reduced BNC samples are shown in Table 3. Nickel samples 1-8 in Table 3 are prepared from the corresponding BNC samples 1-8 listed in Table 2.

In Table 3, "Ni active" means that the Ni metal prepared by reduction from the corresponding BNC is better than, BNC sample #1, the Ni powder obtained from the MetChem BNC via a one-step reduction process (i.e., not including calcination pretreatment). Sample 1 has nickel activity barely sufficient to enable the efficient preparation of the zero-valent nickel phosphorus ligand complexes suitable for use as a hydrocyanation catalyst. By efficient preparation is meant that the nickel powder reacts with sufficient completeness and at a sufficient rate to be economically suitable for use in carrying out industrial-scale olefin hydrocyanation reactions, such as the hydrocyanation of 3PN to form adiponitrile (ADN), an important intermediate in the manufacture of various nylons such as Nylon 6 and Nylon 6,6.

TABLE 3

Nickel Sample Properties

| BNC No | Active Ni | Mean Ni Crystal Size (nm) |
|---|---|---|
| 1 | Yes | 31 |
| 2 | Yes | 21 |
| 3 | No | 80 |
| 4 | No | 40 |
| 5 | Yes | 28 |
| 6 | No | 47 |
| 7 | Yes | 27 |
| 8 | Yes | 21 |

In Table 3, samples marked "yes" have active nickel while samples 3, 4 and 6 do not have active nickel as assessed by assays involving nickel-phosphorus ligand complex formation useful for catalysis of industrial-scale olefin hydrocyanation reactions. A relationship between mean (average) crystallite size and activity is also apparent from the data in Table 3. The three samples judged to be insufficiently active for zero-valent nickel bidentate ligand catalyst preparation, sample numbers 3, 4, and 6, have the three largest average crystallite sizes among the eight samples tested, as determined by XRD. All active samples have mean crystallite sizes of about 30 nm or less.

Example 3

BNC Physical and Chemical Properties

"Ni active" samples 2, 5, 7, and 8 described in Example 1 are further evaluated and compared to samples 3, 4 and 6 that do not have sufficient active nickel for efficient formation of nickel phosphorus ligand complexes, and that have larger crystallite mean size than the active samples.

Analytical Procedures—Methodology

TP-XRD Measurements

A Siemens Bruker D5000 diffractometer with Anton Paar HTK heating stage is used. The BNC specimens are mounted as a dry compacted layer on a platinum (Pt) foil, itself attached to an electrically heated Pt bar. A gas flow of 4% $H_2/N_2$ is used.

A pre-heating scan at room temperature is obtained from the starting material; this also allows the system to flush fully with $H_2/N_2$. Following the heating profile a room temperature scan of the product is obtained for reference.

The following measurement conditions are used.

| | |
|---|---|
| Diffractometer | Siemens/Bruker D5000 D7 |
| X-ray Tube | Cu LFF |
| Radiation | Cu Kα |
| Generator Voltage | 40 kV |
| Generator Current | 40 mA |
| Diffraction Geometry | Reflection Bragg Brentano |
| Variable Divergence Slit | 6 mm irradiated length |
| Antiscatter Slit | 2 mm irradiated length |
| Receiving Slit | 0.6 mm |
| Primary soller slit | 2.3° |
| Secondary soller slit | — |
| Detector | Scint |
| Monochromator | Graphite Monochromator |
| Filter | — |

-continued

| Diffractometer | Siemens/Bruker D5000 D7 |
|---|---|
| Pre-Heating | |
| Step Size | 0.05° |
| Time per step | 2 s |
| Scan start angle | 5° |
| Scan finish angle | 90° |
| Specimen format | Compressed Dry powder |
| Specimen loading | Top compression |
| Temperature | Room temperature |
| Temperature Ramp rate | — |
| Atmosphere | 40 cm3/min 4% $H_2/N_2$ |
| Heating Profile | |
| Step Size | 0.02° |
| Time per step | 3 s |
| Scan start angle | 38° |
| Scan finish angle | 106° |
| Specimen format | Compressed Dry powder |
| Specimen loading | Top compression |
| Temperature | 100° C. then 160-420° C. in 20 C. intervals |
| Temperature Ramp rate | 0.5 C./s |
| Atmosphere | 40 cm³/min 4% $H_2/N_2$ |
| Post Heating | |
| Step Size | 0.02° |
| Time per step | 2 s |
| Scan start angle | 30° |
| Scan finish angle | 108° |
| Specimen format | Compressed Dry powder |
| Specimen loading | Top compression |
| Temperature | Room temperature |
| Temperature Ramp rate | — |
| Atmosphere | 40 cm3/min 4% $H_2/N_2$ |

Instrument profile parameters can be determined from a NIST lanthanum hexaboride diffraction pattern. Line profile analysis can determine the additional broadening present in each diffraction peak.

Reduction and Microstructure Monitoring

Diffraction patterns are analysed using the Wilton "LOSS" software, which optimises the fit of a simulated diffraction pattern comprising a set of peak profiles calculated for a series of crystallite sizes. The crystallite size values obtained are volume-weighted means. The data is further analysed using a "Williamson Hall" plot to separate crystallite size broadening from lattice distortion broadening, if present. The presence of faulting in the cubic metal structure can be examined by comparison of the width of the line profiles of the 111 and 200 reflections.

Reaction progress can be calculated from the areas associated with the Ni metal peaks and from a pattern of the unreduced BNC material as observed in lower temperature diffraction patterns. This BNC pattern can be fitted by the LOSS program together with the simulated Ni peaks and simulated peaks corresponding to the Pt specimen carrier.

TPR-MS & TPD-MS Measurement

Temperature-programmed reaction mass spectroscopy (TPR-MS) and/or temperature-programmed desorption-reaction-mass spectrometric (TPD-TPR MS) studies are performed using where the test conditions can be as follows:

Test Conditions TPD-MS (See FIG. 3B):
Ar Balance (20 cm³ min⁻¹, >99% Ar, BOC)
Total Flow Rate=20 cm³ min⁻¹
Internal Standard=Ar (m/z=36)
Catalyst Mass=50-60 mg
Rate=15° C. min⁻¹
Test Conditions TPR-MS (see FIG. 3C):
10% $H_2$ (2 cm³ min⁻¹, >99% $H_2$, BOC)
Ar Balance (18 cm³ min⁻¹, >99% Ar, BOC)
Total Flow Rate=20 cm³ min⁻¹
Internal Standard=Ar (m/z=36)
Catalyst Mass=50-60 mg
Rate=15° C. min⁻¹

Analytical Results and Discussion

Data are collected during the conversion of the eight BNC samples shown in Table 2 to the nickel metal powders to evaluate which BNC samples have suitable or unsuitable, properties for efficient conversion to zero-valent nickel/bidentate phosphite ligand complexes. For example, such data can provide additional information as to how variables such as crystallite mean size and SSA (BET and LD) affect the ability of the nickel preparations to form soluble zero-valent nickel-ligand complexes.

In the process of conversion of BNC to Ni powders, reduction must be employed but calcination is optional prior to the reduction step. Calcination can be carried out by the usual means known in the art, such as in a fluidized bed reactor, a rotary furnace, or the like, as discussed above.

Data is collected during the calcination of each of the eight BNC samples (see Tables 1, 2, and 3) and after conversion to particulate Ni samples to assess the suitability of the product as an active Ni composition. Samples 2, 5, 7, and 8 are found to be active Ni (Table 3), defined herein as being suitable for complex formation with ligands, such as with bidentate phosphite ligands, while samples 3, 4, and 6 are found to be unsuitable, as well as not meeting the structural/functional criteria defined herein for Ni powders of the invention with respect to SSA and crystallite mean size.

FIG. 1 shows a Thermal Programmed Desorption scan of each of the eight BNC samples listed in Table 2 at calcining temperatures in an argon atmosphere over the temperature range indicated, with detection of $CO_2$ by mass spectroscopy. TPD (also known as TDS) involves heating a sample while it is contained in a vacuum and simultaneously detecting the residual gas in the vacuum by means of a mass analyzer. As the temperature rises, certain absorbed species will have enough energy to escape and will be detected as a rise in pressure for a certain mass.

FIG. 1 shows that inactive BNC #3 releases the largest amount of $CO_2$ during calcining while active BNC samples 5 and 7 release the least amount of $CO_2$ during calcining. Active Ni samples prepared from BNC #2, 5, 7, and 8 also tend to have smaller crystallite mean size (e.g., less than about 30 nm) than the inactive nickel samples made from inactive BNC samples #3, 4 and 6. These data suggest that BNC samples that are more readily calcined can, at least in some instances, produce a Ni particulate form with good activity and the desirable structural features.

Further processing via hydrogenation illuminates additional characteristics of active Ni versus inactive Ni. Such hydrogenation reduces the BNC (or NiO if a calcination pre-treatment is applied) to Ni metal.

Figure 2:
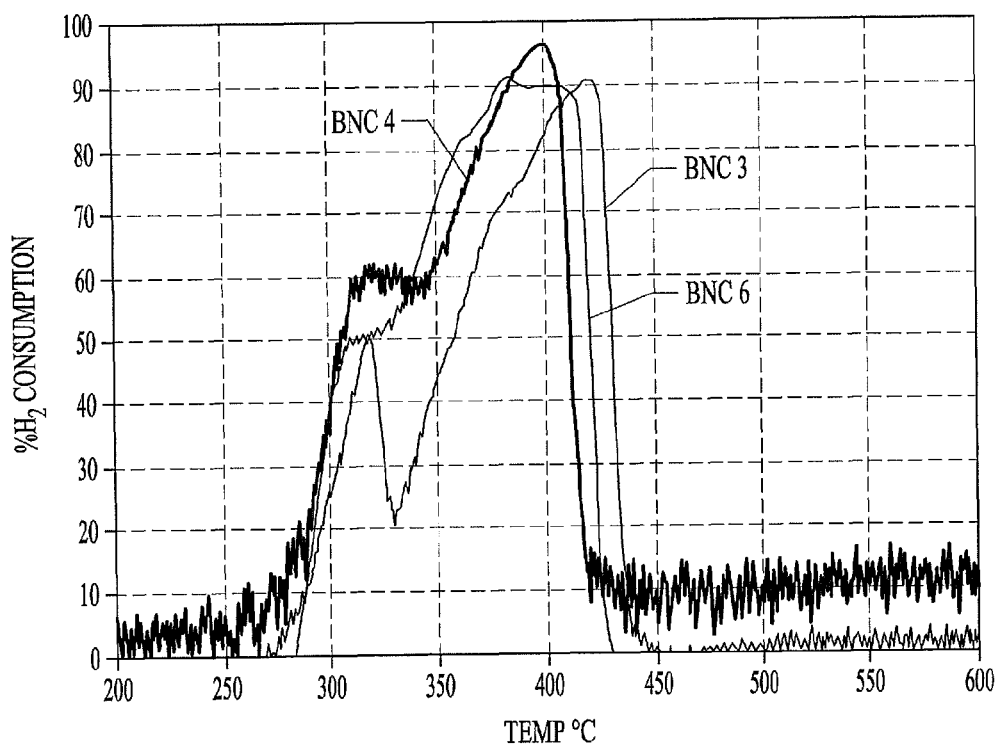
FIG. 2 is a thermal profile of hydrogen absorption during reduction of BNC samples #3, 4, and 6, which upon reduction provide inactive Ni that does not efficiently form complexes with phosphorus-containing ligands as described herein.

FIGS. 2 and 3 show the disparate hydrogen absorption profiles observed in the processing of the precursors yielding inactive Ni and in the processing of the precursors that yield active Ni, respectively.

As can be seen in FIG. 2, the BNC samples #3, 4, and 6 of Table 2, which yield inactive Ni samples upon reduction, exhibit a distinct pattern of two maxima of hydrogen absorption of unequal size, a smaller absorption maximum around 300° and a larger one around 400° C.

Figure 3A:
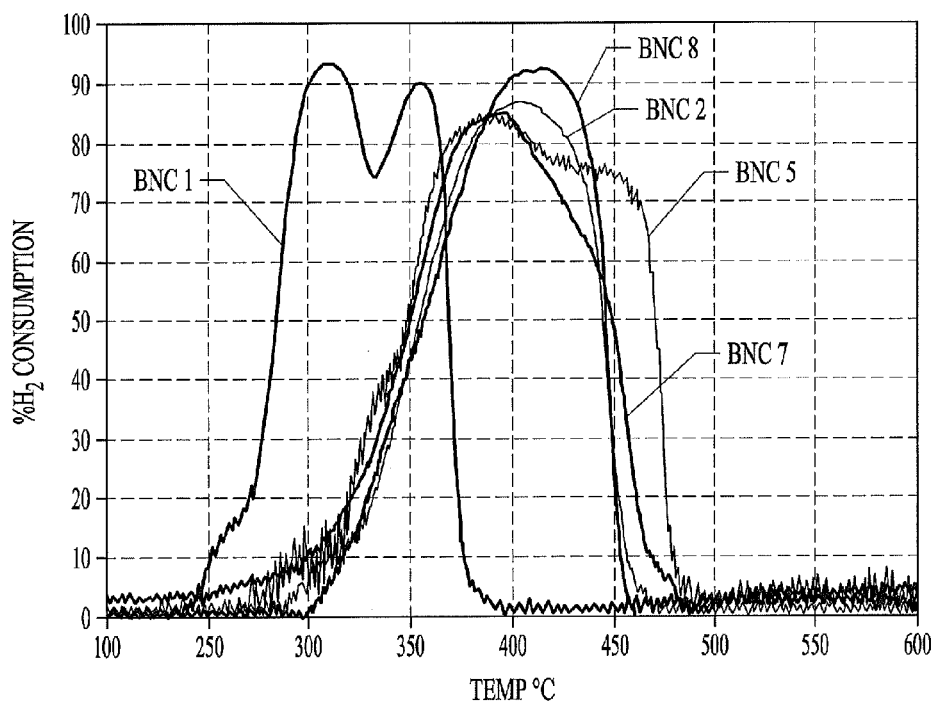
FIG. 3A is a thermal profile of hydrogen absorption during reduction of BNC samples #1, 2, 5, 7, and 8, which upon reduction provide active Ni that does efficiently complexes with phosphorus-containing ligands as described herein.
Figure 3B:
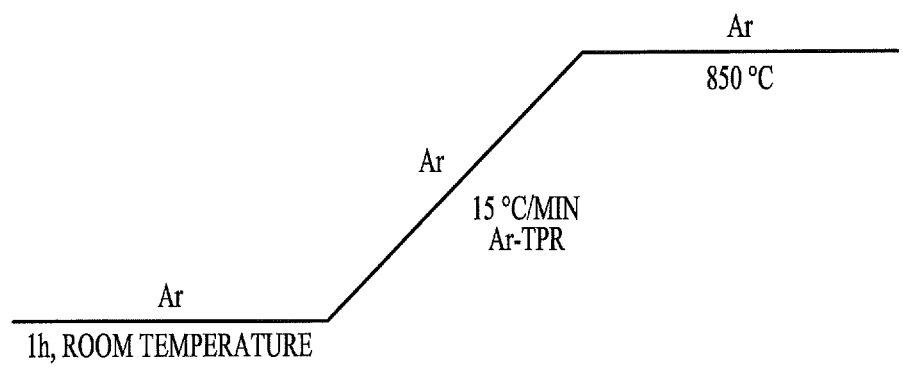
FIG. 3B shows temperature-programmed desorption-reaction-mass spectroscopy (TPD-TPR MS) where the Test Conditions are Ar Balance (20 cm3 min−1, >99% Ar, BOC); Total Flow Rate=20 $cm^3$ $min^{-1}$; Internal Standard=Ar (m/z=36); Catalyst Mass=50-60 mg; Rate=15° C. $min^{-1}$.
Figure 3C:
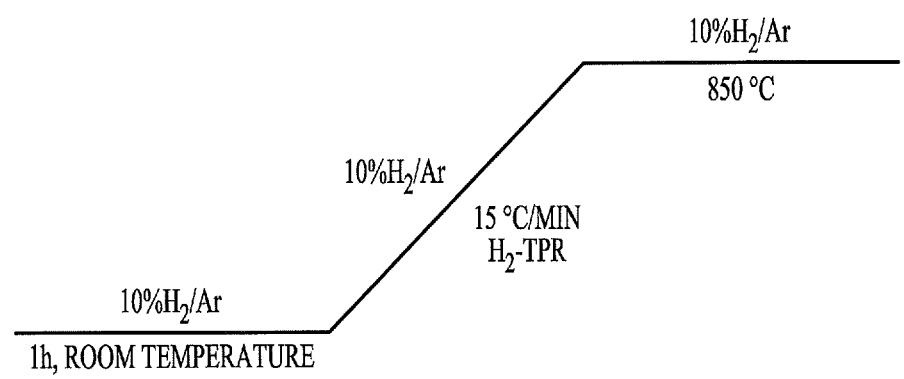
FIG. 3C shows temperature-programmed reaction mass spectroscopy (TPR-MS) where the Test Conditions are 10% $H_2$ (2 $cm^3$ $min^{-1}$, >99% $H_2$, BOC); Ar Balance (18 $cm^3$ $min^{-1}$, >99% Ar, BOC); Total Flow Rate=20 $cm^3$ $min^{-1}$; Internal Standard=Ar (m/z=36); Catalyst Mass=50-60 mg; Rate=15° C. $min^{-1}$.
Figure 4:
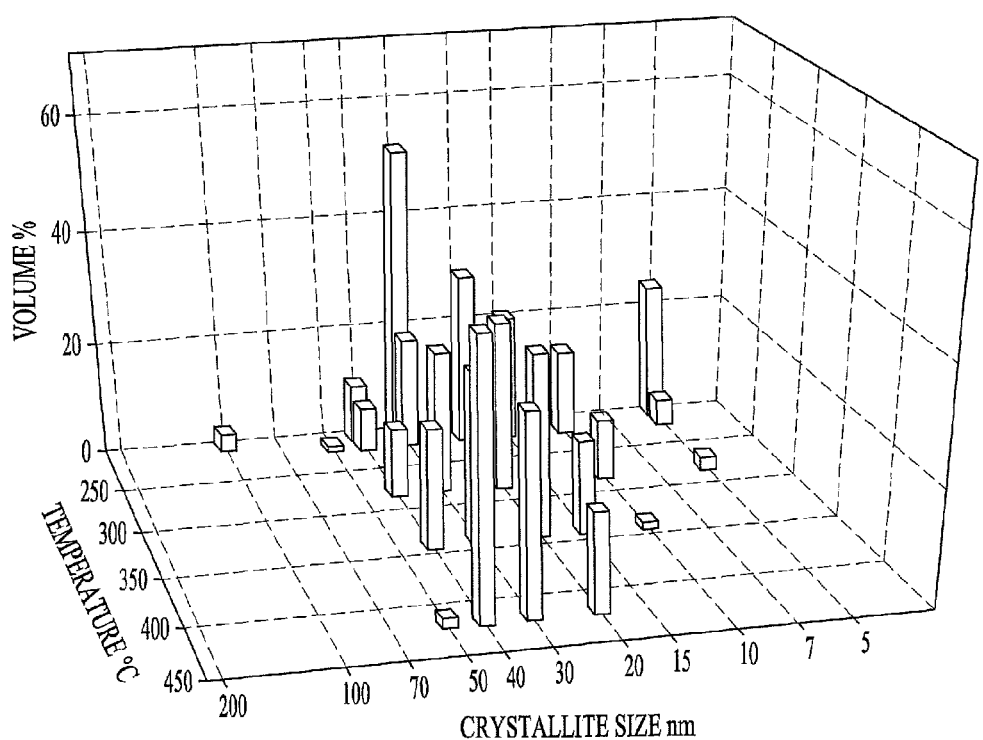
FIG. 4 shows TP-XRD data for a Ni metal particulate form obtained by hydrogen reduction of BNC sample #1 listed in Table 2. The temperature axis shows the progression of increasing temperature applied during the hydrogenation process, the crystallite size axis shows crystallite sizes, as determined by XRD in these data, and the volume-% axis indicates the distribution by volume of the various crystallite size classes in each bulk sample. Sample numbering corresponds to that shown in Table 2. See also, Example 3.
Figure 5:
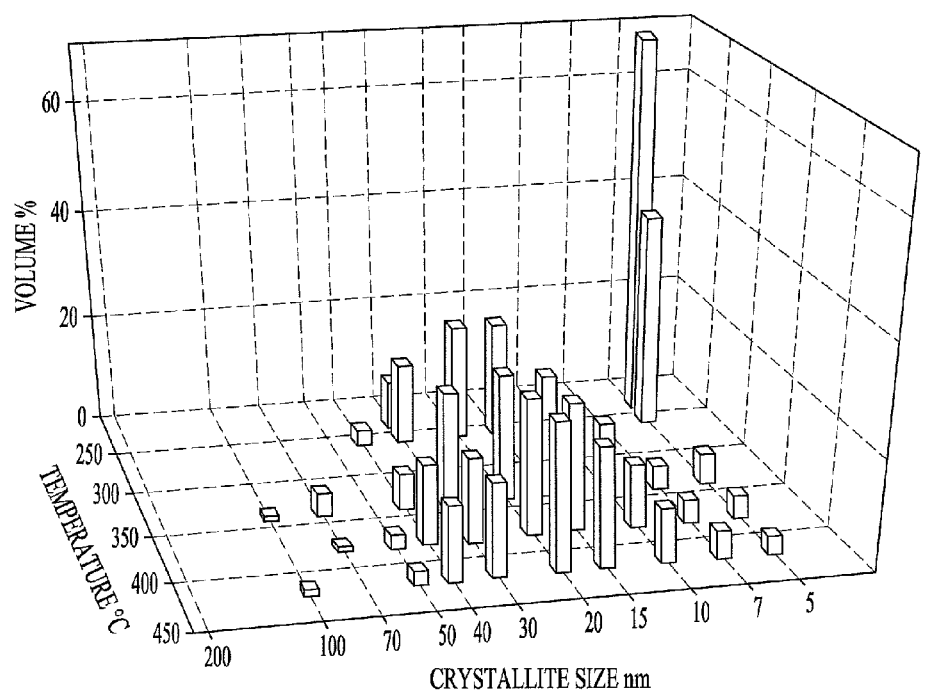
FIG. 5 shows TP-XRD data for a Ni metal particulate form obtained by hydrogen reduction of BNC sample #2 listed in Table 2. The graph was generated as described in Example 3 and for FIG. 4.
Figure 6:
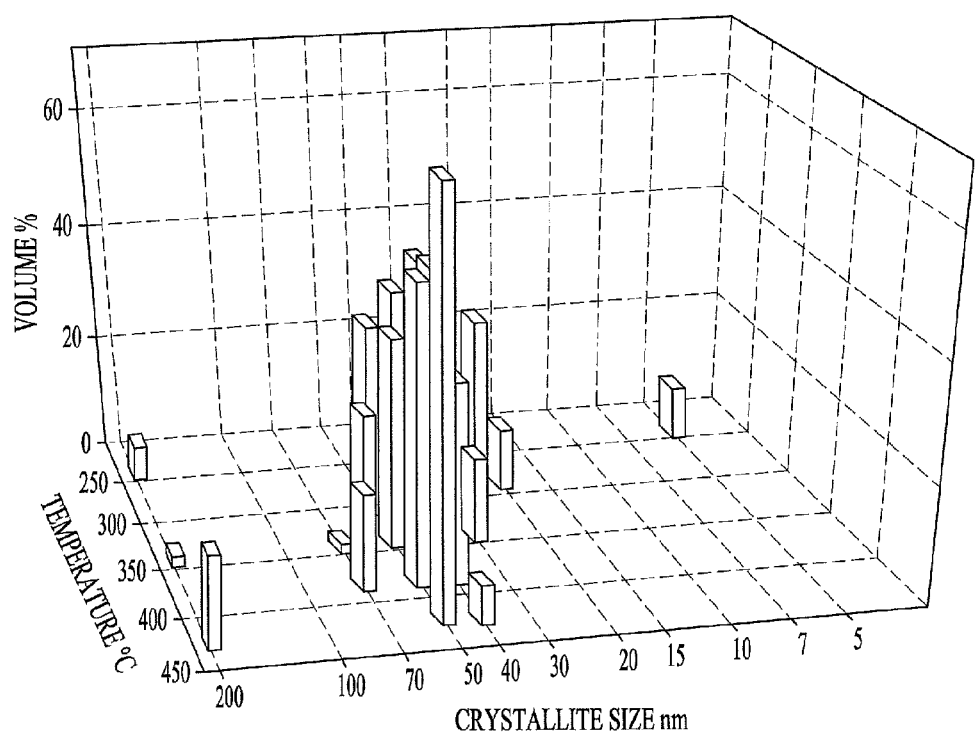
FIG. 6 shows TP-XRD data for a Ni metal particulate form obtained by hydrogen reduction of BNC sample #3 listed in Table 2. The graph was generated as described in Example 3 and for FIG. 4.
Figure 7:
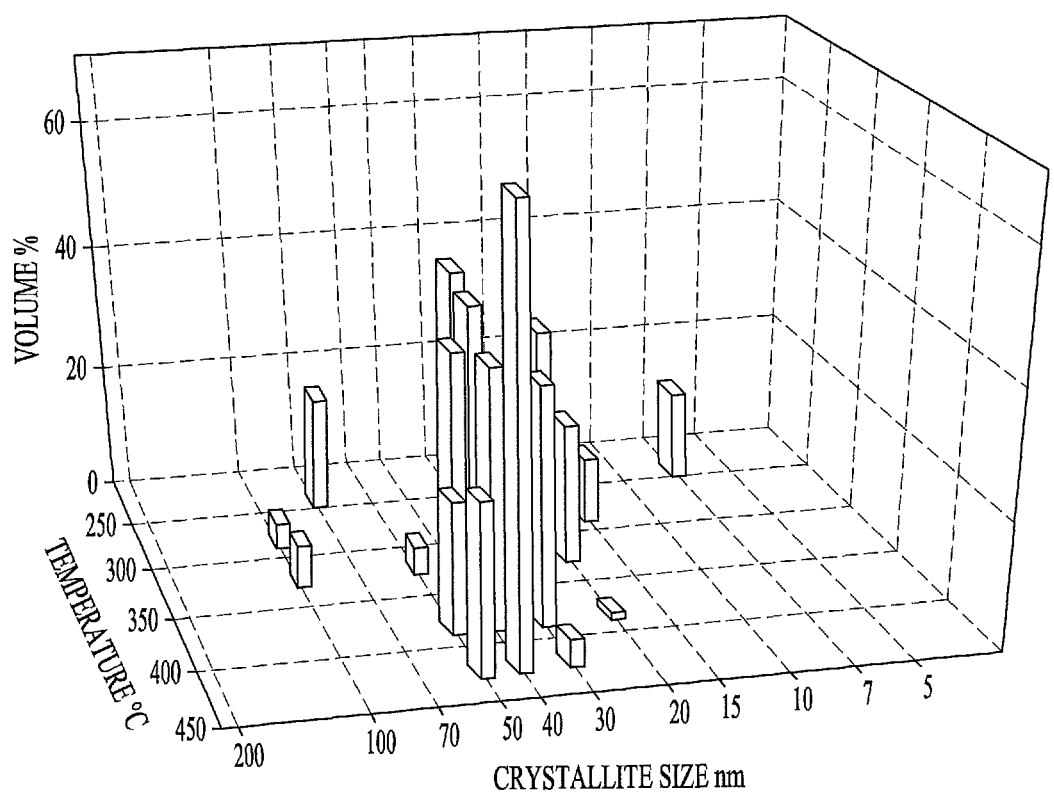
FIG. 7 shows TP-XRD data for a Ni metal particulate form obtained by hydrogen reduction of BNC sample #4 listed in Table 2. The graph was generated as described in Example 3 and for FIG. 4.
Figure 8:
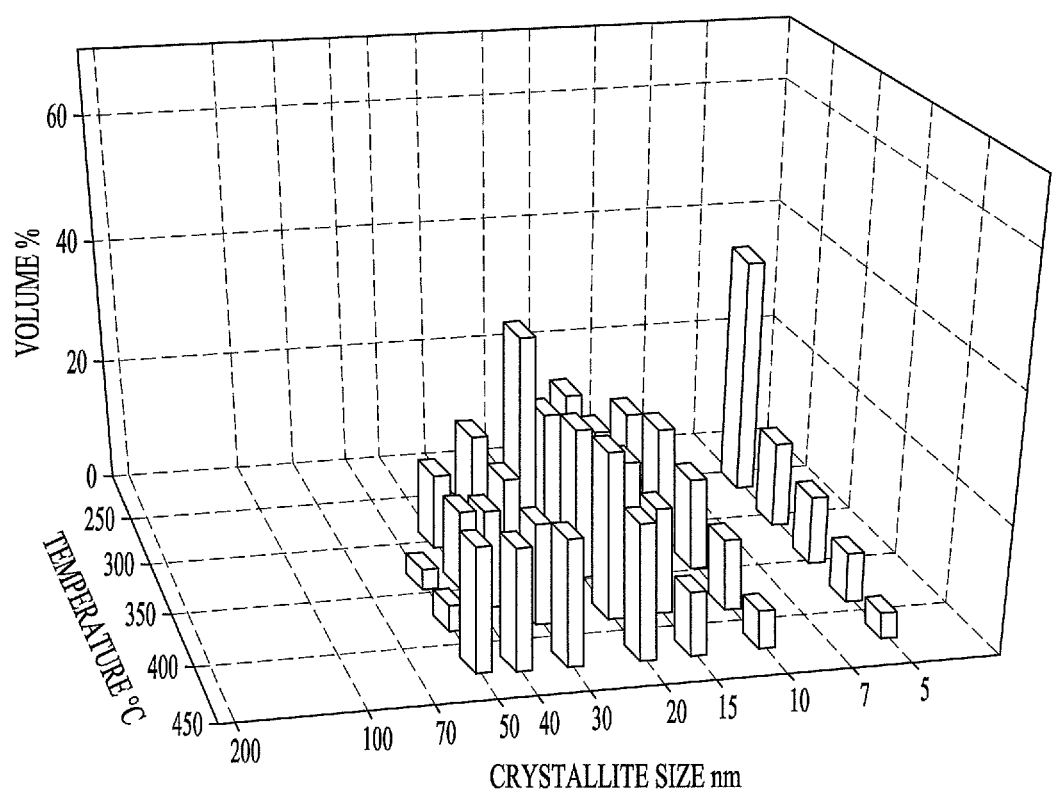
FIG. 8 shows TP-XRD data for a Ni metal particulate form obtained by hydrogen reduction of BNC sample #5 listed in Table 2. The graph was generated as described in Example 3 and for FIG. 4.
Figure 9:
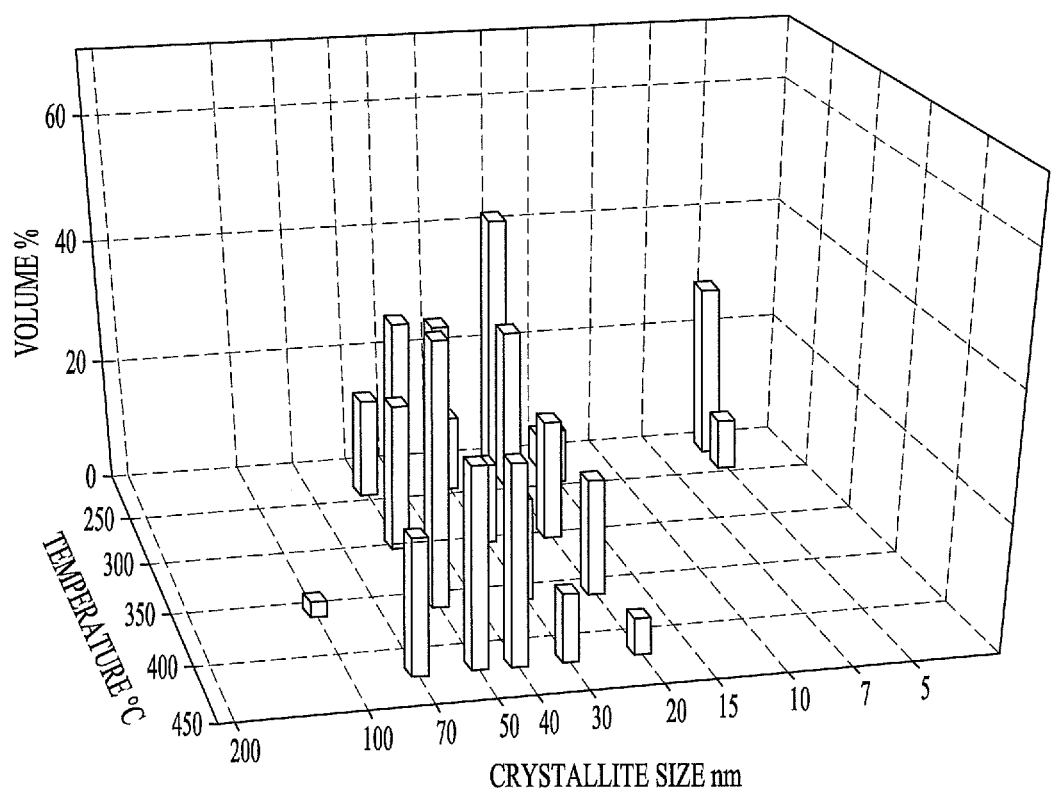
FIG. 9 shows TP-XRD data for a Ni metal particulate form obtained by hydrogen reduction of BNC sample #6 listed in Table 2. The graph was generated as described in Example 3 and for FIG. 4.
Figure 10:
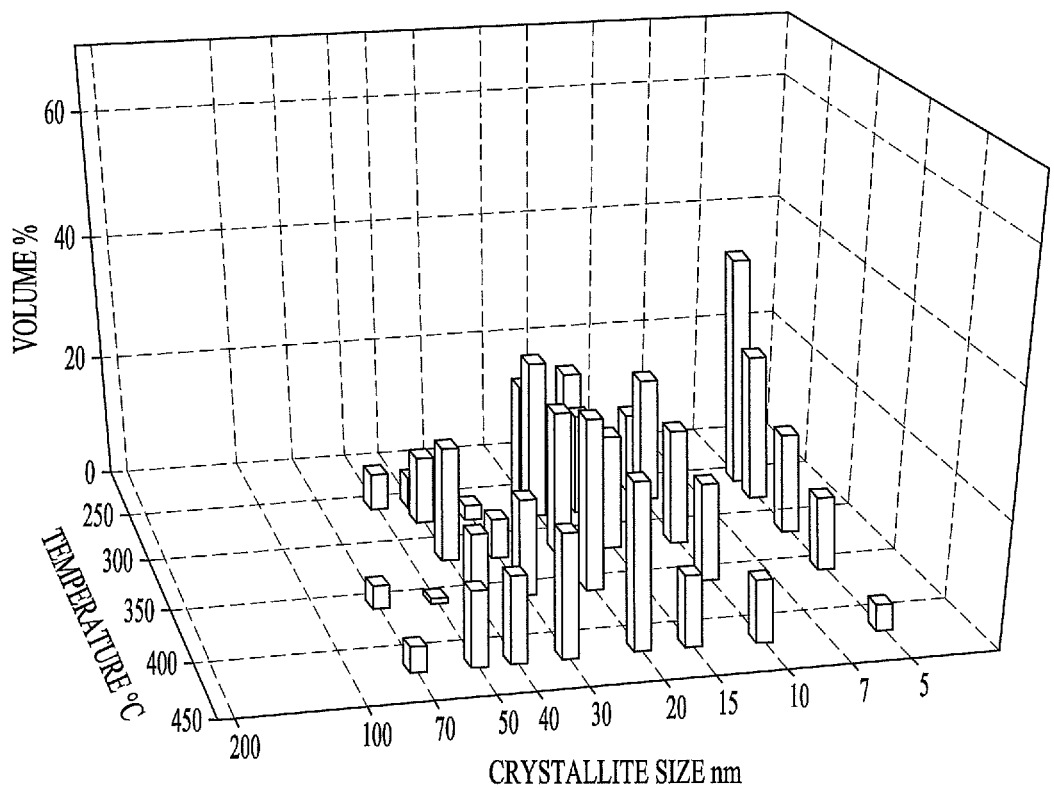
FIG. 10 shows TP-XRD data for a Ni metal particulate form obtained by hydrogen reduction of BNC sample #7 listed in Table 2. The graph was generated as described in Example 3 and for FIG. 4.
Figure 11:
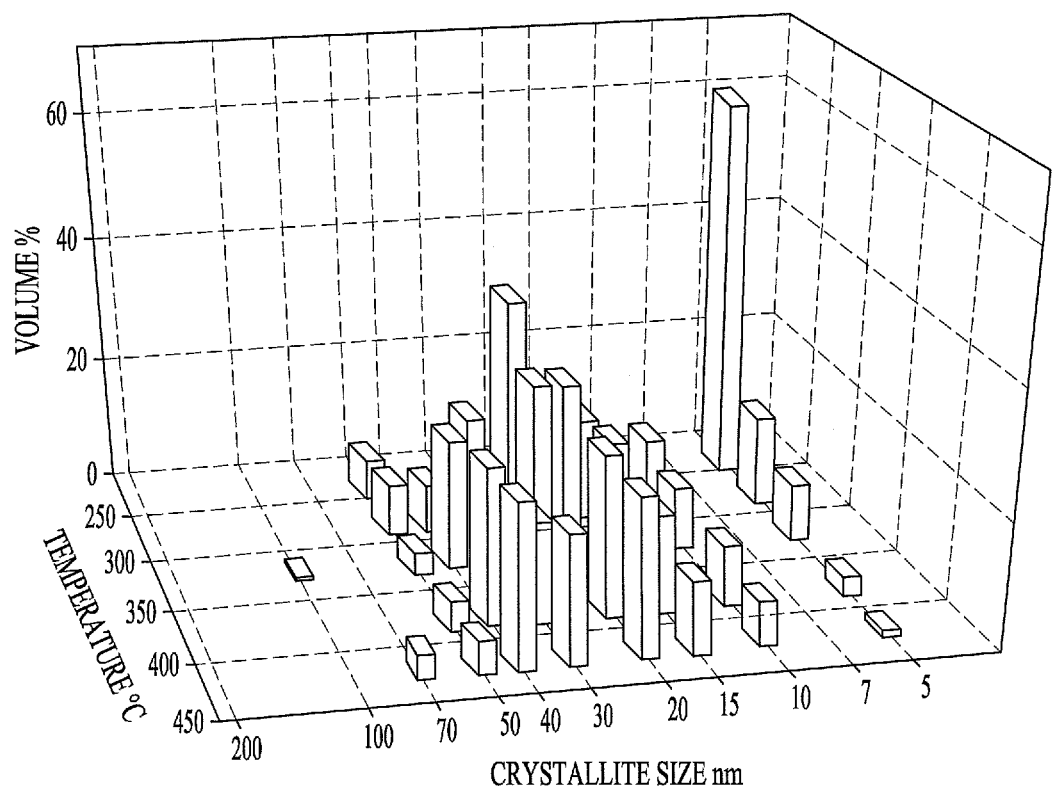
FIG. 11 shows TP-XRD data for a Ni metal particulate form obtained by hydrogen reduction of BNC sample #8 listed in Table 2. The graph was generated as described in Example 3 and for FIG. 4.

In contrast, FIG. 3A shows a pattern of hydrogen uptake versus increasing temperature for BNC samples #2, 5, 7, and 8 of Table 2, which yield active Ni samples upon reduction. The pattern of hydrogen uptake by calcined BNC samples #2, 5, 7, and 8 exhibit a single broadened hydrogen absorption maximum at around 400-450° C. This pattern is distinct from the pattern of hydrogen absorption exhibited for calcined BNC samples #3, 4, and 6 in FIG. 3A, where two peaks of absorption are observed. Thus, there is a correlation between the response of BNC to processing conditions and the activity of particulate form of Ni produced.

The outlier, BNC sample #1, is a minimally active sample that also is used to produce Ni1 with the properties shown in Table 4 below. As shown in FIG. 3A, a double maximum of hydrogen absorption is observed when BNC sample #1 is reduced, and such reduction occurs at a somewhat lower temperature than the temperature maxima observed for BNC samples #2, 5, 7, and 8. The two maxima observed for BNC #1 are also of approximately the same height.

Following the reduction step, analyses are performed on the resulting Ni metal-containing products, to examine crystallite size distributions for the various samples. For example, temperature programmed X-ray diffraction (TP-XRD) provides data showing Ni(111) based Ni crystallite size distribution for each of the eight BNC products.

FIGS. 4-11 show TP-XRD data for Ni metal particulate forms obtained by hydrogen reduction of BNC samples #1-8, respectively, as described above in Table 2. The temperature axis shows the progression of increasing temperature applied during the hydrogenation process, the crystallite size axis shows crystallite sizes, as determined by XRD in these data, and the volume-% axis indicates the distribution by volume of the various crystallite size classes in each bulk sample. Sample numbering corresponds to that shown in Table 2.

As illustrated, active samples #2, 5, 7, and 8 consistently show the presence of smaller crystallites throughout processing than do inactive samples #3, 4, and 6. Sample #1, considered to be marginally active at best, exhibits the larger crystallites, centered at about 30 nm, than the active nickel samples #2, 5, 7, and 8. Samples #2, 5, 7, and 8 all consistently exhibit a population of smaller crystallites, centered around about 20-25 nm, with a significant fraction of 10 nm or less. In contrast, inactive samples #3, 4, and 6 all are composed of significantly largely crystallites, averaging about 40-50 nm, with very little material present having a size of less than about 20 nm. It should be remembered that these data refer to crystallite size, not to the size of the actual Ni particles, which are of the order of microns to tens of microns in size. Each discrete Ni particle is composed of many crystallites. As used herein, "size" is an average diameter. A crystallite is a region of local crystalline order wherein neighboring crystallites do not extend that order, but have an internal order of their own.

Figure 12:
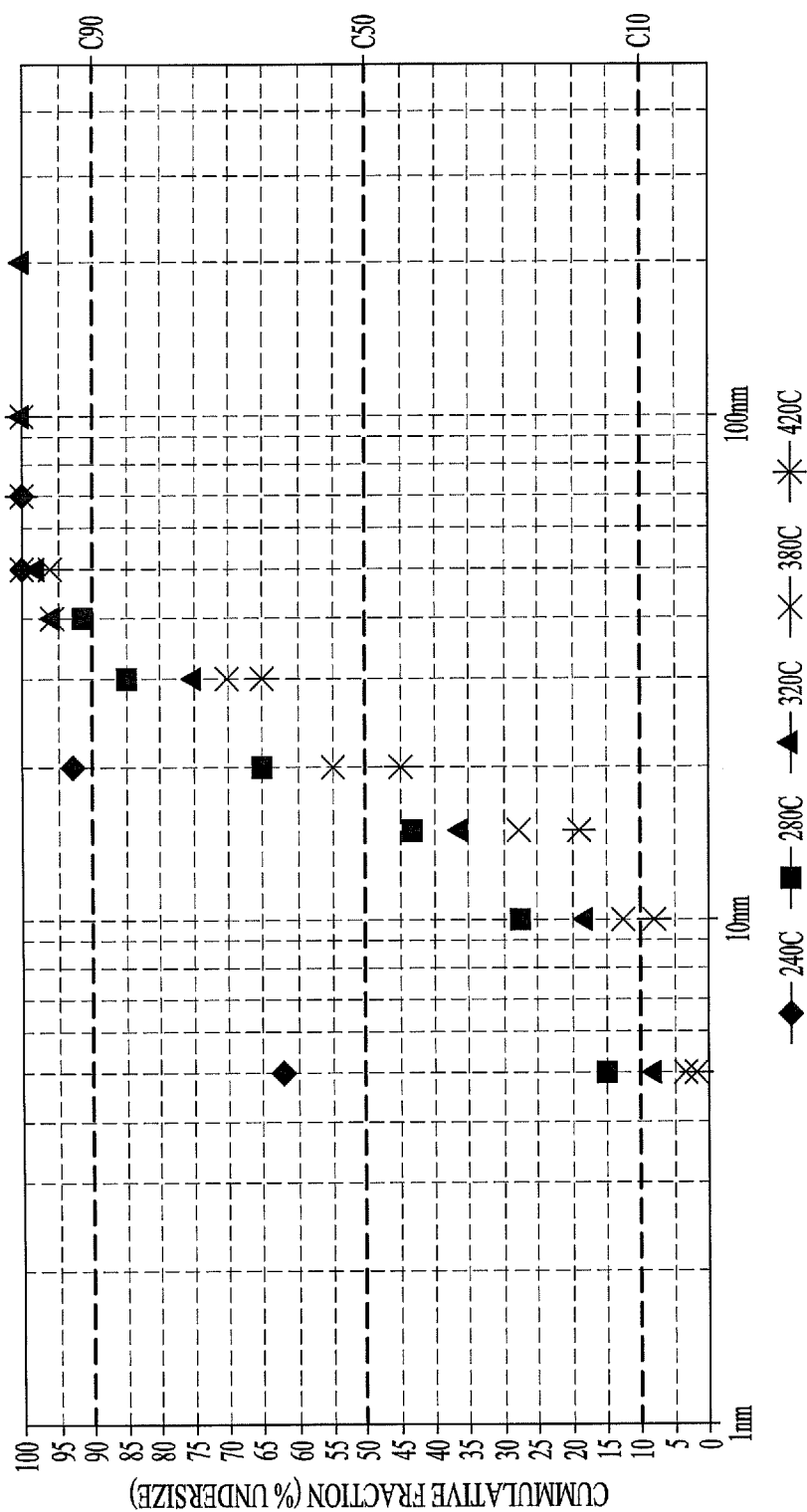
FIG. 12 is a graph illustrating the cumulative fraction (%) of undersized Ni crystallites as a function of crystallite size for determination of the crystallite size distribution (i.e., the width of the crystallite size distribution CSD) of nickel metal powder prepared from BNC sample #8 by reduction at the indicated temperatures.

FIG. 12 shows the crystallite size distribution (CSD) in a nickel sample prepared from BNC #8. CSD span is the width of the crystallite size distribution (CSD) where the crystallite size is obtained by TP-XRD and CSD is calculated as (C90-C10)/C50, where Cx is the size of the crystallite for which x % of the sample has a smaller size (e.g., the C90 size is the length (in nanometers) of the average diameter of Ni crystallites wherein 90% of the Ni crystallites in a bulk sample have a size less than the stated value).

Figure 13:
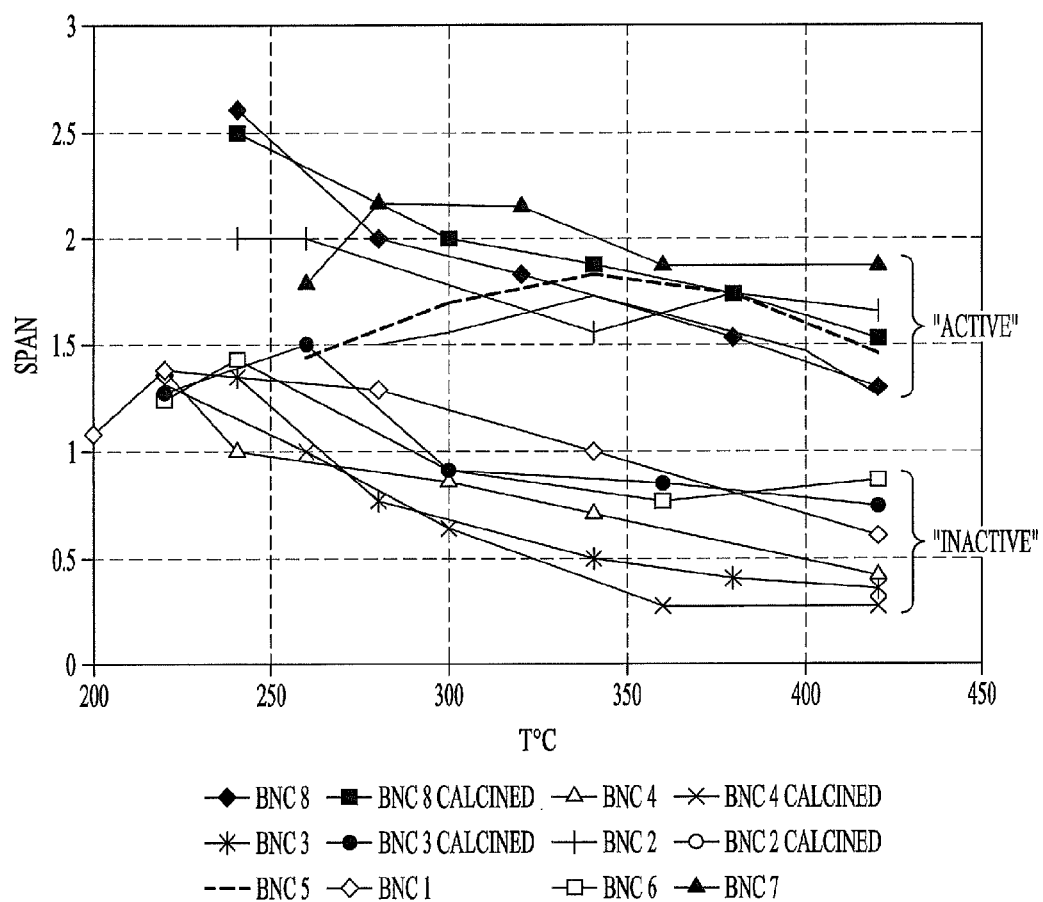
FIG. 13 shows that the crystallite size distribution (CSD) correlates with nickel activity. CSD data is shown for eight Ni powder samples prepared from the eight BNC samples listed in Table 2 after reduction at the indicated temperatures.

FIG. 13 shows crystallite size distribution (CSD) span data for the entire set of eight Ni powder samples prepared from the eight BNC samples of Table 2. As is apparent, these samples again fall into two groupings of "active" and "inactive", i.e., "nickel active" and "not nickel active," based on the numerical value of crystallite size distribution span. A CSD span of greater than 1, or greater than 1.5, is generally an indication of an active nickel. As the temperature of reduction increases, the CSD becomes narrower. Reduction temperatures of about 300-400° C. yield reduced nickel preparations with a good CSD span. In this study, it is found that BNC pre-calcination does not have a major impact on the CSD span.

Figure 14:
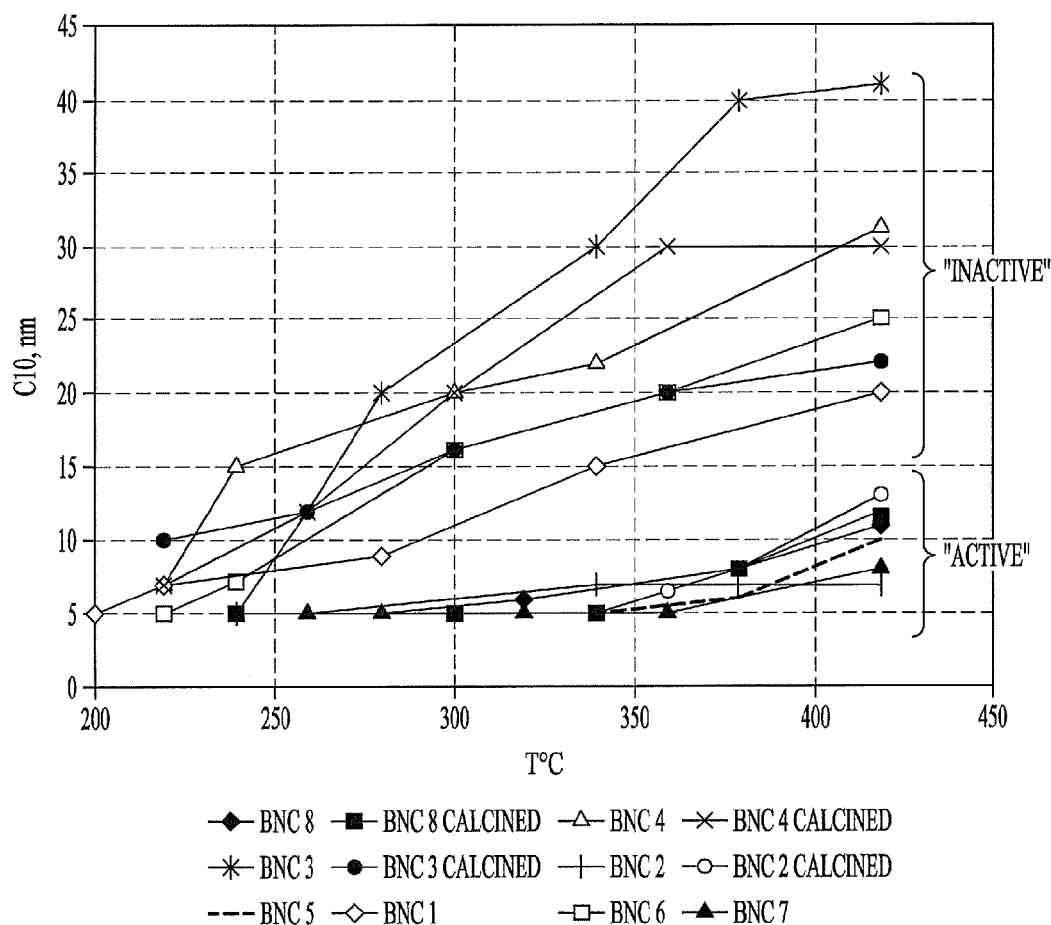
FIG. 14 graphically illustrates the relationship between nickel activity and the C10 value (the largest diameter in nanometers of the smallest 10% of crystallites) of various nickel samples generated from the eight BNC samples listed in Table 2 after reduction at the indicated temperatures.
Figure 15A:
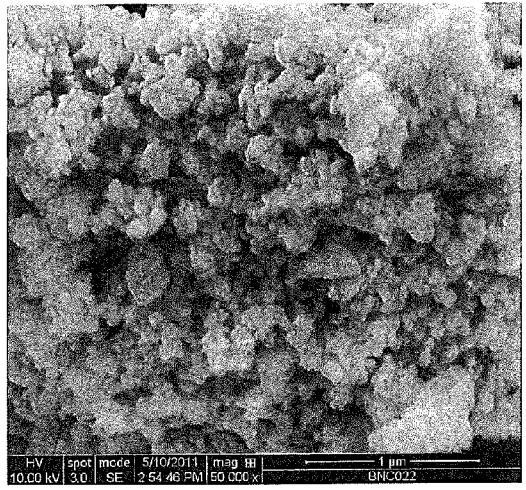
FIGS. 15A-15D are scanning electron photomicrographs of nickel particles.
Figure 15B:
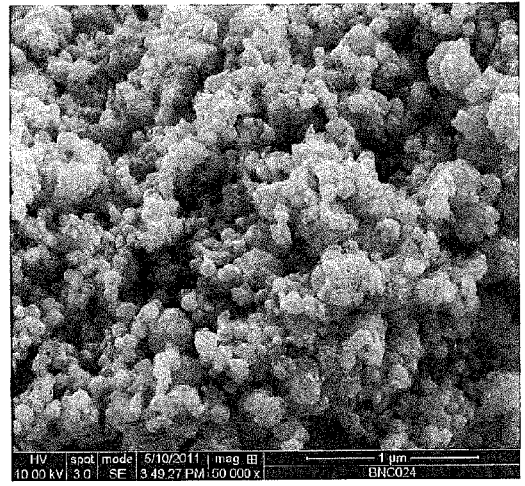
Figure 15C:
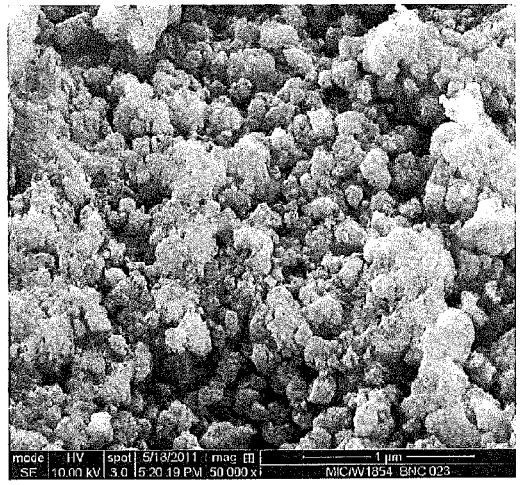
Figure 15D:
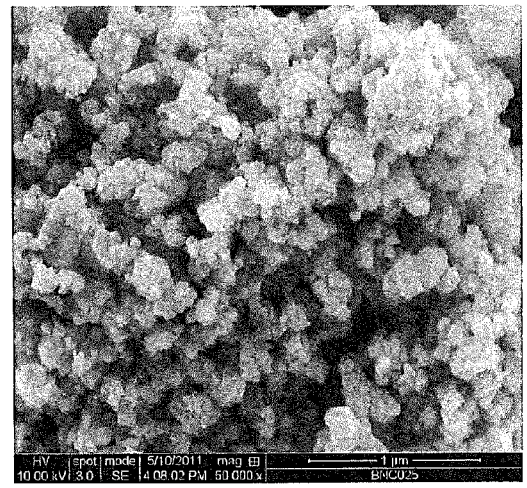

FIG. 14 shows the relationship between C10 (the dimension in microns at which 10% of the crystallites have a size less than the stated value) and the nickel activity of the sample. Note that these data refer to crystallite size, not to the size of the discrete particles of nickel. It is apparent again that the grouping of active Ni samples versus inactive samples shown in FIG. 14 is reflected in the grouping of C10 values. A Ni particulate form of the invention can have a C10 value of less than about 10 nm. Nickel samples having a C10 value of greater than about 10 nm may not be active nickel materials as the term is used herein. As discussed herein, the reduction temperature can affect the distribution of crystallite sizes. In general, a reduction temperature range of about 300-400° C. can yield nickel samples with desirable C10 values.

FIGS. 15A-D show SEM photographs of various samples of the nickel particulate form of the invention. No outstanding features are noted in the physical structure of the particles, indicating that the highly nickel active properties of the compositions are provided by molecular or macromolecular features of the substances. Not wishing to be bound by theory, the inventors herein believe that this feature relates to the availability of crystallite edges on the surface of a nickel particle, insomuch as edges are believed to be more reactive, e.g., with a ligand in solution, than are planar crystallite faces. A higher number of surface crystallites can correlate with a higher proportional abundance of crystallite edges available to approaching ligand molecules in solution.

Example 4

Further Analysis of BNC Samples and Ni Derived Therefrom

Selected BNC samples are further evaluated as discussed below.

General Procedure for Production of Ni Powders

Various BNC samples are tested as starting materials for nickel preparations. BNC samples, except the BNC used to generate the Ni1 in Table 4, are subjected to a calcination pretreatment followed by reduction at the indicated temperatures, with steam. Hydrogen gas flow to the reaction tube is set at 0.2 liters/minute (about one atmosphere) with any hydrogen off-gas from the reaction tube flowing through a bubbler. The temperature of the tube furnace is then increased at a rate of 10° C./minute to a final temperature of 400° C., and then held for one hour at 400° C., after which the reaction tube is allowed to cool under hydrogen flow. After the reaction tube temperature falls below 50° C. the flow to the reaction tube is switched to nitrogen gas to purge the hydrogen from the reaction tube. Valves on the reaction tube are then closed to prevent exposure of the resulting nickel-containing solid to air, and the entire reaction tube is transferred to a nitrogen-filled dry box where the nickel-containing solid is emptied into a bottle. This nickel-containing solid contains nickel metal as evidenced by the observation that it is attracted to a magnet. Exposing these nickel-containing solids to air can reduce rates for the reaction of the nickel with Ligand (V) in 3PN, and/or cause the nickel-containing solids to ignite.

Note that most of the Ni1-Ni10 nickel preparations in Table 4 are obtained from BNC samples from the same suppliers as those listed in Tables 2 and 3, however significant lot to lot, and batch to batch variation in the compositions of BNC from these suppliers is observed. Hence, although the BNC numbers in Table 4 correspond with the BNC numbers in Tables 2 and 3, and indicate that a BNC of the same number is obtained from the same supplier, different BNC batches obtained from the same supplier often have different compositions.

Analytical procedures similar to those described above are used to evaluate the nickel preparations. The D10 values for these nickel samples are determined by Particle Size Distribution analysis. Specific Surface Areas (SSA), i.e., surface area per unit mass, of the various samples is determined by two methods available in the art, BET SSA, and Laser Diffraction (LD) SSA, for each of the BNC reduction products. Laser Diffraction Specific Surface Area (LD SSA) and particle size distribution (PSD) are measured with a Mastersizer 2000 Particle Size Analyser from Malvern Instruments Ltd using the Hydro 2000MU accessory and water as the dispersant. Nitrogen adsorption BET Specific Surface Area (BET SSA) is measured using the Tristar 3000 Nitrogen Adsorption Instrument after degassing the samples under vacuum at 105° C. overnight. Multi-point BET measurements are made using a partial pressure range of 0.05-0.3 P/Po.

Samples of basic nickel carbonate are processed according to the procedures described above, and evaluated for C50, C10, CSD span (crystallite size distribution span=(C90-C10)/C50), LD and BET SSA values, and number of surface crystallites per gram at C50 and C10 dimensions, as well as nickel activity with respect to soluble catalyst formation as described above. The processed nickel samples are designated Ni1-Ni10.

Analytical Results and Discussion

Table 4 summarizes data for the prepared Ni samples Ni1-Ni10. As can be seen in Table 4, a strong correlation exists between BET SSA and activity. Sample Ni1 with a BET SSA of more than 1 m$^2$/gm but less than 10 m$^2$/gm, is comparable in activity to sample Ni5, assigned a control activity of 1, and the seven nickel samples Ni2, Ni3, Ni6, Ni7-Ni9 and N10), reactivity of the nickel with the bidentate phosphite ligand (V) ("nickel activity," see FIG. 17C).

Another factor that strongly correlates with Ni activity in reaction with Ligand (V) in 3PN is crystallite size, number or surface area. Each particle of nickel metal from the hydrogen-reduced BNC, or calcined and reduced BNC, is of the order of several microns or more. Each nickel particle can also be formed as an agglomeration of nickel metal crystallites, that is, domains of local crystalline order, of the sizes as described and discussed below.

Figure 16A:
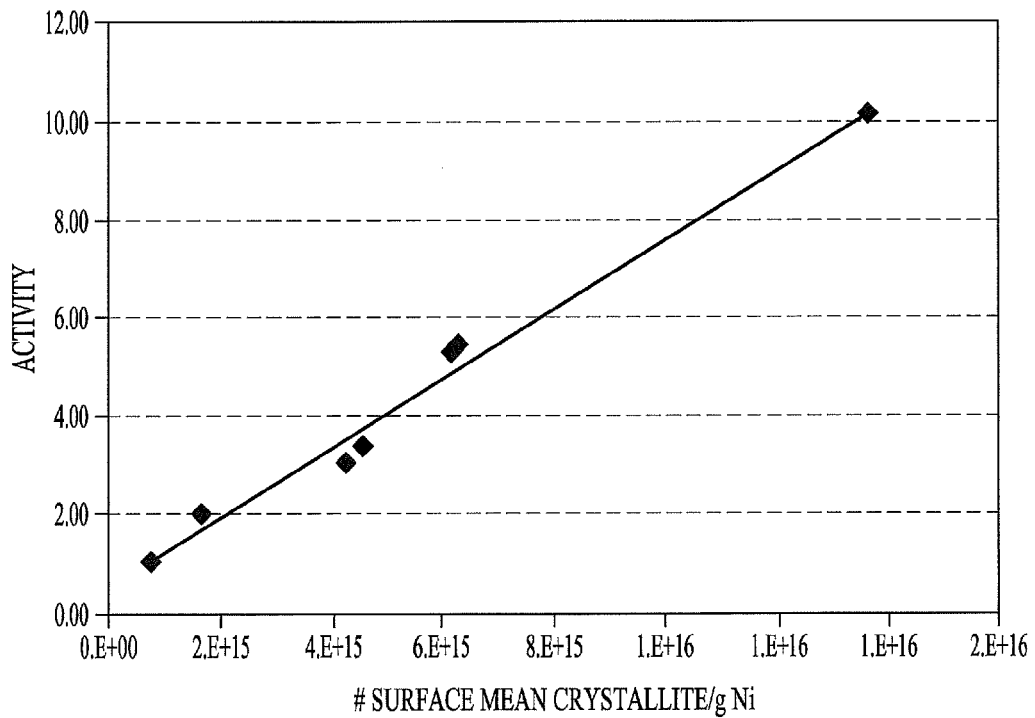
FIG. 16A graphically illustrates surface crystallite number per gm versus nickel activity for Ni1-Ni3, Ni5-Ni6, and Ni9-Ni10 samples (Table 4) based on the assumption that the shape of the crystallite is roughly spherical.

FIG. 16A shows a correlation for seven nickel active samples (Ni1-Ni3, Ni6, and Ni8-Ni10) between nickel activity and mean crystallite number per gram, based on the assumption that the shape of the crystallite is roughly spherical, using the following equation for calculation of the number of spherical crystallites:

$$\# \text{ surface spherical crystallite} = \text{BET}/4\pi(Cx/2)^2.$$

Figure 16B:
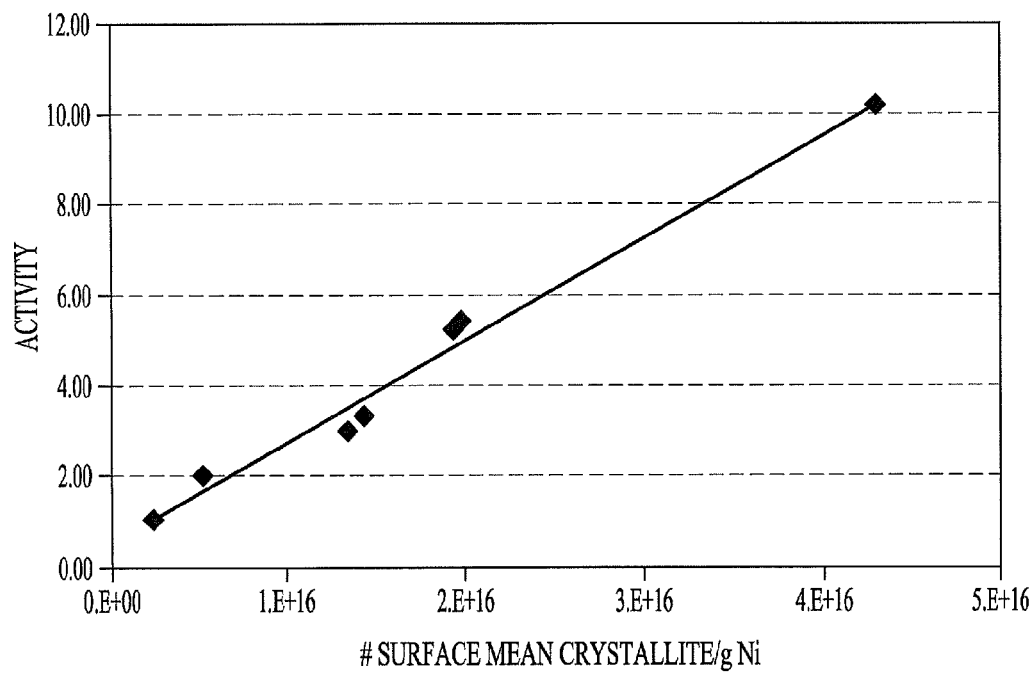
FIG. 16B graphically illustrates a correlation for the seven nickel active samples Ni1-Ni3, Ni5-Ni6, and Ni9-Ni10 between nickel activity and mean crystallite number per gram based on the assumption that the crystallite is of a substantially square cross section, i.e., is a cube or cuboidal shape. The properties of Ni1-Ni3, Ni5-Ni6, and Ni9-Ni10 are also described in Table 4.

FIG. 16B shows a correlation for the seven nickel active samples (Ni1-Ni3, Ni6, and Ni8-Ni10) between nickel activity and mean crystallite number per gram, based on the assumption that the crystallite is of a substantially square cross section, i.e., is a cube or cuboidal. The following equation is used for calculation of the number of cuboidal crystallites:

$$\# \text{ surface cuboidal crystallites} = \text{BET}/(Cx)^2.$$

As nickel is known to generally assume a face-centered cubic close-packing array in the elemental state, as assumption that the crystallites are cuboidal may be more accurate. FIG. 16A thus presents results according to a standard Scherrer analysis as described above, and FIG. 16B recalculates the results based on a crystallite shape believed to be that taken by the cubic-packing Ni atoms.

TABLE 4

Nickel Samples with Crystallite Sizes, SSA Values, Number of Surface Crystallites, and Ratio BET SSA/C50

| Nickel From BNC | C50 nm | C10 nm | crystallite span | C50 SA, m$^2$ | C10 SA, m$^2$ | LD SSA m$^2$/g | BET SSA m$^2$/g | number of surface cuboidal C50/gm Ni | number of surface cuboidal C10/gm Ni | BET SSA/ C50 ×10$^9$ m/gm | activity |
|---|---|---|---|---|---|---|---|---|---|---|---|
| Ni1 (BNC #1) 400 C., one step | 28 | 19 | 0.6 | 7.84E−16 | 3.61E−16 | 0.123 | 1.90 | 2.42E+15 | 5.26E+15 | 0.07 | 1.09 |
| Ni2 (BNC #1) 300 C., one step | 19 | 11 | 1.14 | 3.61E−16 | 1.21E−16 | 0.123 | 1.90 | 5.26E+15 | 1.57E+16 | 0.10 | 2.00 |
| Ni3 (BNC #2) proc run 13 | 26.5 | 9 | 2.02 | 7.02E−16 | 8.10E−17 | 1.320 | 30.20 | 4.30E+16 | 3.73E+17 | 1.14 | 10.20 |
| Ni4 (BNC #3) 400 C., one step | 44.5 | 40.5 | 0.37 | 1.98E−15 | 1.64E−15 | NA | NA | NA | NA | NA | 0.06 |
| Ni5 (BNC #3) 300 C., two steps | 30 | 16 | 0.9 | 9.00E−16 | 2.56E−16 | NA | NA | NA | NA | NA | 1 |
| Ni6 (BNC #7) chem proc run 14 | 31 | 12 | 2.06 | 9.61E−16 | 1.44E−16 | 0.607 | 12.90 | 1.34E+16 | 8.96E+16 | 0.42 | 3.00 |
| Ni7 | NA | NA | NA | NA | NA | 0.469 | 15 | NA | NA | NA | 6.29 |
| Ni8 (BNC #8) proc run 12 | 35.5 | 12.5 | 1.75 | 1.26E−15 | 1.56E−16 | 0.832 | 18.10 | 1.44E+16 | 1.16E+17 | 0.51 | 3.35 |
| Ni9 (BNC #8) proc run 16 | 32.5 | 12 | 2.06 | 1.06E−15 | 1.44E−16 | 0.808 | 20.50 | 1.94E+16 | 1.42E+17 | 0.63 | 5.24 |
| Ni10 (BNC #8) 400 C. two steps | 29 | 10 | 1.63 | 8.41E−16 | 1.00E−16 | 0.707 | 16.59 | 1.97E+16 | 1.66E+17 | 0.57 | 5.40 | prepared from BNC samples as described above and selected based on activity, show a close correlation of BET SSA with A calculation of BET SSA/C50 (Table 4) is provided for comparison with nickel activity. It can be seen that a ratio of BET SSA/C50 of at least about $0.07 \times 10^9$ or at least about $0.1 \times 10^9$ m/gm provides a minimal nickel activity of 1. Higher values for the ratio correlate with greater nickel activities, with the greatest nickel activities correlating with a BET SSA/C50 ratio in the $0.5-1.0 \times 10^9$ m/gm range.

Figure 17A:
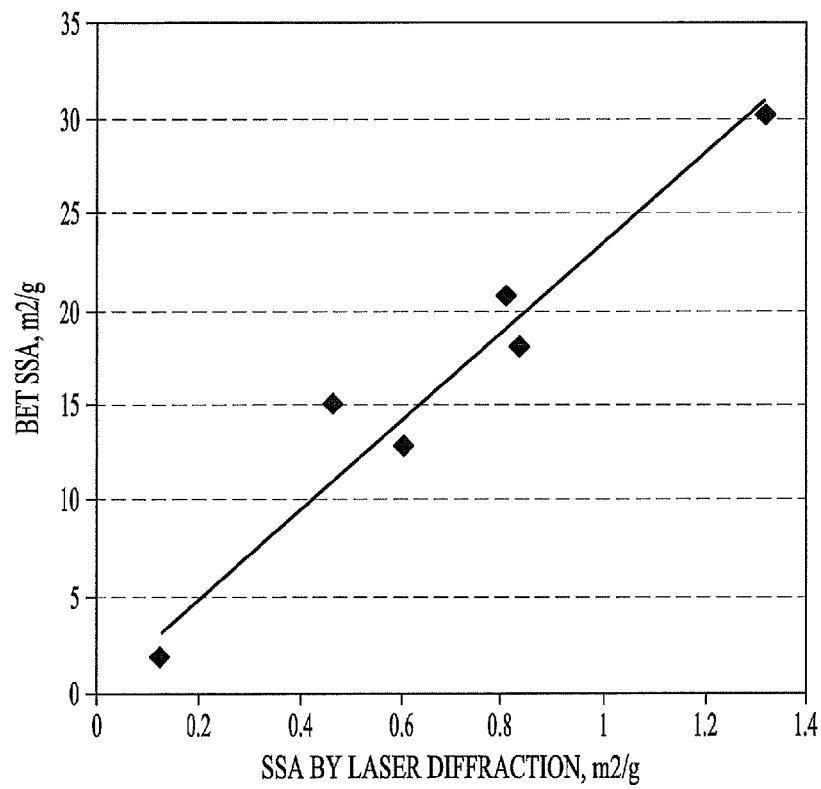
FIGS. 17A-17C graphically illustrate correlations between nickel particle/crystallite surface area and the activity or of nickel preparations to form nickel-ligand complexes.
Figure 17B:
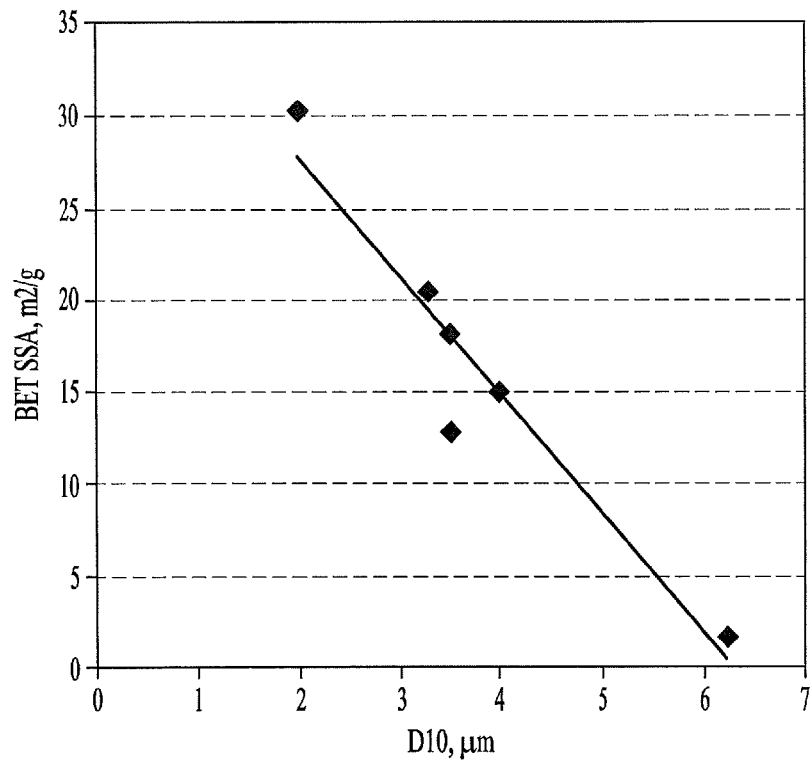
Figure 17C:
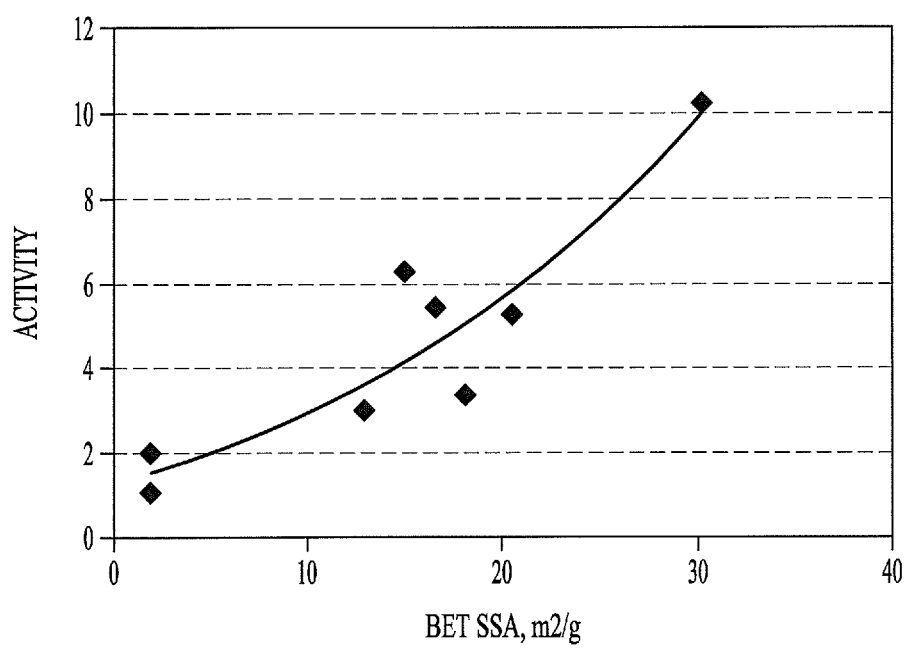

FIG. 17A is a graph showing the correlation of BET SSA and LD SSA, while FIG. 17B is a graph of BET SSA versus D10 for nickel samples Ni1, Ni3, Ni6-Ni8 and Ni9. FIG. 17C illustrates a close correlation of BET SSA with the activity of the nickel to efficiently complex with the bidentate phosphite ligand (V).

Figure 18:
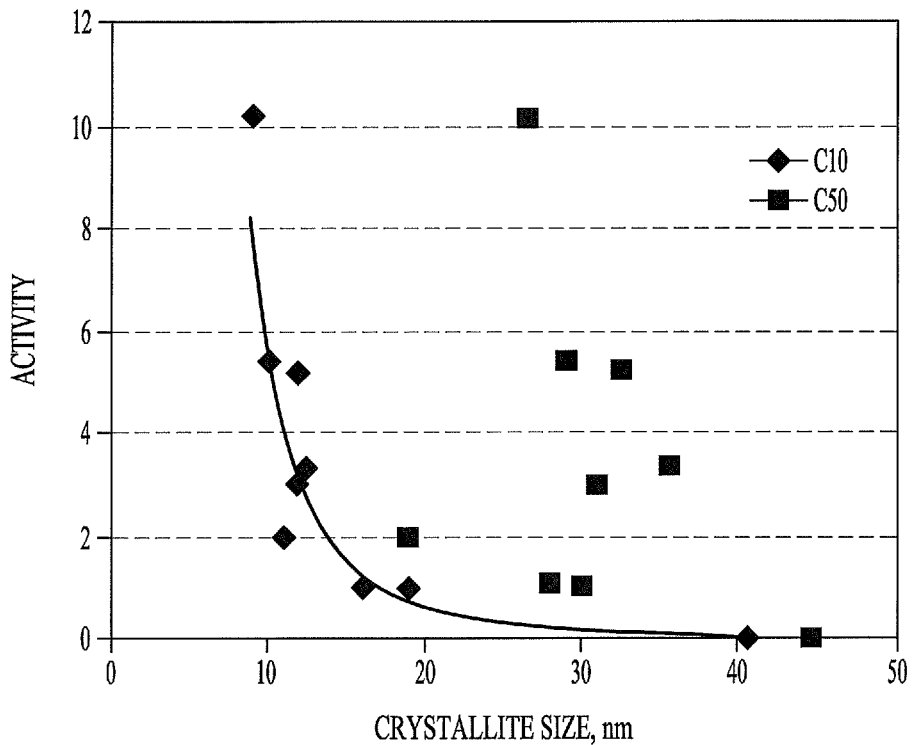
FIG. 18 graphically illustrates nickel activity versus C10 and C50 values for samples Ni1-Ni6 and Ni8-Ni10 that have the properties listed in Table 4.

FIG. 18 graphically illustrates mean crystallite size (MCS=C50) versus nickel activity as defined herein as well as C10 versus nickel activity as defined herein. For these calculations, it is assumed that the geometry of crystallites is of a substantially square cross section, i.e. is a cube or cuboidal shape. It is also noted that BET SSA linearly correlates with Laser Diffraction SSA for Ni, see FIG. 17A.

Figure 19:
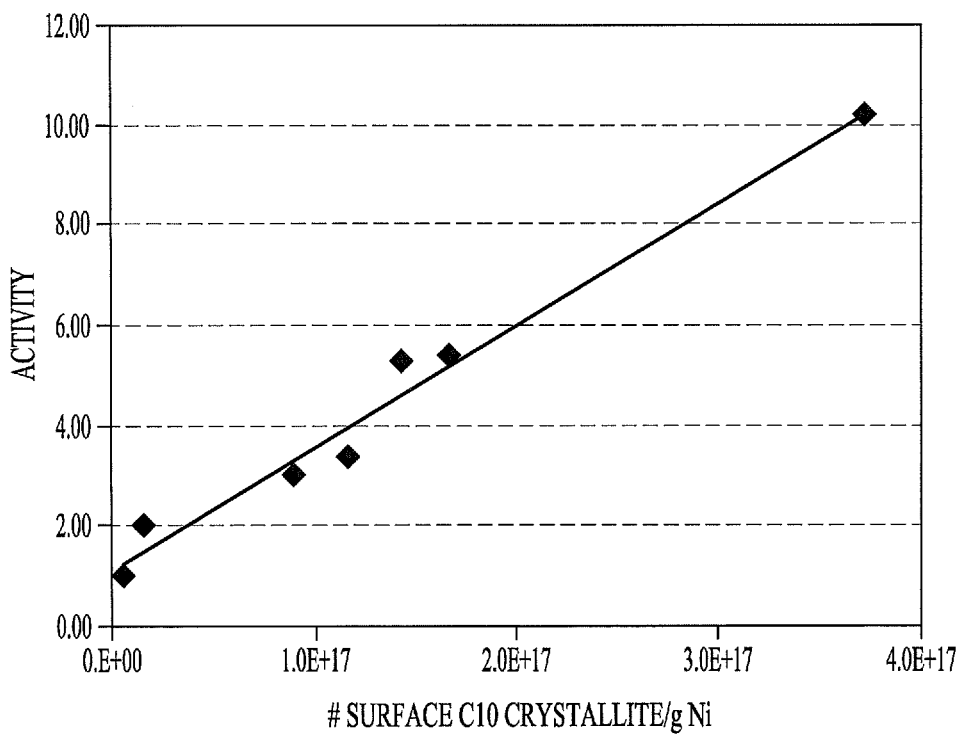
FIG. 19 graphically illustrates a correlation between the number of surface crystallites of a size not greater than the C10 value for a nickel sample and the nickel activity of that sample.

As FIG. 18 illustrates, a mean crystallite size (C50) of less than about 30 nm and a C10 value of less than about 20 nm generally correlate with a nickel activity of 1 or greater. For higher nickel activity values to be achieved, small mean crystallite size and especially small C10 values are highly correlated. As can be seen in Table 4, C10 values approaching about 10 nm provide specimens with greater nickel activity. FIG. 19 shows a correlation between the number of surface crystallites of a size not greater than the C10 value for a nickel sample and the nickel activity of that sample.

The correlation of raw C50 values and nickel activity appears to be less strong. Ni1 and Ni8, control samples, having C50 values of 44.5 and 30 nm respectively, and C10 values of 40.5 and 16 nm, respectively, show the lowest nickel activities. Sample Ni1, having a C50 of 28 nm and a C10 of 19 nm has a slightly higher nickel activity. At nickel activities of greater magnitude, the C10 values grow steadily smaller, but the C50 values are relatively constant. FIG. 17C shows a correlation of BET SSA with nickel activity for the same nickel samples. A correlation is observed between increasing BET SSA and nickel activity for the seven samples Ni1-Ni3, Ni6, Ni8, Ni9, and Ni10.

These data indicate that nickel activity is increased by lower C10 values, greater BET SSA values, larger numbers of surface crystallites per gram, and larger numbers of particles having a size of D10 or less.

In Table 4, a ratio is calculated for BET SSA divided by C50, for each of the seven active samples, Ni1-Ni3, Ni5-Ni6, and Ni9-Ni10. This ratio can be viewed as normalizing the SSA for crystallite size within the range studied. It is apparent that a strong correlation exists between the SSA/C50 ratio and nickel activity, such that a nickel metal particulate composition with a BET SSA/C50 ratio of not less than about $0.07 \times 10^9$ m/gm, or at least $0.1 \times 10^9$ m/gm, or at least about $0.4 \times 10^9$ m/gm, is an indicator of a nickel particulate form with good activity. Nickel particulate forms with very good activity can have BET SSA/C50 ratios of up to about $1.0 \times 10^9$ m/gm. Samples having a higher BET SSA/C50 value, should they be prepared, are expected to have yet higher nickel activity as the term is used herein, i.e., with respect to formation of soluble zero-valent nickel catalyst complexes with phosphorus-containing ligands in an organic milieu.

Figure 20:
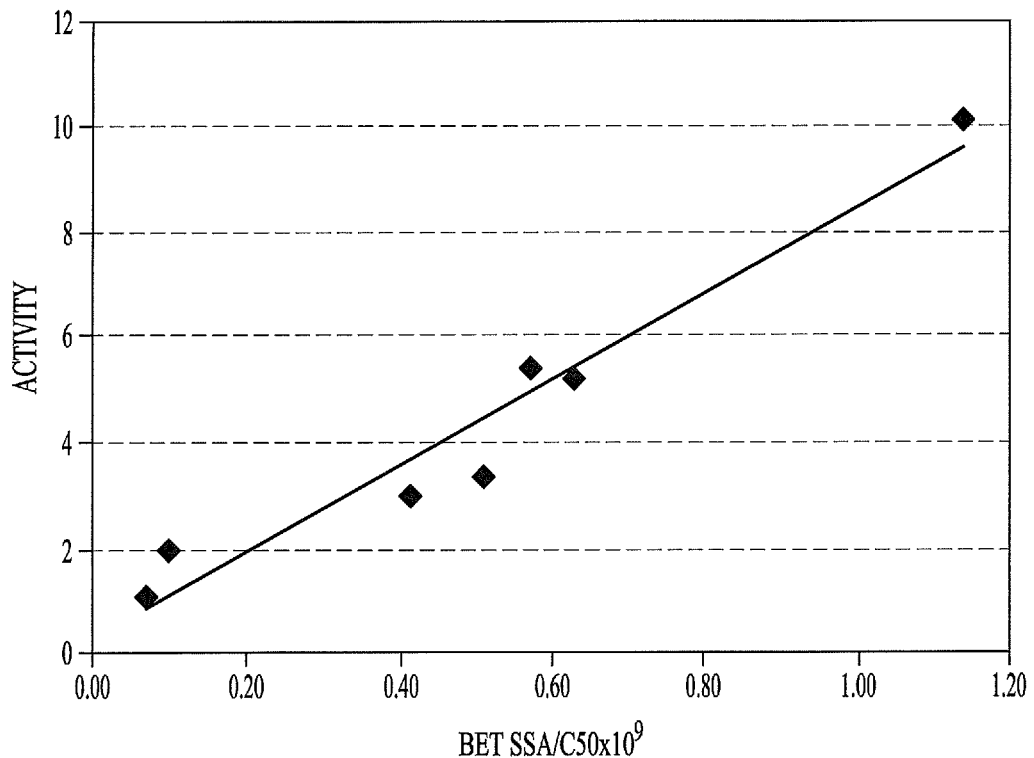
FIG. 20 graphically illustrates a correlation between nickel activity and BET SSA/C50 using the data presented in Table 4 for each of the nickel samples having activity of at least 1 as defined herein.

FIG. 20 graphically illustrates the strong correlation between nickel activity and BET SSA/C50 using the data shown in Table 4 for each of the nickel samples having activity of at least 1 as defined herein.

Also, SSA values as determined by BET and LD methods are found to have a substantially constant ratio of about 23.46. Accordingly a ratio of LD SSA/C50 of greater than about $(0.1/23.46) \times 10^9$ m/gm=$0.0043 \times 10^9$=$4.3 \times 10^6$ can be used to be an indication of a nickel composition of the invention, having a nickel activity suitable for efficient catalyst preparation with bidentate nickel-phosphite zero-valent complexes.

Example 5

Unsuitable Nickel Precursors for Making Active Nickel

Nickel and nickel oxide samples as received from various commercial sources are analyzed to determine their sulfur content, and their activity for complex formation with Ligand (V) as described in Example 1.

After such analysis, 10 grams of these commercial sources of nickel metal and nickel oxide are loaded into a fluidized bed reactor, heated to 400° C. under a nitrogen flow for 1 h and reduced at 400° C. with 20% $H_2$ in $N_2$ for 2 h. The resulting reduced nickel powder is then transferred into a $N_2$ purged glovebox and analyzed again for complex formation with Ligand (V), mean crystallite size (MSD) and BET surface area using the assays described in Example 1.

The results are shown in Tables 5 and 6.

TABLE 5

Commercial NiO (sample C) and Ni powders (samples A, B and D)

| Supplier Code | Composition* | ppm S in Ni[a] | BET SSA[b] of Ni, m²/g | Ni MCS[c], nm | Activity Reduced Ni | Activity Unreduced Ni[a] |
|---|---|---|---|---|---|---|
| A (Ni) | 99% Ni | 1 | 0.33[a] | 102 | 0.01 | 0 |
| B (Ni) | 98-99% Ni | 1 | 1.63[a] | — | 0.51 | 0.01 |
| C (NiO) | | 110 | 10.2 | 35.6 | 0.48 | 0.48 |
| D (Ni/NiO) | 30-90% Ni; remainder NiO | 200 | 53.60[a] | — | 0.24 | 0.03 |

*Composition is from Material Safety Data Sheets from the supplier;
[a]Data is for the nickel materials as received from the supplier;
[b]BET SSA is a measure of nickel particle surface area, described in more detail above;
[c]MCS is the mean crystallite size (C50), described in more detail above.

TABLE 6

Commercial Basic Nickel Carbonate, $Ni(CO_3)_x(OH)_y(H_2O)_z$

| BNC Supplier[a] | BNC Composition[b] | | | | | Reduced Ni Properties | | | |
| | % CO₃ | % Ni | % H₂O | ppm S | S/Ni Ratio ×10⁻⁴ | ppm S in Ni | BET SSA, m²/g | Ni MCS[c] nm | activity |
|---|---|---|---|---|---|---|---|---|---|
| BNC #1 | 19.50 | 42.08 | 30.27 | 212 | 9.22 | — | 2.50 | 28 | 1.00 |
| BNC #2 | 21.89 | 43.83 | 21.29 | 400 | 16.7 | 400 | 11.00 | 25 | 0.22 |

TABLE 6-continued

Commercial Basic Nickel Carbonate, $Ni(CO_3)_x(OH)_y(H_2O)_z$

| | BNC Composition[b] | | | | Reduced Ni Properties | | | |
|---|---|---|---|---|---|---|---|---|
| BNC Supplier[a] | % $CO_3$ | % Ni | % $H_2O$ | ppm S | S/Ni Ratio ×$10^{-4}$ | ppm S in Ni | BET SSA, $m^2/g$ | Ni MCS[c] nm | activity |
| BNC #2 | 20.78 | 41.64 | 25.23 | 300 | 13.2 | 200 | 12.70 | 15 | 1.98 |
| BNC #2 | 22.70 | 50.01 | 11.18 | 400 | 14.6 | 500 | 11.40 | 19 | 0.91 |
| BNC #2 | 26.06 | 40.17 | 25.27 | 300 | 13.7 | 700 | 11.80 | 31 | 0.23 |
| BNC #2 | 33.75 | 49.1 | 10.90 | 400 | 14.9 | 700 | 10.00 | 82 | 0.39 |
| BNC #3 | 32.00 | 45.33 | 19.49 | 5 | 0.20 | — | — | 34 | 0.07 |
| BNC #4 | 24.51 | 46.16 | 21.91 | 7 | 0.28 | — | 0.80 | 32 | 0.05 |
| BNC #6 | 28.00 | 45.53 | 21.45 | 10 | 0.40 | — | — | 41 | 0.50 |
| BNC# 11 | 26.28 | 47.26 | 13.97 | nd[d] | — | — | — | — | 0.50 |

[a]The BNC Supplier numbers correspond to the same BNC suppliers listed in Tables 2-4; BNC #11 is a new supplier of BNC;
[b]data is for the samples as received from the supplier;
[c]MCS is the mean crystallite size (C50), described in more detail above;
[d]nd: not detected.

Note that BNC sample #1 is MetChem BNC. After reduction at 400° C., this MetChem BNC yields a nickel metal preparation with a relative activity of 1.00. Nickel metal generated from MetChem BNC has an initial rate of dissolution of 317 ppm/hr at 60° C. and 980 ppm/hr at 80° C. (4% Nickel loading).

Example 6

Suitable Precursors and Methods for Making Active Nickel

A. Making Active Nickel from Various Commercial Nickel Starting Materials Containing Sulfur Impurities The properties of various commercially available nickel starting materials such as basic nickel carbonate and nickel formate are examined to evaluate which properties correlate with good nickel-ligand complex formation.

a) Basic Nickel Carbonate (BNC): $Ni(CO_3)_x(OH)_y(H_2O)_z(SO_4)_q$.

Basic Nickel Carbonate (BNC; $Ni(CO_3)_x(OH)_y(H_2O)_z(SO_4)_q$) BNC from various commercial sources is analyzed by loading ten grams of the BNC samples into a fluidized bed reactor, heating the reactor to 400° C. under a nitrogen flow for 1 h and reducing the samples at 400° C. with 20% $H_2$ in $N_2$ for 2 h. The resulting reduced nickel powder is then transferred into a $N_2$ purged glovebox and evaluated using the nickel-ligand complex formation and other assays described in Examples 1-4. The results are shown in Table 7a.

Table 7a illustrates that the ability of nickel metal to form nickel-phosphorus ligand complexes relates to the content of sulfur in the nickel (or BNC used to make the nickel metal).

b) Nickel Formate, Dihydrate (NF): $Ni(HCO_2)_2 \cdot 2H_2O$

The composition of nickel formate, dihydrate ($Ni(HCO_2)_2 \cdot 2H_2O$, referred to as 'NF') from two commercial sources is analyzed by loading ten grams of these NF samples into a fluidized bed reactor and heating the samples to 400° C. under a nitrogen flow for 2 h in the absence of hydrogen. The resulting nickel powder is then transferred into a $N_2$ purged glovebox and evaluated using the nickel-ligand complex formation and other assays described in Examples 1-4. Table 7b provides the results.

TABLE 7b

Composition of NF sources for making Active Nickel-Ligand Catalysts

| | NF Composition[a] | | | | |
|---|---|---|---|---|---|
| NF Supplier | % Ni | % $H_2O$ | ppm S | S/Ni Ratio × $10^{-4}$ | activity |
| NF #1 | 32.12 | 21.88 | 575 | 32.8 | 1.97 |
| NF #2 | 31.33 | 20.15 | 1300 | 75.9 | 6.86 |

[a]Data is for the samples as received from the supplier.

The results presented in Table 7b indicate that it is also possible to directly prepare active nickel from thermal decomposition of commercial nickel formate dihydrate containing a sulfur impurity (as sulfate ion) without reduction of TABLE 7a Properties of BNC Sources for Making Active Nickel-Ligand Catalysts

| | BNC Composition[a] | | | | | Ni composition | | reduced Ni properties | | |
|---|---|---|---|---|---|---|---|---|---|---|
| BNC Supplier | % $CO_3$ | % Ni | % $H_2O$ | ppm S | S/Ni Ratio ×$10^{-4}$ | ppm S | % $Ni_3S_2$ by XRD | BET SSA, $m^2/g$ | Ni MCS, nm | Activity |
| BNC #8 | 22.39 | 47.74 | 17.18 | 2505 | 96 | 5500 | 0.90 | 4.70 | 50 | 7.96 |
| BNC #8 | 24.57 | 46.25 | 17.90 | 3162 | 125 | 5300 | 0.80 | 4.30 | 38 | 8.66 |
| BNC #8 | 23.44 | 47.3 | 17.52 | 3797 | 147 | 8200 | 2.30 | 4.60 | 48 | 10.11 |
| BNC #8 | 22.19 | 47.15 | 18.24 | 4674 | 181 | 8600 | 3.10 | 3.45 | 51 | 6.31 |
| BNC #7 | 16.75 | 40.97 | 27.31 | 18760 | 838 | 26800 | 13.50 | 12.90 | 31 | 9.00 |
| BNC #2 | 16.66 | 44.49 | 18.15 | 23930 | 985 | 33700 | 12.50 | 9.20 | 42 | 16.34 |

[a]Data is for the samples as received from the supplier.

the nickel metal (e.g., without hydrogen reduction). For a method of removing sufate ion impurities, see N. Minkova, M. Krusteva, V. Valiseva, D. Trendafelov, Communications of The Department of Chemistry, p. 222-228, Volume 13, Number 12, 1980.

This method of using nickel formate contrasts with the use of commercial BNC or NiO powders that do require a reduction step with hydrogen to obtain a nickel material suitable for ligand catalyst preparation.

c) Method for Making a Ni Inactive by Removing Sulfur from a BNC Containing a Sulphate Impurity Removal of sulfur (sulfate ions) from a BNC that was initially suitable for making active nickel yields a BNC that is unsuitable for preparing active nickel.

Sulfur removal is accomplished by washing the BNC containing traces of sulfate ions with 2.5% sodium carbonate solution (10 parts carbonate solution/1 part BNC) at 90° C. for 2 h. After cooling the mixture to ambient temperature, the resulting desulfurized BNC is filtered onto paper using vacuum suction and dried for 20 h in air at 80° C. in an oven. The content of sulfur, $CO_3$, nickel and water in the sample is then analyzed using methods described in Example 1.

Ten grams of the "desulfurized" BNC sample are loaded into a fluidized bed reactor, heated to 400° C. under a nitrogen flow for 1 h and reduced at 400° C. with 20% $H_2$ in $N_2$ for 2 h. The resulting reduced nickel powder is then transferred into a $N_2$ purged glovebox and evaluated using the nickel-ligand complex formation and other assays described in Examples 1-4.

Table 7c shows the composition of BNC #8, before and after sulfur removal. As shown, the activity of the Ni significantly decreases when the sulfur content in BNC is reduced.

TABLE 7c

Composition of BNC#8 and its corresponding Ni activity before and after S removal

| BNC Supplier | BNC Composition[a] | | | | | Ni composition | | reduced Ni properties | | |
|---|---|---|---|---|---|---|---|---|---|---|
| | % $CO_3$ | % Ni | % $H_2O$ | ppm S | S/Ni Ratio ×$10^{-4}$ | ppm S | % $Ni_3S_2$ by XRD | BET SSA, $m^2/g$ | Ni MCS, nm | activity |
| BNC #8 as received | 24.57 | 46.25 | 17.90 | 3162 | 125 | 5300 | 0.80 | 4.30 | 38 | 8.66 |
| BNC #8 after S removal | 20.17 | 53.90 | 10.10 | 698 | 23.7 | 1100 | 0.36 | 2.20 | 43 | 0.03 |

[a]Data is for the sample as received from the supplier.

B. Method for Making Active Nickel with a Nickel Sulfate Solution—Doping of a Commercial Basic Nickel Carbonate (BNC)

Commercial BNC is treated with various aqueous 1M salt solutions of $NiSO_4$ by mixing the BNC with the salt at a ratio of 1:5 by weight and stirring the mixture for 15 min. at room temperature in air. The metal powder is then filtered onto paper using vacuum suction and dried for 20 h in air at 80° C. in an oven. The content of sulfur, $CO_3$, nickel and water in the samples is then analyzed using methods described in Example 1.

Ten gram samples of the dried powder are gently ground with a mortar and pestle to disperse the solids, the samples are loaded into a fluidized bed reactor, then heated to 400° C. under nitrogen flow for 1 h and reduced at 400° C. with 20% $H_2$ in $N_2$ gas for 2 h. The resulting reduced nickel powder is then transferred into a $N_2$ purged glovebox and evaluated for nickel-ligand catalyst preparation activity as well as composition, BET SSA, and MCS using the assays described in Examples 1-4.

The results shown in the following Table 8 indicate that treatment of BNC with nickel sulfate improves the formation of nickel that actively complexes with phosphorus-containing ligands.

TABLE 8

Treatment of BNC Samples with 1M Nickel Sulfate Solution

| BNC sample | BNC Composition | | | | | Reduced Ni Composition | | Reduced Ni properties | | |
|---|---|---|---|---|---|---|---|---|---|---|
| | % $CO_3$ | % Ni | % $H_2O$ | ppm S | S/Ni Ratio ×$10^{-4}$ | ppm S | % $Ni_3S_2$ by XRD | BET SSA, $m^2/g$ | Ni MCS, nm | Activity |
| BNC #2 + 1M $NiSO_4$ | 15.97 | 47.83 | 14.79 | 34000 | 1301 | 53000 | 18.00 | 10.9 | 42 | 17.03 |

TABLE 8-continued

Treatment of BNC Samples with 1M Nickel Sulfate Solution

| BNC sample | BNC Composition | | | | | Reduced Ni Composition | | Reduced Ni properties | | |
|---|---|---|---|---|---|---|---|---|---|---|
| | % $CO_3$ | % Ni | % $H_2O$ | ppm S | S/Ni Ratio ×10$^{-4}$ | ppm S | % $Ni_3S_2$ by XRD | BET SSA, $m^2/g$ | Ni MCS, nm | Activity |
| BNC #2 + 1M $NiSO_4$ | 18.30 | 46.08 | 15.87 | 32000 | 1271 | 66000 | 21.50 | 12.9 | 92 | 19.53 |
| BNC #11 + 1M $NiSO_4$ | 19.32 | 48.4 | 14.02 | 9880 | 373.6 | 33000 | 8.60 | 16.6 | 31 | 10.42 |
| BNC #4 + 1M $NiSO_4$ | 20.66 | 46.6 | 18.49 | 12775 | 501.8 | 31200 | 13.10 | 2.6 | 66.5 | 6.36 |

Additional experiments are performed to optimize sulfate incorporation into BNC samples. Commercially available basic nickel carbonate (BNC #11) is added to a series of 0.01-1 M nickel sulfate solutions. The BNC to $NiSO_4$ ratio is about 5. The BNC solids are slurried in the nickel sulfate solution and stirred for about 15-30 minutes. A further example is carried out in which water is used instead of the nickel sulfate solution. The resulting solids are then filtered from the solution and dried under vacuum at 80° C. overnight. The solids are then calcined at 400° C. in a muffle furnace under air to produce nickel oxide.

The nickel oxides are then reduced with 30% hydrogen under flow reactor conditions as previously described to give reduced nickel. The nickel is transferred to a nickel catalyst preparation setup without any exposure to air. The activity of nickel dissolution is determined by measuring nickel dissolved vs. time in the nickel-ligand complex formation assay described in Example 1. As indicated in the following table, as the nickel sulfate concentration is raised from 0.01 M to 0.05 M, the nickel activity jumps from 1.4 to greater than 8.

TABLE 9

Treatment of BNC with Nickel Sulfate

| BNC Sample | % S (wt %) in Ni | Ni Activity |
|---|---|---|
| BNC #11 | 0.0% | 0.5 |
| BNC #11 water washed | 0.12% | 0.5 |
| BNC #11 + 0.01M $NiSO_4$ | 0.30% | 1.4 |
| BNC #11 + 0.05M $NiSO_4$ | 0.88% | 8.2 |
| BNC #11 + 0.10M $NiSO_4$ | 1.37% | 7.5 |
| BNC #11 + 1.00M $NiSO_4$ | 2.60% | 8.7 |

C. Active Nickel Made by Nickel Sulfate Doping of BNC Remains Active Over Time and Through Several Cycles of Ligand Formation Commercially available BNC (BNC #11) is doped with sulfur by using nickel sulfate. The BNC—nickel sulfate mixture is calcined and reduced at 400° C. with 10-30% hydrogen in nitrogen. The resulting nickel is tested for its dissolution and complex formation using the nickel-catalyst preparation assay described in Example 1. After the first dissolution of nickel with ligand, the dissolved nickel-ligand catalyst is decanted leaving the undissolved/unreacted nickel behind. The undissolved nickel is again tested for its activity for to dissolve and complex with ligand. This is repeated in total of 4 times to check for the variability of activity and determine if there is a reduction in the activity after one or more dissolutions. The amount of sulfur in starting material is 2.6% by weight on nickel basis.

TABLE 10

The Presence of Sulfur Improves Nickel Complex Formation

| BNC #11 Sample | Nickel at start of dissolution (g) | Activity |
|---|---|---|
| BNC #11 | 3.20 | 0.5 |
| BNC #11 + 2.6% S | 3.22 | 8.71 |
| BNC #11 + 2.6% S - First complex formation | 3.01 | 8.55 |
| BNC #11 + 2.6% S - Second refresh | 2.81 | 7.00 |
| BNC #11 + 2.6% S - Third complex formation | 2.60 | 8.57 |
| BNC #11 + 2.6% S - Fourth complex formation | 2.40 | 7.10 |

D. Method for Making Active Nickel from $NiSO_4$ Solution by Doping of Commercial NiO (Sample C) or NiO-Coated (Passivated) Nickel (Sample D)

Commercially available NiO or NiO-coated nickel samples that are previously assessed to be inactive (see Example 5) are mixed with 1M $NiSO_4$ aqueous solution at a ratio of 1:5 by weight and stirred for 15 min at room temperature in air. The powder is then filtered onto paper using vacuum suction and dried for 20 h in air at 80° C. in an oven. The resulting powder (~10 g) is gently ground with a mortar and pestle to disperse the solids. The ground powder is then loaded into a fluidized bed reactor, heated to 400° C. under nitrogen flow and directly reduced with 20% $H_2$ in $N_2$ for 2 h at 400° C. The resulting reduced nickel powder is then transferred into a $N_2$ purged glovebox and evaluated for nickel-ligand catalyst preparation activity as described in Example 1.

TABLE 11

Low Activity Nickel Sources are Improved by $NiSO_4$ Treatment

| NiO sample | Ni composition | | Reduced Ni properties | | |
|---|---|---|---|---|---|
| | ppm S | % $Ni_3S_2$ by XRD | BET SSA, $m^2/g$ | Ni MCS, nm | activity |
| C + 1M $NiSO_4$ | 7155 | 2.90 | 11.20 | 31 | 6.74 |
| D + 1M $NiSO_4$ | 25000 | 7.4 | 24.70 | 39.0 | 11.32 |

E. Method for Making Active Nickel by Elemental Sulfur Doping of Basic Nickel Carbonate and its Subsequent Nickel Oxide Commercially available BNC #1 is tested to evaluate whether sulfur (e.g., rather than sulfate) can activate the nickel therein to improve complex formation with phosphorus-containing ligands.

Three aliquots of BNC #1 are tested (#1A, #1B and #1C). About 35 g of BNC #1A is mixed with 0.16 g of elemental sulfur (1 wt % on nickel basis). The mixture is calcined at 400° C. in a muffle furnace under air to nickel oxide. The nickel oxide/sulfur powder is reduced at 400° C. with 30% hydrogen in nitrogen gas mixture for 2 hours. The reduced nickel is evaluated for activity under standard catalyst preparation conditions described in Example 1.

Another BNC sample (BNC #1B) is first calcined to form nickel oxide. The nickel oxide is then doped with 1% elemental sulfur (on nickel basis) and further reduced at 400° C. with 30% hydrogen in nitrogen gas mixture for 2 hours.

Finally, a third BNC #1C sample is calcined and reduced at 400° C. using the aforementioned conditions without any sulfur addition. The activity of all reduced nickel samples is measured under the nickel-ligand complex formation assay described in Example 1.

The activity of MetChem nickel with sulfur is 6× higher than nickel not doped with elemental sulfur.

TABLE 12

Use of Elemental Sulfur to Activate Nickel

| BNC #1 Sample | % S in final nickel (wt %) | Activity |
|---|---|---|
| BNC #1A + 1% elemental S | Tbd | 5.8 |
| BNC #1B → nickel oxide, then + 1% elemental S | 0.95% | 6.1 |
| BNC #1C (no sulfur added) | 0.12% | 1.3 |

F. Method for Activating Nickel by Doping a Commercial Source of Nickel Oxide with Elemental Sulfur: Comparative Operative and Inoperative Examples of Product Nickel Twenty gram samples of various commercial nickel oxides are mixed with about 0.16 g of elemental sulfur (1% by weight on nickel basis) and reduced at 400° C. under flow of 10-30% $H_2/N_2$ for few hours until the material is completely reduced. The reduced nickel is then dissolved the nickel-ligand complex formation assay mixture described in Example 1, and the activity of dissolution is determined.

A 20 g sample of nickel oxide is separately reduced with 10-30% $H_2/N_2$ at 400° C. for few hours to obtain reduced nickel untreated with sulfur.

The activity of the nickel products is determined using the catalyst preparation assay.

TABLE 13

Treatment of Nickel Oxide with Sulfur Improves Reduced Nickel Activity

| | | Surface area (m²/g) | | |
|---|---|---|---|---|
| Nickel Oxide Sample | % S (wt %) | Nickel oxide | Nickel | Activity |
| NiO sample E | 0.12% | 4.8 | tbd | 1.31 |
| NiO sample E + 1% S | 0.95% | 4.8 | 2.8 | 6.07 |
| NiO sample F | 0.17% | 52.7 | tbd | 1.27 |
| NiO sample F + 1% S | tbd | 52.7 | 5.14 | 8.04 |
| NiO sample F + 1.6% S | 1.62% | 52.7 | 5.14 | 9.01 |
| NiO sample G | 0.05% | 0.77 | tbd | 0.10 |
| NiO sample G + 1% S | 0.5% | 0.77 | 1.47 | 2.96 |
| NiO sample H | 0.05% | 81.2 | tbd | 0.54 |
| NiO sample H + 1% S | 1.04% | 81.2 | 1.4 | 4.63 |
| NiO sample I | 0.22% | 7.6 | tbd | 3.35 |
| NiO sample I + 1% S | 0.74% | 7.6 | 4.0 | 6.96 |
| NiO sample J | 0.16% | 99.2 | tbd | 2.57 |
| NiO sample J + 1% S | 1.05% | 99.2 | 3.4 | 5.23 |

G. Relating Activity of Nickel with the BET Surface Area of Reduced Nickel

Example 6F shows that addition of approximately 1% elemental sulfur to nickel oxide samples followed by reduction resulted in improved nickel activity for these samples in the catalyst-preparation dissolution assay compared to its baseline activity without any sulfur addition. However, a plot of all the data in Table 13 relating to BET surface area vs. activity did not provide a meaningful correlation for these nickel oxide samples, possibly because the samples had different sulfur contents and reduction conditions.

Figure 21:
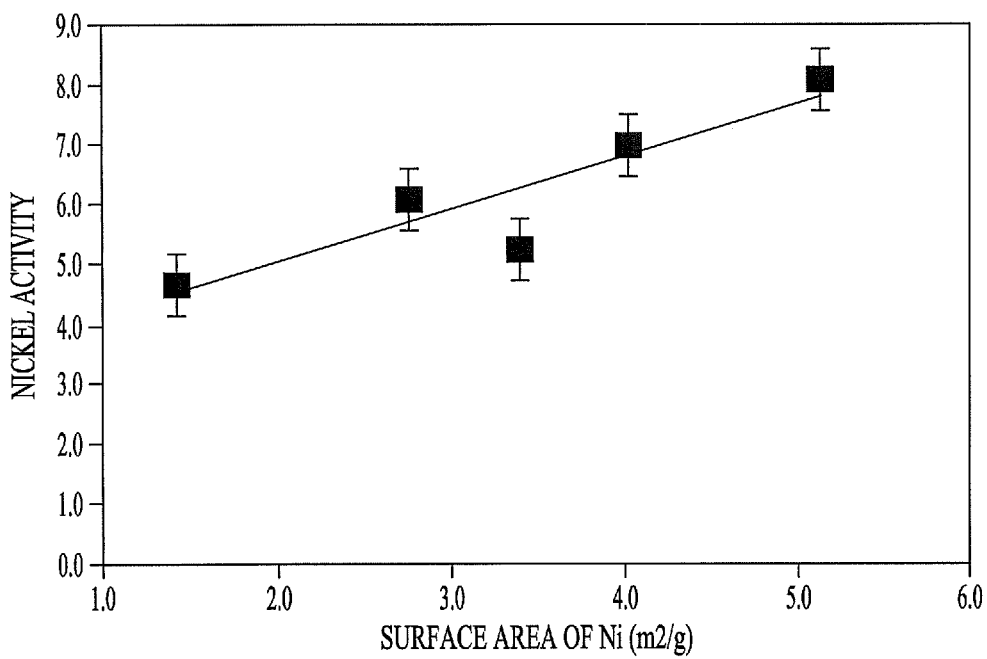
FIG. 21 graphically illustrates the a correlation between nickel activity and BET SSA for nickel samples with equivalent sulfur content (1%) that had been reduced under the same conditions (in hydrogen at 400° C.).

However, if the reduction conditions and the sulfur concentration of the nickel are held approximately constant there is a meaningful correlation between the activity of the nickel and the nickel BET surface area. Thus, nickel oxide samples with similar sulfur content (in this instance ~1%) are reduced under similar conditions (in this case reduction was carried out at 400° C. and 2 hours). FIG. 21 shows that the BET surface area of these nickel samples is correlated with nickel complex formation activity. The extent of sulfur loading somewhat depends on the initial surface area of the nickel oxide. If the sulfur loading is not constant, the activity will not correlate very well with the BET surface area because sulfur content plays a dominant role in promoting the activity of nickel while BET SSA plays a secondary role.

H. Reduction Temperature Affects Activity of Elemental Sulfur Doped Nickel

Nickel oxide sample F is doped with ~1% elemental sulfur (on nickel basis) and reduced at temperatures varying from 200 to 500° C. The reduction time is 4 hours. The amount of hydrogen used is approximately 20 times the stoichiometric amount required for complete reduction of nickel oxides. Even though the amount of sulfur should be same in all these cases, the activity observed is a function of the temperature used. The activity went through an optimum value with highest observed for reduction temperature of 300° C. The table below shows the effect of temperature.

TABLE 14

Reduction Temperature Affects the Nickel Metal Activity

| Sample | Temperature (° C.) | % S (wt % of nickel) | Activity |
|---|---|---|---|
| NiO Sample F (no S added) | 400 | 0.17% | 1.3 |
| NiO Sample F + 1% S | 200 | 0.808 | 5.5 |
| NiO Sample F + 1% S | 250 | 0.954 | 8.7 |
| NiO Sample F + 1% S | 300 | 1.039 | 11.3 |
| NiO Sample F + 1% S | 350 | 0.968 | 9.0 |
| NiO Sample F + 1% S | 400 | 1.035 | 7.0 |
| NiO Sample F + 1% S | 450 | 0.941 | 5.5 |
| NiO Sample F + 1% S | 500 | 1.005 | 3.2 |

I. Method for Making Nickel with Addition of Solid Nickel Sulfate, or Nickel Sulfide to a Commercial Basic Nickel Carbonate (BNC)

A commercial BNC sample (BNC #2) is mixed with $NiSO_4.6H_2O$ or $Ni_3S_2$ using a mortar and pestle in air. The resulting powder (~10 g) is then loaded into a fluidized bed reactor, heated to 400° C. under nitrogen flow for 1 h (no hold-up time for NiO) and reduced at 400° C. with 20% $H_2$ in $N_2$ for 2 h. The resulting reduced nickel powder is then transferred into a $N_2$ purged glovebox and evaluated in the nickel-ligand complex formation assay described in Example 1.

TABLE 15

Active Nickel can be made by adding sulfur
in various forms (sulfate, sulfide) to BNC in solid form

| sample | BNC/NiO Composition | | | Ni properties | |
|---|---|---|---|---|---|
| | % CO$_3$ | % Ni | % H$_2$O | ppm S | activity |
| BNC #2 + 8.7% NiSO$_4$•6H$_2$O | 27.68 | 46.77 | 13.52 | 15413 | 15.76 |
| BNC #2 + 3.5% Ni$_3$S$_2$ | 32.25 | 48.01 | 12.19 | 18755 | 20.91 |

J. Method for Making Active Nickel by Sulfur Doping of Reduced Nickel Without Thermal Treatment About 20 g of nickel oxide (sample E) is reduced at 400° C. with 30% H$_2$/N$_2$ for a couple of hours until the oxide is fully reduced to nickel. About 2.5 wt % (on nickel basis) of elemental sulfur is added to the reduced nickel. The product is then tested for activity by dissolution in the nickel catalyst preparation assay. A similar nickel oxide is reduced and tested for the activity of the metal in the absence of sulfur.

A second source of nickel oxide is mixed with sulfur and evaluated in the nickel-ligand complex formation assay described in Example 1.

TABLE 16

Sulfur Activation of Reduced Nickel

| Sample | % S (wt %) | Surface area | Activity |
|---|---|---|---|
| NiO (sample E) | 0.12% | tbd | 1.3 |
| NiO (sample E) + 3.7% S | tbd | tbd | 1.9 |
| NiO (sample F) => Ni | 0.17% | 52.7 | 1.3 |
| NiO (sample F) => Ni + 2.5% S | tbd | 52.7 | 4.3 |

In another experiment, about 3.2 g of nickel is prepared by reduction of NiO (sample F) at 400° C. The reduced nickel metal powder is tested in the catalyst preparation, assay where about 150-500 ppm of elemental sulfur (on total weight basis of the catalyst preparation assay) is directly added to the catalyst preparation assay mixture using the procedures described in Example 1.

TABLE 17

Direct Addition of Sulfur to Nickel Catalyst Preparation Mixture

| Sample | S amount (ppm) in cat-prep | Activity |
|---|---|---|
| NiO (sample F) => Ni | 0 | 0.5 |
| NiO (sample F) => Ni + 0.4% S | 150 | 2.8 |
| NiO (sample F) => Ni + 0.6% S | 250 | 3.1 |
| NiO (sample F) => Ni + 1.2% S | 500 | 4.0 |

In another experiment, BNC #11 and NiO (sample F) are reduced at 400° C. About 3.2 g of reduced nickel is tested in the nickel catalyst preparation assay. About 10-150 ppm of equivalent sulfur in the form of nickel sulfate is added to the catalyst preparation assay mixture described in Example 1.

TABLE 18

Addition of Nickel Sulfate to Nickel Catalyst Preparation Mixture

| Sample | Equivalent S (ppm) from NiSO$_4$ | Activity |
|---|---|---|
| NiO (sample F) => Ni | 0 | 0.5 |
| NiO (sample F) => Ni + 10 ppm S | 10 | 0.7 |
| NiO (sample F) => Ni + 50 ppm S | 50 | 1.3 |
| NiO (sample F) => Ni + 150 ppm S | 150 | 1.5 |
| BNC #11 → Ni | 0 | 0.5 |
| BNC #11 → Ni + 150 ppm S | 150 | 2.0 |

In another experiment, elemental sulfur is added directly to a nickel catalyst preparation mixture containing nickel metal. The mixture is then heated to 60° C. and the assay procedure is conducted as described in Example 1.

TABLE 19

Elemental Sulfur Addition to Nickel-Ligand catalyst preparation reaction mixture

| sample | activity |
|---|---|
| Ni D + 12% S$_8$ based on Ni | 1.1 |
| Reuse Ni D+ 12% S$_8$ based on Ni | 3 |

Note that in Table 5, Ni D had an activity of only about 0.24 when no sulfur source was added.

K. Method for Improving Nickel Activity by Pre-Mixing and Heating Elemental Sulfur S$_8$ with Unreduced NiO-Coated Ni Prior to the Nickel-Ligand Catalyst Prep Elemental sulfur is mixed with a commercial NiO-coated Ni or a passivated Ni in a flask either in pentenenitrile solution or neat as a solid mixture. The mixture is agitated while heated at 110° C. for 24 h. The resulting powder/slurry is then evaluated in the nickel-ligand complex formation assay described in Example 1.

TABLE 20

Elemental Sulfur Addition to Nickel-Ligand catalyst preparation reaction mixture

| sample | activity |
|---|---|
| Unreduced Ni B + 11% S$_8$ based on Ni in 3PN | 0.92 |
| Unreduced Ni B + 11% S$_8$ based on Ni (solid mix) | 1.73 |
| BNC #12 derived passivated Ni + 12% S$_8$ based on Ni (solid mix) | 0.84 |

Note also that, as shown in Table 5 above, unreduced nickel sample B had an activity of 0.01.

L. Making Active Nickel by S Doping of Carbonyl Based Nickel

Carbonyl based nickel sample is treated with sulfur either by directly doping them with nickel sulfate and thermal treatment or by forced sulfidation with elemental sulfur.

In the former case, sample nickel A is treated with 1 M NiSO$_4$ for about 15-30 minutes with stirring. The solution is filtered to retain nickel loaded with nickel sulfate. These solids are then dried under vacuum at 80° C. and then further calcined and reduced at 400° C. In reduced form, the nickel A sample has a BET surface area of 0.49 m²/g.

After the first dissolution/complexation, four additional dissolution/complexations are performed successively using undissolved nickel in the same nickel catalyst preparation mixture.

TABLE 21

NiSO₄ Treatment Improves Nickel Complex Formation

| Nickel Sample A | % S (wt %) | Activity |
|---|---|---|
| Ni A | 0.006 | 0.15 |
| Ni A + 1M. NiSO₄ | 0.354 | 0.78 |
| Ni A + 1M. NiSO₄ First complex formation | 0.354 | 2.23 |
| Ni A + 1M. NiSO₄ Second complex formation | 0.354 | 1.04 |
| Ni A + 1M. NiSO₄ Third complex formation | 0.354 | 0.95 |
| Ni A + 1M. NiSO₄ Fourth complex formation | 0.354 | 1.02 |

Samples of commercial nickel K and L (as received) are stirred in an Adiponitrile (ADN) solution containing a selected amount of sulfur for 24-48 hours at 110-120° C. The activity of these nickel samples is shown in Table 21.

TABLE 22

Sulfur Treatment Improves Nickel Catalyst Activity

| Ni Sample | Activity |
|---|---|
| K | 0 |
| K + 1.25% S/ADN | 0.14 |
| K + 31.3% S/ADN | 0.58 |
| L | 0 |
| L + 1.25% S/ADN | 0.12 |
| L + 31.3% S/ADN | 0.78 |

The following statements are intended to describe some aspects of the invention.

STATEMENTS DESCRIBING FEATURES OF THE INVENTION

1. A nickel particulate form comprising nickel crystallites, wherein the nickel particulate form has at least two properties selected from the group consisting of:
   the nickel particulate form has a BET Specific Surface Area of at least about 1 m²/gm;
   at least 10% of the nickel crystallites have a size (C10) that is less than about 20 nm;
   the nickel crystallites have an average crystallite size of no greater than about 100 nm;
   the nickel crystallite size distribution span is greater than about 1.0;
   the nickel particulate form has a BET Specific Surface Area/C50 ratio of not less than 0.07×10⁹ m/gm;
   the nickel particulate form on average has at least about 10¹⁵ surface crystallites per gram of nickel;
   at least 10% of the particles of the form have a size (D10) of no greater than about 6 µm;
   the nickel particulate form has a Laser Diffraction Specific Surface Area of at least about 0.4 m²/gm;
   the nickel particulate form has a BET Specific Surface Area to D10 ratio of about 0.3×10⁶ m/gm to about 10.0×10⁶ m/gm;
   on average there are at least about 10¹⁶ surface crystallites per gram nickel that are smaller than or equal to size C10; and
   the nickel particulate form complexes with Ligand (V) within about 2 hours when about 4 to 5 wt % of the nickel particulate form is mixed with 3-pentenenitrile containing approximately 5.25 wt % Ligand (V) and approximately 6300 ppm ZnCl₂; wherein Ligand (V) has the following formula:

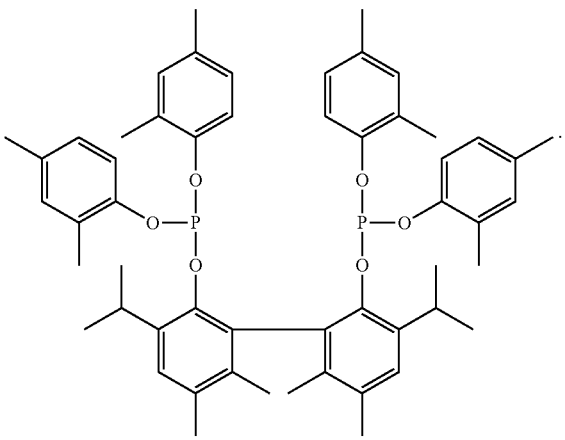

2. The nickel particulate form of statement 1, having at least three of the properties in the group.
3. The nickel particulate form of statement 1 or 2, having at least four of the properties in the group.
4. A nickel particulate form comprising nickel crystallites, wherein the nickel particulate form has a BET Specific Surface Area of at least about 1 m²/gm; at least 10% of the nickel crystallites have a size (C10) that is less than about 20 nm; the nickel crystallites have an average crystallite size of no greater than about 100 nm; and the nickel crystallite size distribution span is greater than about 1.0.
5. The nickel particulate form of any of statements 1-4, wherein the nickel particulate form has a BET Specific Surface Area of at least about 2 m²/g.
6. The nickel particulate form of any of statements 1-5, wherein the nickel particulate form has a BET Specific Surface Area of at least about 4 m²/g.
7. The nickel particulate form of any of statements 1-6, wherein the nickel particulate form has a BET Specific Surface Area of at least about 10 m²/g.
8. The nickel particulate form of any of statements 1-7, wherein the BET SSA/C50 ratio is at least about 0.1×10⁹ m/gm.
9. The nickel particulate form of any of statements 1-8, wherein the average crystallite size of no greater than about 70 nm.
10. The nickel particulate form of any of statements 1-9, wherein the average crystallite size of no greater than about 50 nm.
11. The nickel particulate form of any of statements 1-10, wherein the average crystallite size of no greater than about 30 nm.
12. The nickel particulate form of any of statements 1-11, wherein the BET SSA/C50 ratio is at least about 0.4×10⁹ m/gm.
13. The nickel particulate form of any of statements 1-12, wherein a LD SSA/C50 ratio is at least about 4.3×10⁶·

14. The nickel particulate form of any of statements 1-13, wherein the LD SSA/C50 ratio is at least about $10^7$.
15. The nickel particulate form of any of statements 1-14, wherein at least 10% of the crystallites have a size (C10) that is less than about 10 nm.
16. The nickel particulate form of any of statements 1-15, having an average crystallite size of no greater than about 20-25 nm.
17. The nickel particulate form of any of statements 1-16, with a nickel crystallite size distribution span greater than 1.5.
18. The nickel particulate form of any of statements 1-17, wherein the nickel particulate form on average has at least about $2 \times 10^{15}$ surface crystallites per gram nickel.
19. The nickel particulate form of any of statements 1-18, wherein the nickel particulate form on average has at least about $5 \times 10^{15}$ surface crystallites per gram nickel.
20. The nickel particulate form of any of statements 1-19, wherein the nickel particulate form on average has at least about $1 \times 10^{16}$ surface crystallites per gram nickel.
21. The nickel particulate form of any of statements 1-20, wherein the surface crystallites per gram nickel are calculated for substantially spherical crystallites or substantially cuboidal crystallites.
22. The nickel particulate form of any of statements 1-21, wherein on average per gram there are at least about $2 \times 10^{15}$ surface crystallites per gram nickel as calculated for cuboidal crystallites, or at least about $10^{15}$ surface crystallites per gram nickel as calculated for substantially spherical crystallites, or both.
23. The nickel particulate form of any of statements 1-22, wherein the at least 10% of the particles have a diameter (D10) of no greater than about 4 μm.
24. The nickel particulate form of any of statements 1-23, wherein a ratio of BET Specific Surface Area to Laser Diffraction Specific Surface Area is between 20 and 30.
25. The nickel particulate form of any of statements 1-24, wherein a ratio of BET Specific Surface Area to D10 is from 3 to 5 $m^2/gm/\mu m$ or about $0.5 \times 10^6$ m/gm to about $5 \times 10^6$ m/g.
26. The nickel particulate form of any of statements 1-25, wherein on average there are at least about $5 \times 10^{16}$ surface crystallites of size C10 or less per gram nickel,
27. The nickel particulate form of any of statements 1-26, wherein on average there are at least about $10^{17}$ surface crystallites of size C10 or less per gram nickel.
28. The nickel particulate form of any of statements 1-27, wherein the nickel particulate form is substantially zero-valent nickel.
29. The nickel particulate form of any of statements 1-28, wherein the nickel particulate form is generated by reduction of basic nickel carbonate.
30. The nickel particulate form of any of statements 1-29, wherein the nickel particulate form is generated by reduction of basic nickel carbonate, where the basic nickel carbonate has less than a molar equivalent of carbonate relative to the amount of nickel in the basic nickel carbonate.
31. The nickel particulate form of any of statements 1-30, wherein the nickel particulate form is generated by reduction of basic nickel carbonate, where the basic nickel carbonate has a molar ratio of $NiCO_3:Ni(OH)_2$ that is less than approximately 1.
32. The nickel particulate form of any of statements 1-31, wherein the nickel particulate form is generated by reduction of basic nickel carbonate, where the basic nickel carbonate has a mass ratio of Ni:C of at least 6:1, or at least 7:1, or at least 8:1, or at least 9:1, or at least 10:1.
33. The nickel particulate form of any of statements 1-, wherein the nickel particulate form is generated by reduction of basic nickel carbonate, where the basic nickel carbonate has a mass ratio of Ni:C of 6:1 to about 20:1.
34. The nickel particulate form of any of statements 1-33, wherein the nickel particulate form has been reduced from Ni(II) to zero-valent nickel.
35. The nickel particulate form of any of statements 1-34, wherein the nickel particulate form has been reduced from Ni(II) to zero-valent nickel with hydrogen.
36. The nickel particulate form of any of statements 1-35, wherein the nickel particulate form has been reduced from Ni(II) to zero-valent nickel at 250-400° C.
37. The nickel particulate form of any of statements 1-36, wherein the nickel particulate form is substantially free of another metal.
38. The nickel particulate form of any of statements 1-37, wherein the nickel particulate form is substantially free of aluminum, copper, tungsten, zinc and/or iron.
39. The nickel particulate form of any of statements 1-38, wherein the nickel particulate form is substantially free of alkali metals and/or alkaline earth metals.
40. The nickel particulate form of any of statements 1-39, wherein the nickel particulate form is substantially free of an anion.
41. The nickel particulate form of any of statements 1-40, wherein the nickel particulate form is substantially free of carbonate, hydroxide and/or oxygen.
42. The nickel particulate form of any of statements 1-41, comprising about 0.01 wt % to about 12 wt % sulfur, relative to the total weight of nickel in the mixture.
43. The nickel particulate form of any of statements 1-42, comprising about 0.1 wt % to about 2 wt % sulfur, relative to the total weight of nickel in the mixture.
44. The nickel particulate form of any of statements 1-43, comprising about 0.2 wt % to about 2 wt % sulfur, relative to the total weight of nickel in the mixture.
45. The nickel particulate form of any of statements 1-44, comprising about 0.4 wt % to about 1 wt % sulfur, relative to the total weight of nickel in the mixture.
46. A complex comprising one or more phosphorus-containing ligands and nickel atoms from the nickel particulate form of any of statements 1-45.
47. The complex of statement 46, having hydrocyanation catalytic activity.
48. The complex of statement 46 or 47, having catalytic activity for hydrocyanation of a compound comprising at least one C=C bond.
49. The complex of any of statements 46-48, further comprising about 0.001 wt % to about 15 wt % sulfur, wherein the sulfur weight percentage is relative to the total weight of nickel in the mixture.
50. An organic liquid solution comprising one or more bidentate phosphorus-containing ligands and the nickel particulate form of any of statements 1-45.
51. The solution of statement 50, wherein the nickel particulate form is suspended in the solution.
52. The solution of statement 50 or 51, further comprising one or more pentenenitriles.
53. The solution of any of statements 50-52, wherein the solution comprises one or more pentenenitriles as a solvent.
54. The solution of any of statements 50-53, further comprising a Lewis acid.

55. The solution of any of statements 50-54, wherein the Lewis acid is zinc chloride, ferrous chloride, or a combination thereof.

56. The solution of any of statements 50-55, wherein a complex forms between one or more bidentate phosphorus-containing ligands and nickel atoms from the nickel particulate form.

57. The solution of any of statements 50-56, having hydrocyanation catalytic activity.

58. The solution of any of statements 50-57, having catalytic activity for hydrocyanation of a compound comprising at least one C=C bond.

59. The solution of any of statements 50-58, further comprising about 0.001 wt % to about 15 wt % sulfur, wherein the sulfur weight percentage is relative to the total weight of nickel in the solution.

60. A method of making a zero-valent nickel-ligand complex having catalytic activity, comprising mixing an organic liquid solution comprising one or more bidentate phosphorus-containing ligands and the nickel particulate form of any of statements 1-45.

61. The method of statement 60, wherein the organic liquid solution further comprises a Lewis acid.

62. The method of statement 61, wherein the Lewis acid is zinc chloride, ferrous chloride, or a combination thereof.

63. The method of any of statements 60-62, wherein the organic liquid solution further comprises one or more nitriles.

64. The method of any of statements 60-63, wherein at least the one nitrile is a mononitrile.

65. The method of any of statements 60-64, wherein the organic liquid solution comprises one or more pentenenitriles.

66. The method of any of statements 60-65, wherein the organic liquid solution comprises one or more pentenenitriles as a solvent.

67. The method of any of statements 60-66, wherein a complex forms between one or more bidentate phosphorus-containing ligands and nickel atoms from the nickel particulate form.

68. The method of any of statements 60-67, wherein a complex formed between one or more bidentate phosphorus-containing ligands and nickel atoms from the nickel particulate form has catalytic activity for hydrocyanation of a compound comprising at least one C=C bond.

69. The method of any of statements 60-68, wherein the organic liquid solution further comprises about 0.001 wt % to about 15 wt % sulfur, wherein the sulfur weight percentage is relative to the total weight of nickel in the solution.

70. The method of any of statements 60-69, wherein the one or more of the phosphorus ligands is a ligand of Formula (III):

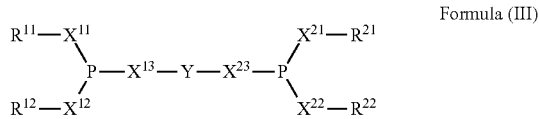

wherein:
X$^{11}$, X$^{12}$, X$^{13}$, X$^{21}$, X$^{22}$ and X$^{23}$ independently represent oxygen or a single direct bond;

R$^{11}$ and R$^{12}$ independently represent identical or different, single or bridged organic radicals;

R$^{21}$ and R$^{22}$ independently represent identical or different, single or bridged organic radicals; and Y represents a bridging group.

71. The method of any of statements 60-70, wherein the one or more of the phosphorus ligands is Ligand (V):

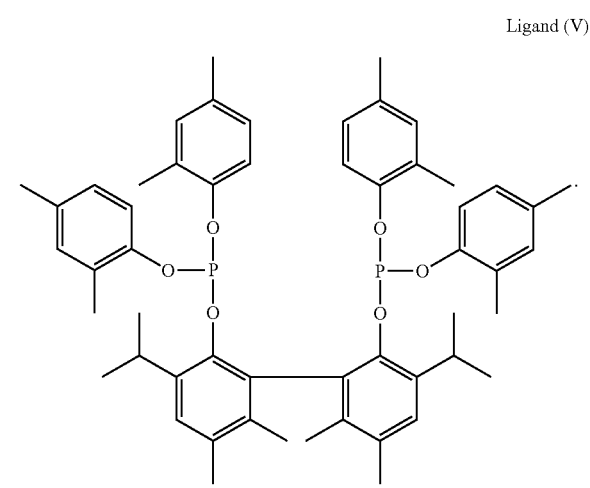

72. A method for hydrocyanating a compound having at least one C=C bond comprising contacting the compound with HC≡N in the presence of a catalyst comprising a zero-valent nickel complex with one or more phosphorus-containing ligands, wherein nickel atoms of the complex are from a nickel particulate form of any of statements 1-45.

73. The method of statement 72, wherein one or more phosphorus-containing ligands comprises a phosphite ligand.

74. The method of statement 72 or 73, wherein one or more phosphorus-containing ligands comprises a bidentate phosphite ligand.

75. The method of any of statements 72-74, wherein the one or more of the phosphorus ligands is a ligand of Formula (III):

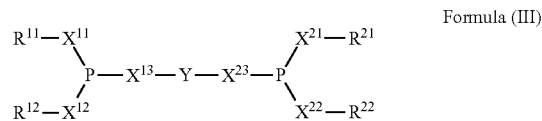

wherein:
X$^{11}$, X$^{12}$, X$^{13}$, X$^{21}$, X$^{22}$ and X$^{23}$ independently represent oxygen or a single direct bond;

R$^{11}$ and R$^{12}$ independently represent identical or different, single or bridged organic radicals;

R$^{21}$ and R$^{22}$ independently represent identical or different, single or bridged organic radicals; and Y represents a bridging group.

76. The method of any of statements 72-75, wherein the bidentate phosphite ligand is Ligand (V):

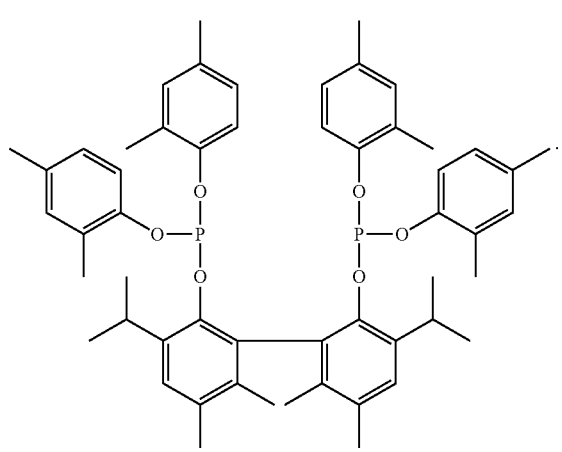

Ligand (V)

77. The method of any of statements 72-76, wherein the organic liquid solution further comprises about 0.001 wt % to about 15 wt % sulfur, wherein the sulfur weight percentage is relative to the total weight of nickel in the solution.

78. A method of identifying whether a basic nickel carbonate test sample will yield a nickel particulate form with nickel atoms that complex with one or more phosphorus-containing ligands, comprising:

(a) calcining a basic nickel carbonate test sample; and (b) observing whether the test sample gives off more or less carbon dioxide compared to a control basic nickel carbonate sample;

wherein the basic nickel carbonate test sample will yield an active nickel particulate form with nickel atoms that substantially complex with one or more phosphorus-containing ligands within about 2 hours, when the basic nickel carbonate test sample gives off less carbon dioxide than the control basic nickel carbonate; and wherein the control basic nickel will yield a nickel particulate form with nickel atoms that substantially do not complex with one or more phosphorus-containing ligands within about 2 hours.

79. A method of identifying whether a nickel test sample will yield a nickel particulate form with nickel atoms that complex with one or more phosphorus-containing ligands, comprising:

(a) reducing the nickel test sample with hydrogen; and (b) observing whether the nickel test sample exhibits a single peak of hydrogen absorption between about 350° C. and 450° C. during reduction;

wherein the nickel test sample will yield an active nickel particulate form with nickel atoms that substantially complex with one or more phosphorus-containing ligands within about 2 hours, when the nickel test sample exhibits a single peak of hydrogen absorption between about 350° C. and 450° C. during reduction.

80. The method of statement 79, wherein the nickel test sample is basic nickel carbonate, nickel oxide, nickel hydroxide, or a mixture thereof.

81. The method of statement 79 or 80, further comprising forming a complex between the nickel atoms of an active nickel particulate form and one or more phosphorus-containing ligands to generate a hydrocyanation catalyst.

82. A method of avoiding waste, comprising:

(a) calcining a basic nickel carbonate test sample; and (b) observing whether the test sample gives off more or less carbon dioxide compared to a control basic nickel carbonate sample;

wherein the basic nickel carbonate test sample will not yield an active nickel particulate form with nickel atoms that substantially do not complex with one or more phosphorus-containing ligands within about 2 hours, when the basic nickel carbonate test sample gives off more carbon dioxide than the control basic nickel carbonate; and wherein, after reduction, the control basic nickel carbonate yields a nickel preparation with nickel atoms that substantially do not complex with one or more phosphorus-containing ligands within about 2 hours after mixing in a organonitrile solvent.

83. The method of statement 82, wherein waste is avoided by identifying a basic nickel carbonate test sample that gives off more carbon dioxide than the control basic nickel carbonate, and not using the basic nickel carbonate from which the basic nickel carbonate test sample was obtained to make a nickel particulate form for use in a hydrocyanation catalyst.

84. The method of statement 82 or 83, wherein waste is avoided by identifying a basic nickel carbonate test sample that gives off more carbon dioxide than the control basic nickel carbonate, and by not using the basic nickel carbonate from which the basic nickel carbonate test sample was obtained to make a nickel preparation because the nickel preparation will not complex with one or more phosphorus-containing ligands within about 2 hours after mixing therewith in a organonitrile solvent.

85. A method of avoiding waste, comprising:

(a) reducing a nickel-containing test sample; and (b) observing whether the nickel test sample exhibits a single peak of hydrogen absorption between about 350° C. and 450° C. during reduction;

wherein the nickel test sample not will yield a nickel particulate form with nickel atoms that substantially complex with one or more phosphorus-containing ligands within about 2 hours after mixing therewith, when the nickel test sample exhibits two peaks of hydrogen absorption between about 300° C. and 450° C. during reduction.

86. The method of statement 85, wherein waste is avoided by identifying the nickel test sample(s) that exhibit two peaks of hydrogen absorption between about 300° C. and 450° C. during reduction, and not using a nickel source from which the nickel test sample(s) were obtained to generate a hydrocyanation catalyst.

87. The method of any of statements 78-86, wherein the one or more phosphorus-containing ligands comprise Ligand (V):

Ligand (V)

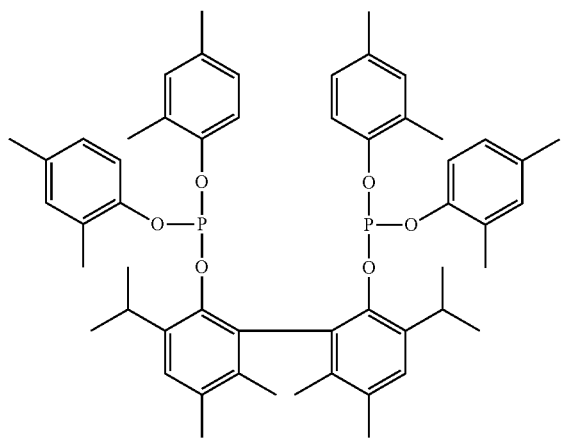

88. A method of generating a nickel hydrocyanation catalyst comprising:
(a) contacting a nickel metal with a sulfur source before or during complex formation between nickel atoms from the nickel metal and one or more phosphorus-containing ligand(s) to thereby form the nickel hydrocyanation catalyst; or
(b) contacting a nickel starting material with a sulfur source, generating nickel metal from the mixture of the nickel starting material and the sulfur source, and contacting the nickel metal with one or more phosphorus-containing ligand(s) to thereby form a complex between nickel atoms from the nickel metal and one or more phosphorus-containing ligands.

89. The method of statement 88, further comprising determining a sulfur content of the nickel metal or the nickel starting material before contacting the nickel metal or the nickel starting material with the sulfur source.

90. The method of statement 89, wherein the sulfur content of the nickel metal or the nickel starting material is determined using infrared (IR) spectroscopy analysis, microcoulometry, inductively coupled plasma (ICP) mass spectrometry or a combination thereof.

91. The method of statement 89 or 90, wherein the nickel metal or the nickel starting material is contacted with the sulfur source if the sulfur content of the nickel metal or the nickel starting material is less than 0.2 wt % to 0.8 wt % relative to the weight of the nickel metal or the nickel starting material.

92. The method of any of statements 88-91, wherein the nickel metal or the nickel starting material is contacted with the sulfur source if the sulfur content of the nickel metal or the nickel starting material is less than 0.4 wt % relative to the weight of the nickel metal or the nickel starting material.

93. The method of any of statements 88-92, wherein the sulfur source is selected from the group consisting of elemental sulfur, sulfur-containing gases, sulfur-containing salts, sulfur-containing ions and combinations thereof.

94. The method of any of statements 88-93, wherein the sulfur source is in liquid, solid, gaseous or a combination of such physical forms.

95. The method of any of statements 88-94, wherein the sulfur source comprises a sulfate, sulfite, sulfide, hyposulfite, thiosulfate, sulfur trioxide, sulfur dioxide, sulfur monoxide, sulfur halide, and a combination thereof.

96. The method of any of statements 88-95, wherein the sulfur source is selected from the group consisting of a polymer of sulfur, a mixture of polymeric chains of sulfur, cyclic sulfur, one or more allotropes of sulfur, and a combination thereof.

97. The method of any of statements 88-96, wherein the sulfur source is selected from the group consisting of hydrogen sulfide, nickel sulfate, nickel sulfite, nickel sulfide, nickel hyposulfite, nickel thiosulfate, sulfur trioxide, sulfur dioxide, sulfur monoxide, disulfur dichloride, sulfur dichloride, sulfur tetrachloride, sulfur chloride pentafluoride, disulfur decafluoride, sulfur hexafluoride, sulfur tetrafluoride, sulfur trifluoride and combinations thereof.

98. The method of any of statements 88-97, wherein the sulfur source is a sulfur-containing nickel salt.

99. The method of any of statements 88-98, wherein the sulfur source is at least 95% to 99.9% free of silicon, sodium, potassium, calcium, magnesium, phosphorus, aluminium, copper, tungsten, mercury, iron and combinations thereof.

100. The method of any of statements 88-99, wherein the sulfur source is contacted with the nickel metal or the nickel starting material when the nickel metal or the nickel starting material is in solution or in solid particulate form.

101. The method of any of statements 88-100, wherein the sulfur source is contacted with the nickel metal or the nickel starting material, before or during suspension of the nickel metal or the nickel starting material in a liquid organic medium or in a gas flow.

102. The method of any of statements 88-101, wherein the nickel metal and/or the nickel starting material is at least 95% to 99.9% free of silicon, sodium, potassium, calcium, magnesium, phosphorus, aluminium, copper, tungsten, mercury, iron and combinations thereof.

103. The method of any of statements 88-102, wherein the nickel starting material is basic nickel carbonate, nickel carbonate, nickel bicarbonate, nickel oxalate, nickel formate, nickel squarate, nickel hydroxide, nickel oxide, nickel salts or a combination thereof.

104. The method of any or statements 88-103, wherein the nickel starting material is contacted with the sulfur source before or after calcining the nickel starting material.

105. The method of any of statements 88-104, wherein the nickel starting material or the nickel metal is contacted with the sulfur source before reduction to zero valent particulate nickel.

106. The method of any or statements 88-105, wherein reduction is at 200° C. to 400° C. for about 3 to about 5 hours.

107. The method of any of statements 88-106, wherein the nickel metal or the nickel starting material is contacted with the sulfur source after reduction of the nickel metal or after reduction of the nickel starting material to zero valent nickel.

108. The method of any of statements 88-107, wherein a weight percentage of about 0.1 wt % to about 50 wt % sulfur is contacted with the nickel metal or the nickel starting material, wherein the sulfur weight percentage is relative to the total weight of nickel in the nickel metal or the nickel starting material.

109. The method of any of statements 88-108, wherein a weight percentage of about 0.2 wt % to about 15 wt % sulfur is contacted with the nickel metal or the nickel starting material, where the sulfur weight percentage is relative to the total weight of nickel in the nickel metal or the nickel starting material.

110. The method of any of statements 88-109, wherein a weight percentage of about 0.4 wt % to about 12 wt % sulfur is contacted with the nickel metal or the nickel starting material, where the sulfur weight percentage is relative to the total weight of nickel in the nickel metal or the nickel starting material.

111. The method of any of statements 88-110, wherein the contacting yields a sulfur to nickel atomic ratio of about 0.003 to about 1.8.

112. The method of any of statements 88-111, wherein the contacting yields a sulfur to nickel atomic ratio of about 0.01 to about 0.2.

113. The method of any of statements 88-112, wherein the contacting yields a sulfur to nickel atomic ratio of about 0.003 to about 0.05.

114. The method of any of statements 88-113, wherein an equilibrium of complex formation is reached by about 2 hours when about 4 wt % nickel is mixed at about 60° C. to 80° C. in an organonitrile solvent with about 0.5 to 2.5 moles Lewis acid per mole bidentate phosphorus-containing ligand.

115. The method of any of statements 88-114, wherein an equilibrium of complex formation is reached by about 30 minutes when about 4% nickel is mixed at about 60° C. to 80° C. in an organonitrile solvent with about 0.5 to 2.5 moles Lewis acid per mole bidentate phosphorus-containing ligand.

116. The method of any of statements 88-115, wherein a Lewis acid is present during complex formation.

117. The method of statement 116, wherein the Lewis acid is selected from the group consisting of zinc chloride, ferrous chloride, or a combination thereof.

118. The method of any of statements 88-117, wherein complex formation occurs in an organonitrile solvent.

119. The method of statement 118, wherein the organonitrile solvent is a pentenenitrile.

120. The method of any of statements 88-119, wherein one or more of the phosphorus ligands is a ligand of Formula (III):

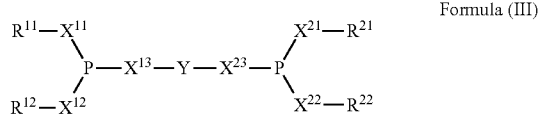

Formula (III)

wherein:

$X^{11}$, $X^{12}$, $X^{13}$, $X^{21}$, $X^{22}$ and $X^{23}$ independently represent oxygen or a single direct bond;

$R^{11}$ and $R^{12}$ independently represent identical or different, single or bridged organic radicals;

$R^{21}$ and $R^{22}$ independently represent identical or different, single or bridged organic radicals; and Y represents a bridging group.

121. The method of any of statements 88-120, wherein one or more of the phosphorus ligands is Ligand (V):

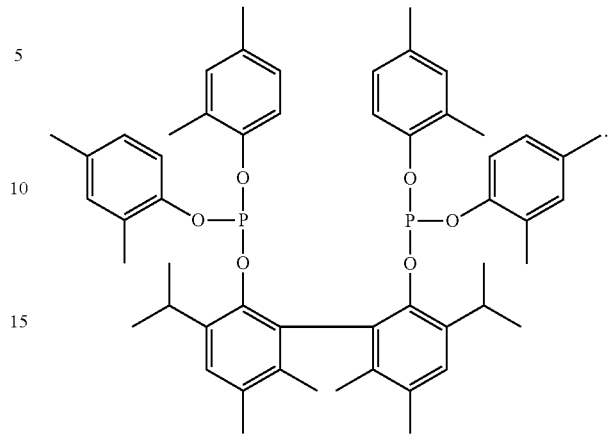

Ligand (V)

122. The method of any of statements 88-121, wherein a complex forms between nickel atoms from the nickel metal and one or more phosphorus-containing ligands mixed under a non-oxygen containing atmosphere.

123. The method of any of statements 88-123, wherein a complex formed between nickel atoms from the nickel metal and one or more phosphorus-containing ligands catalyses hydrocyanation of an olefin.

124. The method of statement 123, wherein the olefin is pentenenitrile.

125. A catalyst preparation mixture comprising nickel metal, one or more phosphorus-containing ligands and about 0.001 wt % to about 15 wt % sulfur, wherein the sulfur weight percentage is relative to the total weight of nickel in the mixture.

126. The catalyst preparation mixture of statement 125, wherein the mixture is in an organonitrile solvent.

127. The catalyst preparation mixture of statement 126, wherein the solvent is a pentenenitrile.

128. The catalyst preparation mixture of any of statements 125-127, further comprising a Lewis acid.

129. The catalyst preparation mixture of statement 125, wherein the Lewis acid is selected from the group consisting of zinc chloride, ferrous chloride, or a combination thereof 130. The catalyst preparation mixture of statement 129, wherein the Lewis acid is zinc chloride.

131. The catalyst preparation mixture of any of statements 125-130, wherein one or more of the phosphorus ligands is a ligand of Formula (III):

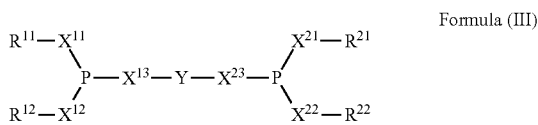

Formula (III)

wherein, $X^{11}$, $X^{12}$, $X^{13}$, $X^{21}$, $X^{22}$ and $X^{23}$ independently represent oxygen or a single direct bond;

$R^{11}$ and $R^{12}$ independently represent identical or different, single or bridged organic radicals;

R²¹ and R²² independently represent identical or different, single or bridged organic radicals; and Y represents a bridging group.

132. The catalyst preparation mixture of any of statements 38-44, wherein one or more of the phosphorus ligands is Ligand (V):

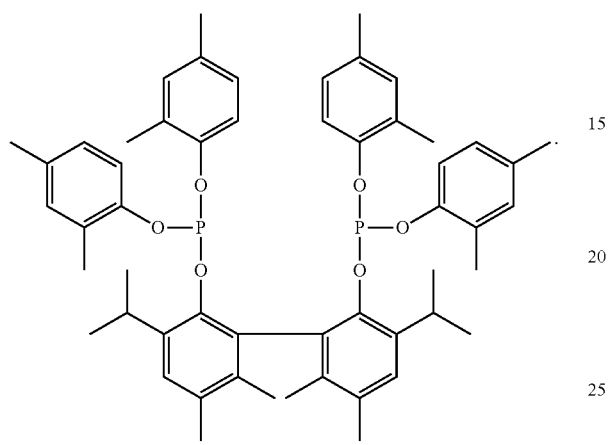

Ligand (V)

133. The catalyst preparation mixture of any of statements 125-132, comprising a weight percent of the one or more phosphorus containing ligands of about 2 to about 8 wt %.

134. The catalyst preparation mixture of any of statements 125-133, comprising a weight percent of the one or more phosphorus containing ligands of about 4.75 to about 5.75 wt %, 135. The catalyst preparation mixture of any of statements 125-134, comprising a weight percent of the one or more phosphorus containing ligands of about 5.25 wt %.

136. The catalyst preparation mixture of any of statements 125-134, comprising a nickel weight percent of about 1 to about 7 wt %.

137. The catalyst preparation mixture of any of statements 125-136, comprising a nickel weight percent of about 4 to about 5 wt %.

138. The catalyst preparation mixture of any of statements 125-137, comprising a zinc to phosphorus containing ligand molar ratio of about 0.5 to about 2.5

139. The catalyst preparation mixture of any of statements 125-138, comprising a zinc to phosphorus containing ligand molar ratio of about 0.70 to about 0.80.

140. The catalyst preparation mixture of any of statements 125-139, comprising about 0.01 wt % to about 12 wt % sulfur, relative to the total weight of nickel in the mixture.

141. A complex formed between nickel atoms and one or more phosphorus-containing ligands comprising about 0.00001 wt % to about 15 wt % sulfur, wherein the sulfur weight percentage is relative to the total weight of nickel in the complex.

142. The complex of statement 141, comprising about 0.0001 wt % to about 2 wt % sulfur.

143. The complex of statement 141 or 142, wherein one or more of the phosphorus ligands is a ligand of Formula (III):

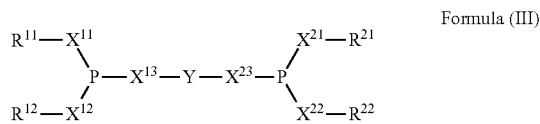

Formula (III)

wherein, $X^{11}, X^{12}, X^{13}, X^{21}, X^{22}$ and $X^{23}$ independently represent oxygen or a single direct bond;

$R^{11}$ and $R^{12}$ independently represent identical or different, single or bridged organic radicals;

$R^{21}$ and $R^{22}$ independently represent identical or different, single or bridged organic radicals; and Y represents a bridging group.

144. The complex of any of statements 141-143, wherein one or more of the phosphorus ligands is Ligand (V):

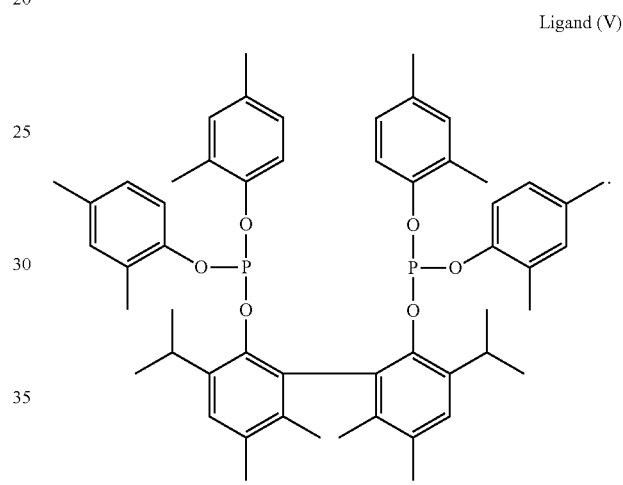

Ligand (V)

145. The complex of any of statements 141-144, wherein the complex is in an organonitrile solvent.

146. The complex of any of statements 141-145, wherein the complex is in a pentenenitrile solvent.

The foregoing features and aspects are set forth without any loss of generality to, and without imposing limitations upon any claimed invention. It is to be understood that this disclosure is not limited to particular aspects described, as such can vary. It is also to be understood that the terminology used herein is for the purpose of describing particular aspects only, and is not intended to be limiting, since the scope of the present disclosure will be limited only by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. As will be apparent to those of skill in the art upon reading this disclosure, each of the individual aspects described and illustrated herein has discrete components and features that can be readily separated from or combined with the features of any of the other several examples without departing from the scope or spirit of the present disclosure. Where features or aspects of the invention are described in terms of Markush groups, those skilled in the art will recognize that the invention is also thereby described in terms of any individual member or subgroup of members of the Markush group. Any recited method can be carried out in the order of events recited or in any other order that is logically possible.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. Applicants reserve the right to physically incorporate into this specification any and all materials and information from any such cited patents or publications. The citation of any publication is for its disclosure prior to the filing date and should not be construed as an admission that the present disclosure is not entitled to antedate such publication by virtue of prior disclosure. Further, the dates of publication provided could be different from the actual publication dates that can need to be independently confirmed. All patents and publications referenced or mentioned herein are also indicative of the levels of skill of those skilled in the art to which the invention pertains.

The following claims describe additional aspects of the invention.

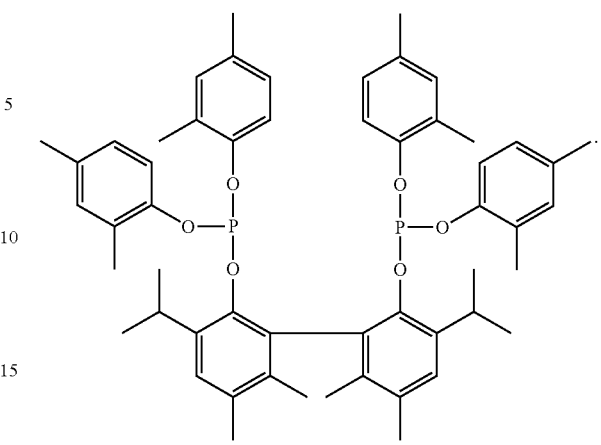

What is claimed:

1. A nickel particulate form comprising nickel crystallites, wherein the nickel particulate form has a BET Specific Surface Area of at least about 1 $m^2/gm$; at least 10% of the nickel crystallites have a size (C10) that is less than about 20 nm; the nickel crystallites have an average crystallite size of no greater than about 100 nm; and the nickel crystallite size distribution span is greater than about 1.0.

2. The nickel particulate form of claim 1, wherein the nickel particulate form has a BET Specific Surface Area/C50 ratio of not less than $0.07 \times 10^9$ m/gm.

3. The nickel particulate form of claim 1, wherein the nickel particulate form on average has at least about $10^{15}$ surface crystallites per gram of nickel.

4. The nickel particulate form of claim 1, wherein at least 10% of the particles of the form have a size (D10) of no greater than about 6 μm.

5. The nickel particulate form of claim 1, which has a Laser Diffraction Specific Surface Area of at least about 0.4 $m^2/gm$.

6. The nickel particulate form of claim 1, which has a BET Specific Surface Area to D10 ratio of about $0.3 \times 10^6$ m/gm to about $10.0 \times 10^6$ m/gm.

7. The nickel particulate form of claim 1, which has on average at least about $10^{16}$ surface crystallites per gram nickel that are smaller than or equal to size C10.

8. The nickel particulate form of claim 1, wherein an equilibrium of complex formation between Ligand (V) and nickel atoms from the nickel particulate form is reached within about 2 hours when about 4 to 5 wt % of the nickel particulate form is mixed with 3-pentenenitrile containing approximately 5.25 wt % Ligand (V) and approximately 6300 ppm $ZnCl_2$; and wherein Ligand (V) has the following formula:

9. The nickel particulate form of claim 1, wherein the nickel particulate form has a BET Specific Surface Area of at least about 2 $m^2/g$.

10. The nickel particulate form of claim 1, wherein the nickel particulate form has a BET Specific Surface Area of at least about 4 $m^2/g$.

11. The nickel particulate form of claim 1, wherein the nickel particulate form has a BET Specific Surface Area of at least 10 $m^2/g$.

12. The nickel particulate form of claim 1, wherein the BET SSA/C50 ratio is at least about $0.1 \times 10^9$ m/gm.

13. The nickel particulate form of claim 1, wherein the average crystallite size of no greater than about 70 nm.

14. The nickel particulate form of claim 1, wherein the average crystallite size of no greater than about 50 nm.

15. The nickel particulate form of claim 1, wherein the average crystallite size of no greater than about 30 nm.

16. The nickel particulate form of claim 1, wherein the BET SSA/C50 ratio is at least about $0.4 \times 10^9$ m/gm.

17. The nickel particulate form of claim 1, wherein a LD SSA/C50 ratio is at least about $4.3 \times 10^6$.

18. The nickel particulate form of claim 1, wherein the LD SSA/C50 ratio is at least about $10^7$.

19. The nickel particulate form of claim 1, wherein at least 10% of the crystallites have a size (C10) that is less than about 10 nm.

20. The nickel particulate form of claim 1, which has an average crystallite size of no greater than about 20-25 nm.

21. The nickel particulate form of claim 1, which has a nickel crystallite size distribution span greater than 1.5.

22. The nickel particulate form of claim 1, wherein the nickel particulate form on average has at least about $2 \times 10^{15}$ surface crystallites per gram nickel.

23. The nickel particulate form of claim 1, wherein the surface crystallites per gram nickel are calculated for substantially cuboidal crystallites.

24. The nickel particulate form of claim 1, wherein the surface crystallites per gram nickel are calculated for substantially spherical crystallites.

25. The nickel particulate form of claim 1, wherein on average per gram there are at least about $2 \times 10^{15}$ surface crystallites per gram nickel as calculated for cuboidal crystallites, or at least about $10^{15}$ surface crystallites per gram nickel as calculated for substantially spherical crystallites, or both.

26. The nickel particulate form of claim 1, wherein a ratio of BET Specific Surface Area to Laser Diffraction Specific Surface Area is between 20 and 30.

27. The nickel particulate form of claim 1, wherein a ratio of BET Specific Surface Area to D10 is from 3 to 5 $m^2/gm/\mu m$ or about $0.5 \times 10^6$ m/gm to about $5 \times 10^6$ m/g.

28. The nickel particulate form of claim 1, wherein on average there are at least about $10^{16}$ surface crystallites of size C10 or less per gram nickel.

29. The nickel particulate form of claim 1, wherein on average there are at least about $10^{17}$ surface crystallites of size C10 or less per gram nickel.

30. The nickel particulate form of claim 1, wherein the nickel particulate form is substantially zero-valent nickel.

31. The nickel particulate form of claim 1, wherein the nickel particulate form is generated by reduction of a nickel starting material.

32. The nickel particulate form of claim 1, wherein the nickel particulate form is generated by reduction of a nickel starting material selected from the group consisting of basic nickel carbonate, nickel carbonate, nickel bicarbonate, nickel oxalate, nickel formate, nickel squarate, nickel hydroxide, nickel oxide, nickel salts or a combination thereof.

33. The nickel particulate form of claim 1, wherein the nickel particulate form has been reduced from Ni(II) to zero-valent nickel at 250-400° C.

34. The nickel particulate form of claim 1, wherein the nickel particulate form is at least 95% to 99.9% free of another metal.

35. The nickel particulate form of claim 1, wherein the nickel particulate form is at least 95% to 99.9% free of aluminum, copper, tungsten, zinc and/or iron.

36. The nickel particulate form of claim 1, wherein the nickel particulate form is substantially free of alkali metals and/or alkaline earth metals.

37. The nickel particulate form of claim 1, wherein the nickel particulate form is at least 95% to 99.9% free of an anion.

38. The nickel particulate form of claim 1, wherein the nickel particulate form is at least 95% to 99.9% free of carbonate, hydroxide and/or oxygen.

39. The nickel particulate form of claim 1, comprising about 0.01 wt % to about 12 wt % sulfur, relative to the total weight of nickel in the mixture.

40. The nickel particulate form of claim 1, comprising about 0.1 wt % to about 2 wt % sulfur, relative to the total weight of nickel in the mixture.

41. The nickel particulate form of claim 1, comprising about 0.2 wt % to about 2 wt % sulfur, relative to the total weight of nickel in the mixture.

42. The nickel particulate form of claim 1, comprising about 0.4 wt % to about 1 wt % sulfur, relative to the total weight of nickel in the mixture.

* * * * *